US011033705B2

(12) United States Patent
Zapol et al.

(10) Patent No.: US 11,033,705 B2
(45) Date of Patent: *Jun. 15, 2021

(54) SYSTEMS AND METHODS FOR AMBULATORY GENERATION OF NITRIC OXIDE

(71) Applicant: Third Pole, Inc., Waltham, MA (US)

(72) Inventors: David G. Zapol, San Francisco, CA (US); Gregory W. Hall, Belmont, MA (US); Wolfgang Scholz, Beverly, MA (US); Benjamin Apollonio, Lunenburg, MA (US); Frank Heirtzler, Londonderry, NH (US); Andrew Ferencz, Southborough, MA (US)

(73) Assignee: Third Pole, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/724,233

(22) Filed: Dec. 21, 2019

(65) Prior Publication Data

US 2020/0139072 A1 May 7, 2020

Related U.S. Application Data

(63) Continuation of application No. 16/363,505, filed on Mar. 25, 2019, now Pat. No. 10,576,239, which is a
(Continued)

(51) Int. Cl.
*A61M 16/12* (2006.01)
*A61M 16/00* (2006.01)
(Continued)

(52) U.S. Cl.
CPC .............. *A61M 16/12* (2013.01); *A61K 33/00* (2013.01); *A61M 16/0057* (2013.01);
(Continued)

(58) Field of Classification Search
CPC ............ A61M 16/0093; A61M 16/022; A61M 16/024; A61M 16/101; A61M 16/107;
(Continued)

(56) References Cited

U.S. PATENT DOCUMENTS

| 709,867 A | 9/1902 | Bradley et al. |
| 2,485,478 A | 10/1949 | Cotton |

(Continued)

FOREIGN PATENT DOCUMENTS

| CN | 1099997 | 3/1995 |
| CN | 1730115 | 2/2006 |

(Continued)

OTHER PUBLICATIONS

Bellerophon, "A Dose Escalation Study to Assess the Safety and Efficacy of Pulsed iNO in Subjects With Pulmonary Fibrosis", Aug. 30, 2017, https://clinicaltrials.gov/ct2/show/NCT03267108.

(Continued)

*Primary Examiner* — Valerie L Woodward
(74) *Attorney, Agent, or Firm* — Greenberg Traurig, LLP; David J. Dykeman; Jaime L. Burke

(57) ABSTRACT

Systems and methods are provided for portable and compact nitric oxide (NO) generation that can be embedded into other therapeutic devices or used alone. In some embodiments, an ambulatory NO generation system can be comprised of a controller and disposable cartridge. The cartridge can contain filters and scavengers for preparing the gas used for NO generation and for scrubbing output gases prior to patient inhalation. The system can utilize an oxygen concentrator to increase nitric oxide production and compliment oxygen generator activity as an independent device. The system can also include a high voltage electrode assembly (Continued)

that is easily assembled and installed. Various nitric oxide delivery methods are provided, including the use of a nasal cannula.

28 Claims, 68 Drawing Sheets

Related U.S. Application Data continuation of application No. 15/907,258, filed on Feb. 27, 2018, now Pat. No. 10,328,228.

(60) Provisional application No. 62/614,492, filed on Jan. 7, 2018, provisional application No. 62/574,173, filed on Oct. 18, 2017, provisional application No. 62/553,572, filed on Sep. 1, 2017, provisional application No. 62/509,394, filed on May 22, 2017, provisional application No. 62/463,956, filed on Feb. 27, 2017, provisional application No. 62/463,943, filed on Feb. 27, 2017.

(51) Int. Cl.
*A61M 16/04* (2006.01)
*A61M 16/06* (2006.01)
*C01B 21/32* (2006.01)
*A61M 16/10* (2006.01)
*A61M 16/20* (2006.01)
*A61K 33/00* (2006.01)

(52) U.S. Cl.
CPC ...... *A61M 16/0093* (2014.02); *A61M 16/022* (2017.08); *A61M 16/024* (2017.08); *A61M 16/04* (2013.01); *A61M 16/0666* (2013.01); *A61M 16/101* (2014.02); *A61M 16/107* (2014.02); *A61M 16/202* (2014.02); *C01B 21/32* (2013.01); *A61M 2202/0275* (2013.01); *A61M 2202/0283* (2013.01); *A61M 2205/05* (2013.01); *A61M 2205/054* (2013.01); *A61M 2205/125* (2013.01); *A61M 2205/3584* (2013.01); *A61M 2205/502* (2013.01); *A61M 2205/80* (2013.01); *A61M 2205/8206* (2013.01); *A61M 2209/088* (2013.01)

(58) Field of Classification Search
CPC ................ A61M 16/12; A61M 16/202; A61M 16/122–127; A61M 2202/0275
See application file for complete search history.

(56) References Cited

U.S. PATENT DOCUMENTS

| | | |
|---|---|---|
| 2,485,481 A | 10/1949 | Cotton |
| 2,525,938 A | 10/1950 | Peck |
| 2,684,448 A | 7/1954 | Nilles |
| 3,225,309 A | 10/1965 | Phelps |
| 4,287,040 A | 9/1981 | Alamaro |
| 4,500,563 A | 2/1985 | Ellenberger et al. |
| 4,505,795 A | 3/1985 | Alamaro |
| 4,680,694 A | 7/1987 | Huynh et al. |
| 4,695,358 A | 9/1987 | Mizuno et al. |
| 4,705,670 A | 11/1987 | O'Hare |
| 4,816,229 A | 3/1989 | Jensen et al. |
| 4,877,589 A | 10/1989 | Conrad |
| 5,285,372 A | 2/1994 | Huynh et al. |
| 5,378,436 A | 1/1995 | Endoh et al. |
| 5,396,882 A * | 3/1995 | Zapol ............ A61M 15/02 128/200.14 |
| 5,471,977 A | 12/1995 | Olsson et al. |
| 5,485,827 A | 1/1996 | Zapol et al. |
| 5,531,218 A | 7/1996 | Krebs |
| 5,546,935 A | 8/1996 | Champeau |
| 5,558,083 A | 9/1996 | Bathe et al. |
| 5,573,733 A | 11/1996 | Salama |
| 5,674,361 A | 10/1997 | Marinack |
| 5,692,495 A | 12/1997 | Sheu |
| 5,732,693 A | 3/1998 | Bathe et al. |
| 5,749,937 A | 5/1998 | Detering et al. |
| 5,752,504 A | 5/1998 | Bathe |
| 5,827,420 A | 10/1998 | Shirazi et al. |
| 5,839,433 A | 11/1998 | Higenbottam |
| 5,845,633 A | 12/1998 | Psaros |
| 6,089,229 A | 7/2000 | Bathe et al. |
| 6,109,260 A | 8/2000 | Bathe |
| 6,125,846 A | 10/2000 | Bathe et al. |
| 6,164,276 A | 12/2000 | Bathe et al. |
| 6,186,140 B1 | 2/2001 | Hoague |
| 6,197,091 B1 | 3/2001 | Ji et al. |
| 6,224,653 B1 | 5/2001 | Shvedchikov et al. |
| 6,250,302 B1 | 6/2001 | Rantala |
| 6,296,827 B1 | 10/2001 | Castor et al. |
| 6,432,077 B1 | 8/2002 | Stenzler |
| 6,532,956 B2 | 3/2003 | Hill |
| 6,536,429 B1 | 3/2003 | Pavlov et al. |
| 6,581,599 B1 | 6/2003 | Stenzler |
| 6,668,828 B1 | 12/2003 | Figley et al. |
| 6,758,214 B2 | 7/2004 | Fine et al. |
| 6,920,876 B2 | 7/2005 | Miller et al. |
| 6,955,171 B1 | 10/2005 | Figley et al. |
| 6,955,790 B2 | 10/2005 | Castor et al. |
| 6,984,256 B2 | 1/2006 | Lamprecht et al. |
| 6,986,351 B2 | 1/2006 | Figley et al. |
| 7,025,869 B2 | 4/2006 | Fine et al. |
| 7,040,313 B2 | 5/2006 | Fine et al. |
| 7,122,018 B2 | 10/2006 | Stenzler et al. |
| 7,220,393 B2 | 5/2007 | Miller et al. |
| 7,255,105 B2 | 8/2007 | Figley et al. |
| 7,312,584 B2 | 12/2007 | Tamita et al. |
| 7,335,181 B2 | 2/2008 | Miller et al. |
| 7,520,866 B2 | 1/2009 | Stenzler et al. |
| 7,485,324 B2 | 2/2009 | Miller et al. |
| 7,498,000 B2 | 3/2009 | Pekshev et al. |
| 7,516,742 B2 | 4/2009 | Stenzler et al. |
| 7,523,752 B2 | 4/2009 | Montgomery et al. |
| 7,531,133 B2 | 5/2009 | Hole et al. |
| 7,560,076 B2 | 7/2009 | Rounbehler et al. |
| 7,589,473 B2 | 9/2009 | Suslov |
| 7,597,731 B2 | 10/2009 | Palmerton et al. |
| 7,618,594 B2 | 11/2009 | Rounbehler et al. |
| 7,744,812 B2 | 6/2010 | Witherspoon et al. |
| 7,861,516 B2 | 1/2011 | Allanson et al. |
| 7,861,717 B1 | 1/2011 | Krebs |
| 7,914,743 B2 | 3/2011 | Fine et al. |
| 7,947,227 B2 | 5/2011 | Fine et al. |
| 7,955,294 B2 | 6/2011 | Stenzler et al. |
| 8,030,849 B2 | 10/2011 | Suslov |
| 8,043,252 B2 | 10/2011 | Miller et al. |
| 8,057,742 B2 | 11/2011 | Rounbehler et al. |
| 8,066,904 B2 | 11/2011 | Fine et al. |
| 8,079,998 B2 | 12/2011 | Hole et al. |
| 8,083,997 B2 | 12/2011 | Rounbehler et al. |
| 8,091,549 B2 | 1/2012 | Montgomery et al. |
| 8,151,791 B2 | 4/2012 | Arlow et al. |
| 8,173,072 B2 | 5/2012 | Fine et al. |
| 8,187,544 B2 | 5/2012 | Fine et al. |
| 8,211,368 B2 | 7/2012 | Fine et al. |
| 8,221,800 B2 | 7/2012 | Fine et al. |
| 8,226,916 B2 | 7/2012 | Rounbehler et al. |
| 8,246,725 B2 | 8/2012 | Rounbehler et al. |
| 8,268,252 B2 | 9/2012 | Fuller et al. |
| 8,282,966 B2 | 10/2012 | Baldassarre et al. |
| 8,291,904 B2 | 10/2012 | Bathe et al. |
| 8,293,284 B2 | 10/2012 | Baldassarre et al. |
| 8,344,627 B1 | 1/2013 | Hooke et al. |
| 8,371,296 B2 | 2/2013 | Fine et al. |
| 8,377,462 B2 | 2/2013 | DesNoyer et al. |
| 8,397,721 B2 | 3/2013 | Montgomery et al. |
| D679,366 S | 4/2013 | Fuller |
| 8,408,206 B2 | 4/2013 | Montgomery et al. |
| 8,431,163 B2 | 4/2013 | Baldassarre et al. |

(56) References Cited

U.S. PATENT DOCUMENTS

| | | |
|---|---|---|
| D688,352 S | 8/2013 | Fuller |
| 8,517,015 B2 | 8/2013 | Montgomery et al. |
| 8,518,457 B2 | 8/2013 | Miller et al. |
| 8,573,209 B2 | 11/2013 | Bathe et al. |
| 8,573,210 B2 | 11/2013 | Bathe et al. |
| 8,574,531 B2 | 11/2013 | Miller et al. |
| 8,580,109 B2 | 11/2013 | Kruckenberg et al. |
| 8,607,785 B2 | 12/2013 | Fine et al. |
| 8,607,792 B2 | 12/2013 | Montgomery et al. |
| 8,609,026 B2 | 12/2013 | Fine et al. |
| 8,609,028 B2 | 12/2013 | Rounbehler et al. |
| 8,613,958 B2 | 12/2013 | Fine |
| 8,616,204 B2 | 12/2013 | Montgomery et al. |
| 8,646,445 B2 | 2/2014 | Fine et al. |
| D701,963 S | 4/2014 | Abarbanel et al. |
| 8,685,467 B2 | 4/2014 | Miller et al. |
| 8,701,657 B2 | 4/2014 | Fine et al. |
| 8,715,577 B2 | 5/2014 | Fine et al. |
| 8,717,733 B2 | 5/2014 | Gefter et al. |
| 8,720,440 B2 | 5/2014 | Montgomery et al. |
| 8,741,222 B2 | 6/2014 | Fine et al. |
| 8,757,148 B2 | 6/2014 | Montgomery et al. |
| 8,770,199 B2 | 7/2014 | Flanagan et al. |
| 8,776,794 B2 | 7/2014 | Bathe et al. |
| 8,776,795 B2 | 7/2014 | Bathe et al. |
| 8,790,715 B2 | 7/2014 | Montgomery et al. |
| 8,795,222 B2 | 8/2014 | Stenzler et al. |
| 8,795,741 B2 | 8/2014 | Baldassarre |
| 8,808,655 B2 | 8/2014 | Solovyov et al. |
| 8,821,801 B2 | 9/2014 | Rounbehler et al. |
| 8,821,828 B2 | 9/2014 | Hilbig et al. |
| 8,846,112 B2 | 9/2014 | Baldassarre |
| 8,887,720 B2 | 11/2014 | Fine et al. |
| 8,893,717 B2 | 11/2014 | Montgomery et al. |
| 8,944,049 B2 | 2/2015 | Fine et al. |
| 9,095,534 B2 | 8/2015 | Stenzler et al. |
| 9,108,016 B2 | 8/2015 | Acker et al. |
| 9,180,217 B2 | 11/2015 | Arnold et al. |
| 9,192,718 B2 | 11/2015 | Fine |
| 9,265,911 B2 | 2/2016 | Bathe et al. |
| 9,279,794 B2 | 3/2016 | Tolmie et al. |
| 9,295,802 B2 | 3/2016 | Bathe et al. |
| 9,351,994 B2 | 5/2016 | Montgomery et al. |
| 9,408,994 B2 | 5/2016 | Fine et al. |
| 9,408,993 B2 | 8/2016 | Bathe et al. |
| 9,522,249 B2 | 12/2016 | Rounbehler et al. |
| 9,550,039 B2 | 1/2017 | Flanagan et al. |
| 9,550,040 B2 | 1/2017 | Acker et al. |
| 9,573,110 B2 | 2/2017 | Montgomery et al. |
| 9,604,028 B2 | 3/2017 | Fine et al. |
| 9,701,538 B2 | 7/2017 | Fine et al. |
| 9,713,244 B2 | 7/2017 | Tabata et al. |
| 9,770,570 B2 | 9/2017 | Schnictman et al. |
| 9,795,756 B2 | 10/2017 | Flanagan et al. |
| 9,895,199 B2 | 2/2018 | Montgomery et al. |
| 9,896,337 B2 | 2/2018 | Montgomery et al. |
| 9,956,373 B2 | 5/2018 | Rounbehler et al. |
| 9,982,354 B2 | 5/2018 | Kim |
| 10,081,544 B2 | 9/2018 | Fine et al. |
| 10,086,352 B2 | 10/2018 | Fine et al. |
| 10,099,029 B2 | 10/2018 | Montgomery et al. |
| 10,124,142 B2 | 11/2018 | Rounbehler et al. |
| 10,179,222 B2 | 1/2019 | Fine et al. |
| 10,213,572 B2 | 2/2019 | Gellman et al. |
| 10,239,038 B2 | 3/2019 | Zapol et al. |
| 10,279,139 B2 | 5/2019 | Zapol et al. |
| 10,286,176 B2 * | 5/2019 | Zapol .................. C01B 21/32 |
| 10,293,133 B2 | 5/2019 | Zapol et al. |
| 10,328,228 B2 * | 6/2019 | Zapol ................... A61K 33/00 |
| 10,398,820 B2 * | 9/2019 | Potenziano .......... A61B 5/0215 |
| 10,426,913 B2 | 10/2019 | Tolmie et al. |
| 10,434,276 B2 | 10/2019 | Zapol et al. |
| 10,532,176 B2 | 1/2020 | Zapol et al. |
| 10,548,920 B2 | 2/2020 | Montgomery et al. |
| 10,556,082 B2 | 2/2020 | Flanagan et al. |
| 10,556,086 B2 | 2/2020 | Goldstein et al. |
| 10,576,239 B2 * | 3/2020 | Zapol .................... A61M 16/12 |
| 10,682,486 B1 | 6/2020 | Moon et al. |
| 10,695,523 B2 | 6/2020 | Zapol et al. |
| 10,737,051 B2 | 8/2020 | Gellman et al. |
| 10,758,703 B2 | 9/2020 | Kohlmann et al. |
| 10,773,046 B2 | 9/2020 | Schnitman et al. |
| 10,780,241 B2 | 9/2020 | Fine et al. |
| 10,814,092 B2 | 10/2020 | Rounbehler et al. |
| 10,946,163 B2 | 3/2021 | Gillerman et al. |
| 2001/0031230 A1 | 10/2001 | Castor et al. |
| 2001/0035186 A1 | 11/2001 | Hill |
| 2002/0185126 A1 | 12/2002 | Krebs |
| 2004/0019274 A1 | 1/2004 | Galloway, Jr. et al. |
| 2004/0028753 A1 | 2/2004 | Hedenstierna et al. |
| 2004/0031248 A1 | 2/2004 | Lindsay |
| 2004/0181149 A1 | 9/2004 | Langlotz et al. |
| 2005/0172971 A1 | 8/2005 | Kolobow et al. |
| 2005/0218007 A1 | 10/2005 | Pekshev et al. |
| 2005/0263150 A1 | 12/2005 | Chathampally et al. |
| 2005/0281465 A1 | 12/2005 | Marquart et al. |
| 2006/0025700 A1 | 2/2006 | Fallik |
| 2006/0172018 A1 | 8/2006 | Fine et al. |
| 2006/0207594 A1 | 9/2006 | Stenzler et al. |
| 2006/0276844 A1 | 12/2006 | Alon et al. |
| 2007/0151561 A1 | 7/2007 | Laurila |
| 2007/0181126 A1 * | 8/2007 | Tolmie ................ A61M 16/085 128/204.21 |
| 2007/0190184 A1 | 8/2007 | Montgomery et al. |
| 2008/0017030 A1 | 1/2008 | Fleck |
| 2008/0078382 A1 | 4/2008 | LeMahieu et al. |
| 2008/0135044 A1 | 6/2008 | Freitag et al. |
| 2008/0176335 A1 | 7/2008 | Alberti et al. |
| 2008/0202509 A1 | 8/2008 | Dillon et al. |
| 2010/0030091 A1 | 2/2010 | Fine |
| 2010/0043789 A1 | 2/2010 | Fine et al. |
| 2010/0089392 A1 | 4/2010 | Fine et al. |
| 2010/0189808 A1 | 7/2010 | Gupta et al. |
| 2010/0275911 A1 | 11/2010 | Arlow et al. |
| 2010/0330193 A1 | 12/2010 | Baldassarre et al. |
| 2011/0140607 A1 * | 6/2011 | Moore ..................... H05H 1/30 315/111.21 |
| 2011/0240019 A1 | 10/2011 | Fine et al. |
| 2012/0093948 A1 * | 4/2012 | Fine ..................... A61M 16/10 424/718 |
| 2012/0279500 A1 | 11/2012 | Singvogel et al. |
| 2012/0285449 A1 | 11/2012 | Fine et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2013/0239963 A1 | 9/2013 | Goldstein et al. |
| 2013/0309328 A1 | 11/2013 | Watts et al. |
| 2014/0020685 A1 | 1/2014 | Szabo |
| 2014/0031668 A1 | 1/2014 | Mobasser et al. |
| 2014/0127081 A1 | 5/2014 | Fine et al. |
| 2014/0127330 A1 | 5/2014 | Fine et al. |
| 2014/0144436 A1 | 5/2014 | Fine et al. |
| 2014/0144444 A1 | 5/2014 | Fine et al. |
| 2014/0158121 A1 | 6/2014 | Flanagan et al. |
| 2014/0166009 A1 | 6/2014 | Flanagan et al. |
| 2014/0216452 A1 | 8/2014 | Miller et al. |
| 2014/0251787 A1 | 9/2014 | Montgomery et al. |
| 2014/0363525 A1 | 12/2014 | Montgomery et al. |
| 2014/0377378 A1 | 12/2014 | Baldassarre |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0090261 A1 | 4/2015 | Crosbie |
| 2015/0101604 A1 | 4/2015 | Crosbie |
| 2015/0174158 A1 | 6/2015 | Av-Gay et al. |
| 2015/0272988 A1 | 10/2015 | Av-Gay et al. |
| 2015/0328430 A1 | 11/2015 | Miller et al. |
| 2016/0022731 A1 | 1/2016 | Av-Gay et al. |
| 2016/0030699 A1 * | 2/2016 | Zapol ................ A61M 16/0003 128/202.26 |
| 2016/0038710 A1 | 2/2016 | Zapol et al. |
| 2016/0106949 A1 | 4/2016 | Kohlmann et al. |

(56) References Cited

U.S. PATENT DOCUMENTS

| | | | |
|---|---|---|---|
| 2016/0121071 A1 | 5/2016 | Moon et al. |
| 2016/0151598 A1 | 6/2016 | Fine |
| 2016/0183841 A1 | 6/2016 | Duindam et al. |
| 2016/0191887 A1 | 6/2016 | Casas |
| 2016/0228670 A1 | 8/2016 | Av-Gay et al. |
| 2016/0243328 A1 | 8/2016 | Tolmie et al. |
| 2016/0271169 A1 | 9/2016 | Potenziano et al. |
| 2016/0279165 A1 | 9/2016 | Av-Gay et al. |
| 2016/0324580 A1 | 11/2016 | Esterberg |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0112871 A1 | 4/2017 | Nelson et al. |
| 2017/0128694 A1 | 5/2017 | Acker et al. |
| 2017/0143758 A1 | 5/2017 | Greenberg et al. |
| 2017/0165294 A1 | 6/2017 | Dasse et al. |
| 2017/0182088 A1 | 6/2017 | Dasse et al. |
| 2017/0232166 A1 | 8/2017 | Potenziano et al. |
| 2017/0239289 A1 | 8/2017 | Av-Gay et al. |
| 2017/0259025 A1 | 9/2017 | Fine et al. |
| 2018/0049622 A1 | 2/2018 | Ryan et al. |
| 2018/0104432 A1 | 4/2018 | Flanagan et al. |
| 2018/0125883 A1 | 5/2018 | Av-Gay et al. |
| 2018/0126111 A1 | 5/2018 | Moon et al. |
| 2018/0133246 A1 | 5/2018 | Av-Gay et al. |
| 2018/0169370 A1 | 6/2018 | Montgomery et al. |
| 2018/0243527 A1 | 8/2018 | Zapol et al. |
| 2018/0243528 A1 | 8/2018 | Zapol et al. |
| 2018/0280920 A1 | 10/2018 | Zapol et al. |
| 2018/0296790 A1 | 10/2018 | Zapol et al. |
| 2018/0311460 A1 | 11/2018 | Rounbehler et al. |
| 2019/0038864 A1 | 2/2019 | Montgomery et al. |
| 2019/0092639 A1 | 3/2019 | Fine et al. |
| 2019/0127223 A1 | 5/2019 | Montgomery et al. |
| 2019/0135633 A1 | 5/2019 | Montgomery et al. |
| 2019/0143068 A1 | 5/2019 | Rounbehler et al. |
| 2019/0209993 A1 | 7/2019 | Fine et al. |
| 2019/0217042 A1 | 7/2019 | Zapol et al. |
| 2019/0217043 A1 | 7/2019 | Fine et al. |
| 2019/0233288 A1 | 8/2019 | Montgomery et al. |
| 2019/0233289 A1 | 8/2019 | Montgomery et al. |
| 2019/0276313 A1 | 9/2019 | Montgomery et al. |
| 2019/0314596 A1 | 10/2019 | Zapol et al. |
| 2019/0374739 A1 | 12/2019 | Tolmie et al. |
| 2020/0094011 A1 | 3/2020 | Zapol et al. |
| 2020/0139071 A1 | 5/2020 | Fine et al. |
| 2020/0139073 A1 | 5/2020 | Rector et al. |
| 2020/0163989 A1 | 5/2020 | Montgomery et al. |
| 2020/0171259 A1 | 6/2020 | Flanagan et al. |
| 2020/0171264 A1 | 6/2020 | Goldstein et al. |
| 2020/0180958 A1 | 6/2020 | Fine et al. |
| 2020/0282375 A1 | 9/2020 | Fine et al. |
| 2020/0360649 A1 | 11/2020 | Hall et al. |
| 2020/0361772 A1 | 11/2020 | Hall et al. |
| 2020/0361773 A1 | 11/2020 | Gillerman et al. |
| 2020/0390994 A1 | 12/2020 | Gillerman et al. |

FOREIGN PATENT DOCUMENTS

| | | | | |
|---|---|---|---|---|
| CN | 201037113 Y | 3/2008 | | |
| CN | 100404083 C | 7/2008 | | |
| CN | 101036482 B | 12/2010 | | |
| CN | 110872714 A | 3/2020 | | |
| DE | 10151270 A1 | 10/2006 | | |
| EP | 621051 | 10/1994 | | |
| EP | 0763500 A2 | 3/1997 | | |
| EP | 1036758 | 9/2000 | | |
| EP | 2151554 | 2/2010 | | |
| EP | 1854494 | 6/2012 | | |
| JP | H04132560 | 5/1992 | | |
| JP | 2000102616 | 4/2000 | | |
| JP | 2004065636 A | 3/2004 | | |
| JP | 2006273677 | 10/2006 | | |
| KR | 20100087977 A | 8/2010 | | |
| RU | 2199167 C1 | 2/2003 | | |
| WO | 199507610 A1 | 3/1995 | | |
| WO | WO2004032719 | 4/2004 | | |
| WO | 2005110441 A2 | 11/2005 | | |
| WO | WO2009018837 | 2/2009 | | |
| WO | 2010021944 A1 | 2/2010 | | |
| WO | WO2011/002606 | 1/2011 | | |
| WO | 2012034089 A1 | 3/2012 | | |
| WO | WO2012/094008 | 7/2012 | | |
| WO | WO2013/052548 | 4/2013 | | |
| WO | WO2013/070712 | 5/2013 | | |
| WO | WO2013/181179 | 12/2013 | | |
| WO | WO2014/085719 | 6/2014 | | |
| WO | WO2014/143842 | 9/2014 | | |
| WO | WO2014/144151 | 9/2014 | | |
| WO | WO2015/066278 | 5/2015 | | |
| WO | WO2015/127085 | 8/2015 | | |
| WO | WO2016/064863 | 4/2016 | | |
| WO | WO-2016064863 A1 * | 4/2016 | ......... | A61M 16/009 |
| WO | WO2018/157172 | 8/2018 | | |
| WO | WO2018/157175 | 8/2018 | | |
| WO | 2019046415 A1 | 3/2019 | | |
| WO | WO2019/046413 | 3/2019 | | |
| WO | WO2019/133776 | 7/2019 | | |
| WO | WO2019/133777 | 7/2019 | | |
| WO | 2019222640 A1 | 11/2019 | | |
| WO | 2020033768 A1 | 2/2020 | | |
| WO | 2020142658 A1 | 7/2020 | | |
| WO | 2020150195 A1 | 7/2020 | | |
| WO | 2020232414 A1 | 11/2020 | | |
| WO | 2020232419 A1 | 11/2020 | | |

OTHER PUBLICATIONS

Fowler, "Exercise Intolerance in Pulmonary Arterial Hypertension", Pulmonary Medicine, vol. 2012, Article ID 39204, 11 pages, (2012).
Keshav, Saurabh. "Using Plasmas for High-speed Flow Control and Combustion Control" Diss. The Ohio State University, 2008.
Li et al., Production of Medically Useful Nitric Monoxide Using AC Arc Discharge, Nitric Oxide, Feb. 28, 2018, vol. 73, pp. 89-95.
Mok et al. "Application of Positive Pulsed Corona Discharge to Removal of SO2 and NOx," Proceedings, ICESP VII, Sep. 20-25, 1998, Kyongiu, Korea.
Namihira et al., Production of Nitric Oxide Using a Pulsed Arc Discharge, IEEE Transactions on Plasma Science, 2002, 30(5):1993-1998.
Namihira et al., Production of Nitric Monoxide Using Pulsed Discharges for a Medical Application, IEEE Transactions on Plasma Science, vol. 29, No. 1, pp. 109-114, Feb. 2000.
Schilz, "Treatment of Pulmonary Hypertension Related to Disorders of Hypoxia" Advances in Pulmonary Hypertension, vol. 4, No. 2, pp. 14-22, May 2005.
PCT International Search Report and Written Opinion in PCT/US2018/020056 dated Apr. 19, 2018.
PCT International Search Report and Written Opinion in PCT/US2018/020060 dated Apr. 23, 2018.
Arjunan Thesis—Plasma Produced Reactive Oxygen and Nitrogen Species in Angiogenesis—May, 2011—Krishna Priya Arjunan.
Arora et al., Nitric Oxide Regulation of Bacterial Biofilms, Biochemistry, vol. 54, pp. 3717-3728, May 21, 2015.
Barraud et al., Involvement of Nitric Oxide n Biofilm Dispersal of Pseudomonas Aeruginosa, Journal of Bacteriology, vol. 188, No. 21, pp. 7344-7353, Nov. 2006.
Bentur et al., Pilot Study to Test Inhaled Nitric Oxide in Cystic Fibrosis Patients with Refractory Mycobacterium Abscessus Lung Infection, Journal of Cystic Fibrosis, vol. 19, pp. 225-231, May 23, 2019.
Bogdonovski et al., Anti-Mycobacterial Activity of High-Dose Nitric Oxide Against Mycobacterium Abscessus In Vitro, National Institutes of Health Poster, Jul. 8, 2018.
Deppisch et al., Gaseous Nitric Oxide to Treat Antibiotic Resistant Bacterial and Fungal Lung Infections in Patients with Cystic Fibrosis: A Phase I Clinical Study, Infection, vol. 44, pp. 513-520, Feb. 9, 2016.

(56) References Cited

OTHER PUBLICATIONS

Dobrynin et al. "Direct and Controllable Nitric Oxide Delivery into Biological Media and Living Cells by a Pin-to-Hole Spark Discharge (PHD) Plasma" Journal of Physics D: Applied Physics, vol. 44, pp. 1-10, Jan. 28, 2011.
Howlin et al., Low-Dose Nitric Oxide as Targeted Anti-Biofilm Adjunctive Therapy to Treat Chronic Pseudomonas Aeruginosa Infection in Cystic Fibrosis, Molecular Therapy, vol. 25, No. 9, pp. 2104-2116, Sep. 2017.
Hu et al., "Study on Production of Inhaled Nitric Oxide for Medical Applications by Pulsed Discharge" IEEE Transactions on Plasma Science, vol. 35, No. 3, pp. 619-625, Jun. 2007.
Kuo, Spencer P. "Air Plasma for Medical Applications" J. Biomedical Science and Engineering, vol. 5, pp. 481-495, Sep. 2012.
McMullin et al., The Antimicrobial Effect of Nitric Oxide on the Bacteria That Cause Nosocomial Pneumonia in Mechanically Ventilated Patients in the Intensive Care Unit, Respiratory Care, vol. 50, No. 11, pp. 1451-1456, Nov. 2005.
Miller et al., Gaseous Nitric Oxide Bactericidal Activity Retained During Intermittent High-Dose Short Duration Exposure, Nitric Oxide, vol. 20, Issue 1, pp. 16-23, Feb. 2009.
Miller et al., Inhaled Nitric Oxide Decreases the Bacterial Load in a Rat Model of Pseudomonas Aeruginosa Pneumonia, Journal of Cystic Fibrosis, vol. 12, pp. 817-820, Mar. 6, 2013.
Miller et al., Nitric Oxide is a Potential Antimicrobial Against Slow and Fast Growing Mycobacteria, Online Abstracts Issue, American Journal Respiratory Care Medicine, vol. 193, A7498, May 18, 2016.
Miller et al., A Phase I Clinical Study of Inhaled Nitric Oxide in Healthy Adults, Journal of Cystic Fibrosis, vol. 11, pp. 324-331, Apr. 18, 2012.
Namihira et al., "Temperature and Nitric Oxide Generation in a Pulsed Arc Discharge Plasma" Plasma Science and Technology, vol. 9, No. 6, pp. 747-751, Dec. 2007.
Navarro-Gonzalez et al., "The Physical Mechanism of Nitric Oxide Formation in Simulated Lightning" Geophysical Research Letters, vol. 28, No. 20, pp. 3867-3870, Oct. 15, 2001.
Olivier et al., Treatment of Refractory Mycobacterium Abscessus Lung Infection with Inhaled Intermittent Nitric Oxide, Poster, Jul. 8, 2018.
Sakai et al., "Nitric Oxide Generator Based on Pulsed Arc Discharge" Acta Physica Polonica A, vol. 115, No. 6, pp. 1104-1106, Jun. 2009.
Tal et al., Nitric Oxide Inhalations in Bronchiolitis: A Pilot, Randomized, Double-Blinded, Controlled Trial, Pediatric Pulmonology, vol. 53, Issue 1, pp. 95-102, Jan. 2018.
Yaacoby-Bianu et al., Compassionate Nitric Oxide Adjuvant Treatment of Persistent Mycobacterium Infection in Cystic Fibrosis Patients, The Pediatric Infectious Disease Journal, vol. 37, No. 4, Apr. 2018.
Charles, et al., "S102 Deposition from Oxygen/Silane Pulsed Helicon Diffusion Plasmas" Applied Physics Letters, vol. 67, No. 1, pp. 40-42, Jul. 3, 1995.
Heli, Study on the Removal of Byproduct Nitrogen Dioxide from the Mixture of Inhaled Nitric Oxide Produced by Pulsed Arc Discharge, Thesis for Degree of Master of Engineering, Huazhong University of Science & Technology, China, Apr. 2006, 78 pages (Includes English Language Translation of Title Page and Abstract).
Hui, Research on the Production of Nitric Oxide by Pulsed Arc Cischarge and the Curing of Respiratory Distress Instrument, Dissertation for Degree of Doctor of Philosophy in Engineering, Huazhong University of Science and Technology, China, Apr. 2005, 138 pages (Includes English Language Translation of Title Page and Abstract).
Patil et al., Plasma Assisted Nitrogen Oxide Production from Air, AiChE Journal, vol. 64, Issue 2, Aug. 14, 2017.
Pawlat et al., Evaluation of Oxidative Species in Gaseous, Plasma Chemistry and Plasma Processing, vol. 39, pp. 627-642, Mar. 28, 2019.
Wang et al., "Gliding Arc Plasma for CO2 Conversion: better insights by a combined experimental and modelling approach", Chemical Engineering Journal, vol. 330, pp. 11-25, Jul. 21, 2017.
Birkeland, K., "On the Oxidation of Atmospheric Nitrogen in Electric Arcs", A Paper read before the Faraday Society on Monday, Jul. 2, 1906, Published on Jan. 1, 1906.
Feigerle, C., et al., "Multiphoton Ionization of Vibrationally Hot Nitric Oxide Produced in a Pulsed Supersonic Glow Discharge", Journal of Chemical Physics, vol. 90, Issue 6, pp. 2900-2908, Mar. 15, 1989.
Hu, Hui et al., "Study on Pulsed Arc Discharge Conditions on Production of Nitric Oxide for Medical Application", High Voltage Apparatus, Issue 3, Mar. 2005.
Hu, Hui et al., "Study on Production of Nitric Monoxide for Respiratory Distress by Pulsed Discharge", Proceedings of the CSEE, vol. 23, No. 2, Jan. 2005.
Hu, Hui et al., "The Effect of Flow Distribution on the Concentration of NO Produced by Pulsed Arc Discharge", Plasma Science and Technology, vol. 9, No. 6, pp. 766-769, Dec. 2007.
Johns Hopkins University—"American Chemical Journal vol. XXXV"—No. 4, Reports Chapter, pp. 358-368, Apr. 1906.
Komev, J., et al., "Generation of Active Oxidant Species by Pulsed Dielectric Barrier Discharge in Water-Air Mixtures", Ozone: Science & Engineering, vol. 28, Issue 4, pp. 207-215, Jul. 2006.
Li, Z. et al., "Development of Miniature Pulsed Power Generator," 2005 IEEE Pulsed Power Conference, Monterey, CA, pp. 1053-1056, Jul. 2005.
Matsuo, K. et al., "Nitric Oxide Generated by Atmospheric Pressure Air Microplasma," 2009 IEEE Pulsed Power Conference, Washington, DC, Jun. 28-Jul. 2, 2009, pp. 999-1003, Jan. 19, 2010.
Namihara et al., "Production of NO Using Pulsed Arc Discharges and Its Medical Applications", Journal of Plasma and Fusion Research, vol. 79, No. 1 pp. 35-38, Jun. 25, 2002.
Namihira et al., "Production of Nitric Monoxide in Dry Air Using Pulsed Discharge," Digest of Technical Papers. 12th IEEE International Pulsed Power Conference. (Cat. No. 99CH36358), Monterey, CA, pp. 1313-1316 vol. 2, Aug. 6, 2002.
Overzet, et al. "Why and How to Pulse a Plasma"—slide show presentation, Oct. 1997.
Pontiga, F., et al., "Nitrogen Oxides Generation Induced by Negative Corona Discharge in N2 + 02 Mixtures," 2006 IEEE Conference on Electrical Insulation and Dielectric Phenomena, Kansas City, MO, pp. 264-267, Oct. 2006.
Sakai, et al., "A Compact Nitric Oxide Supply for Medical Application," 2007 16th IEEE International Pulsed Power Conference, Albuquerque, NM, pp. 752-755, Oct. 14, 2008.

\* cited by examiner

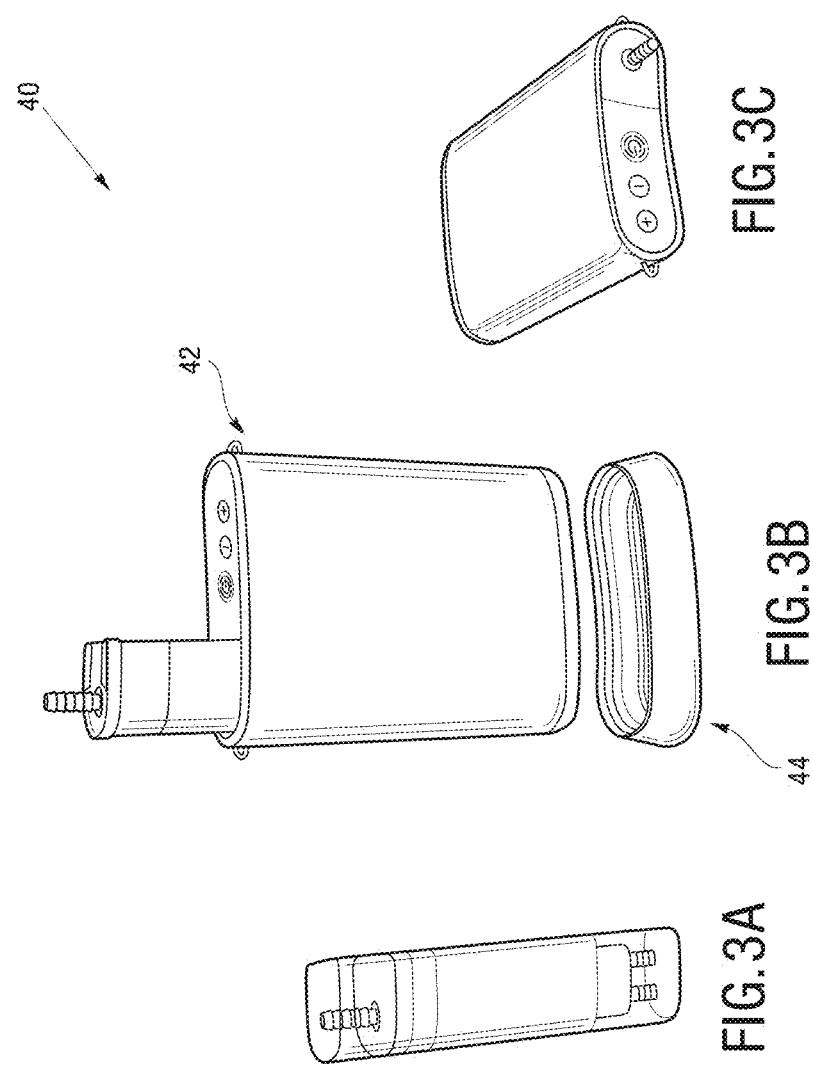

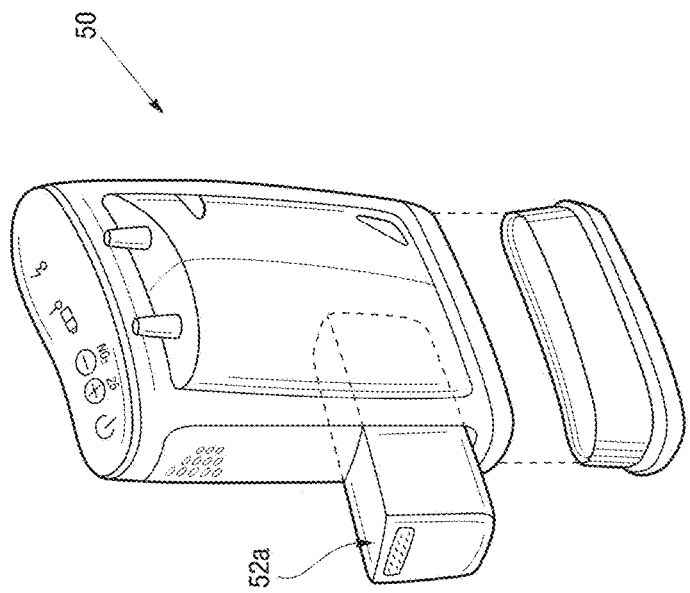
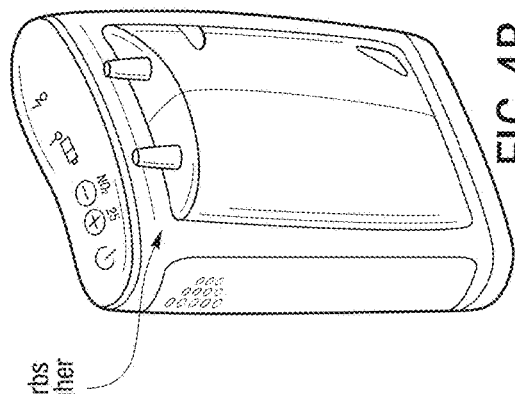
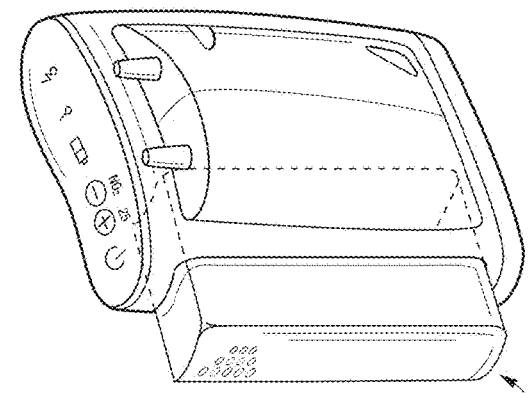
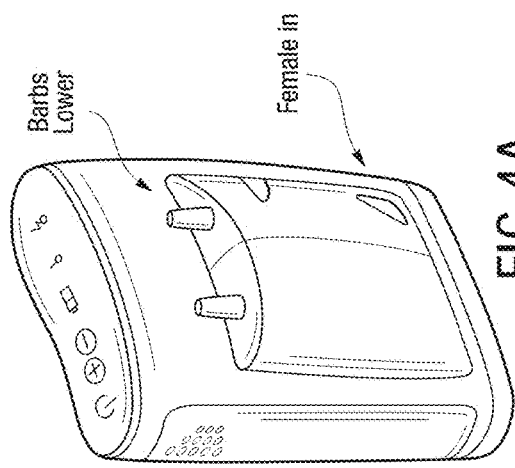
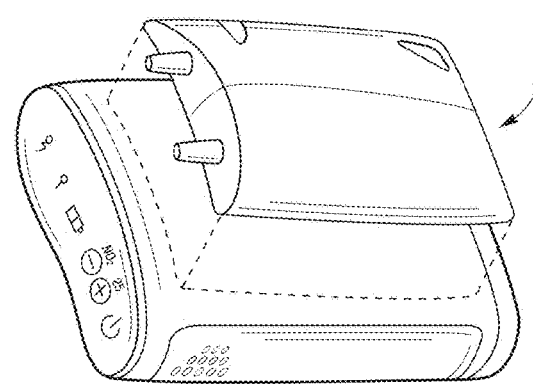

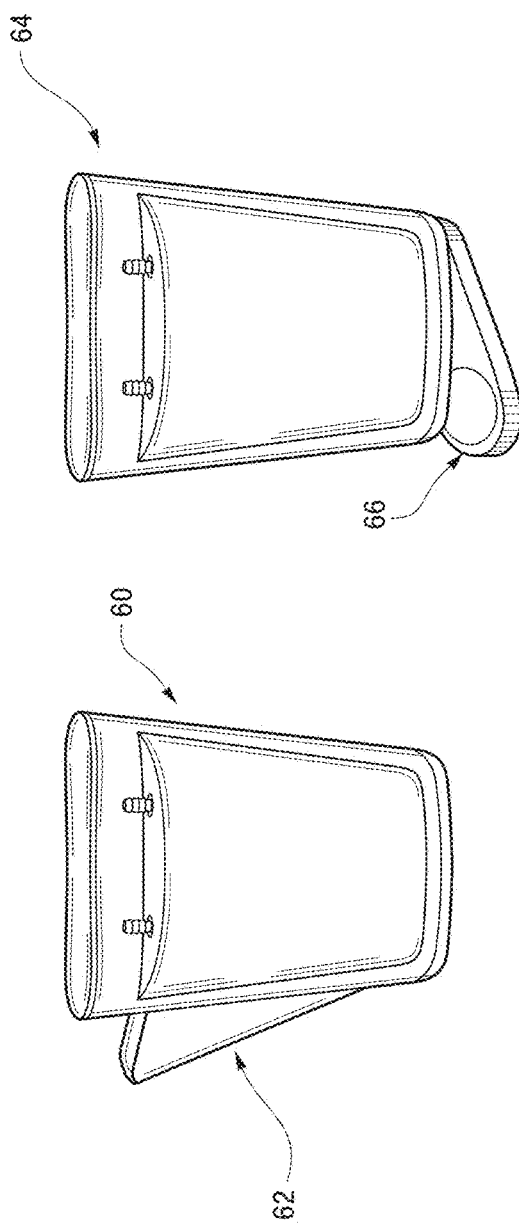
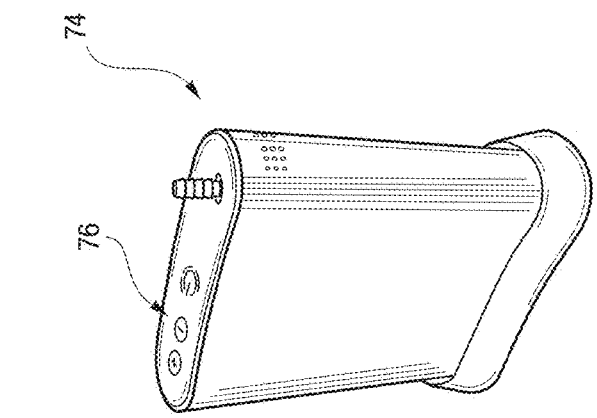
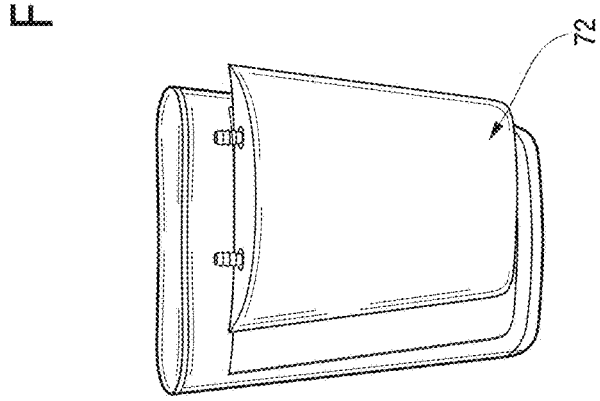
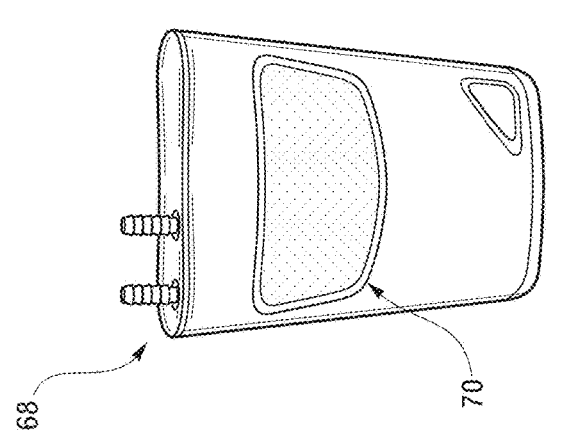

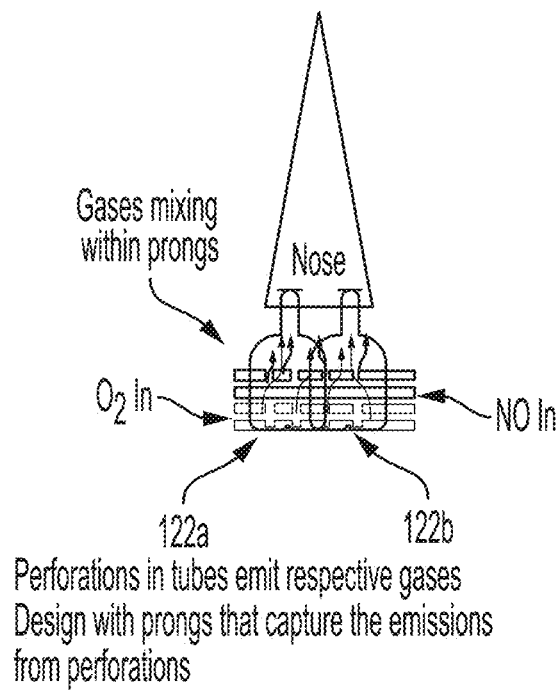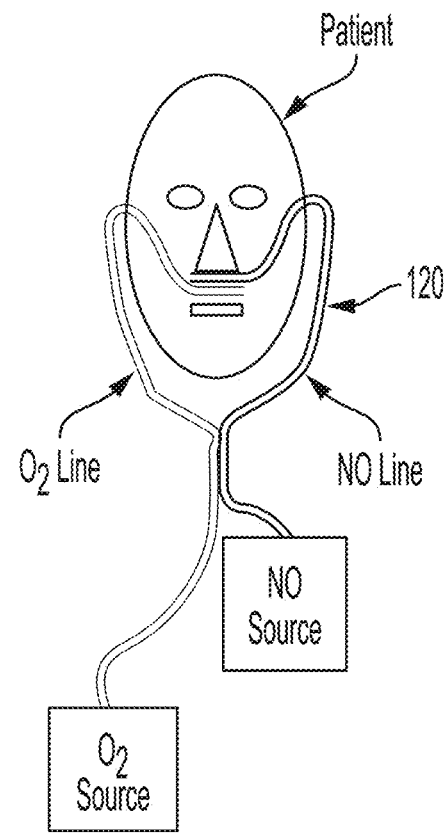

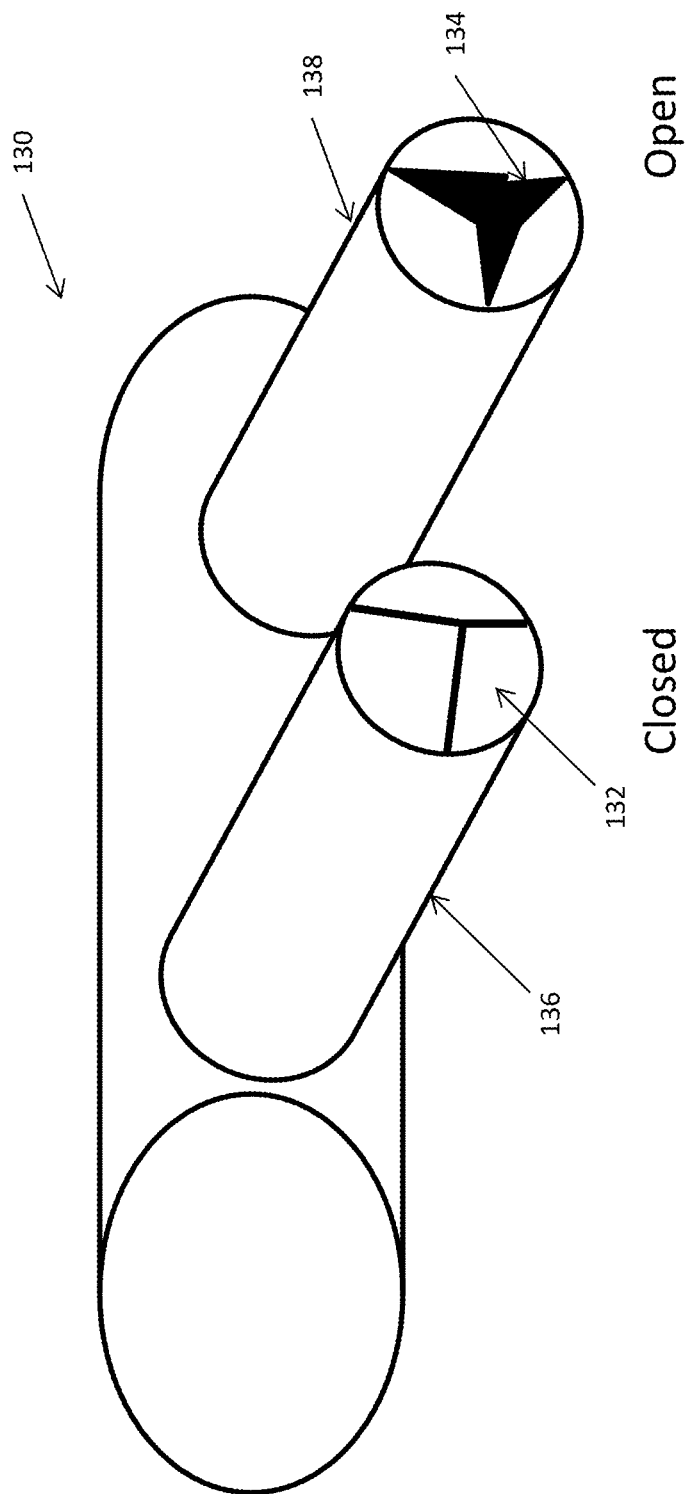

160

162

164

166

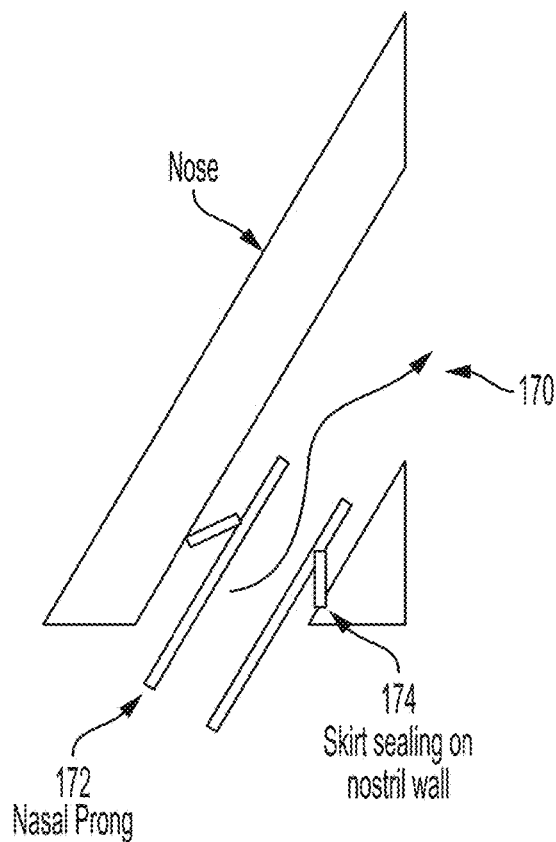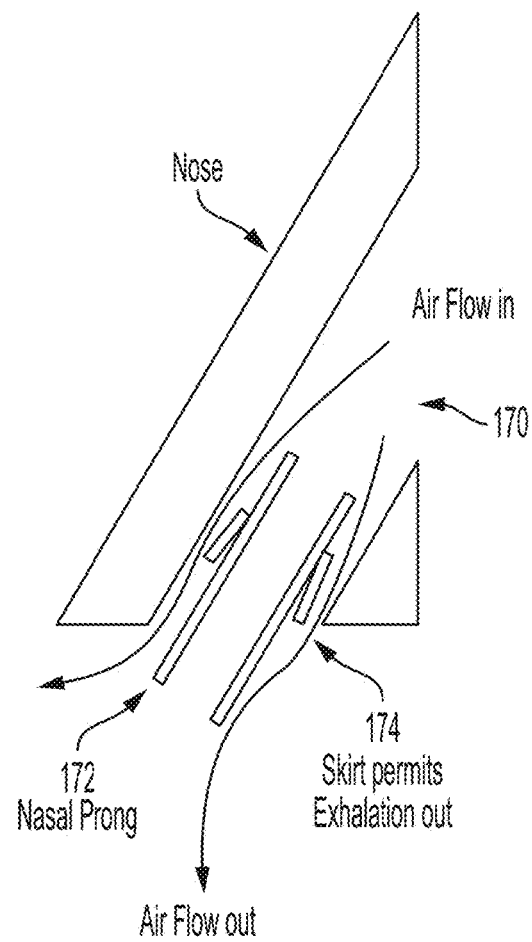

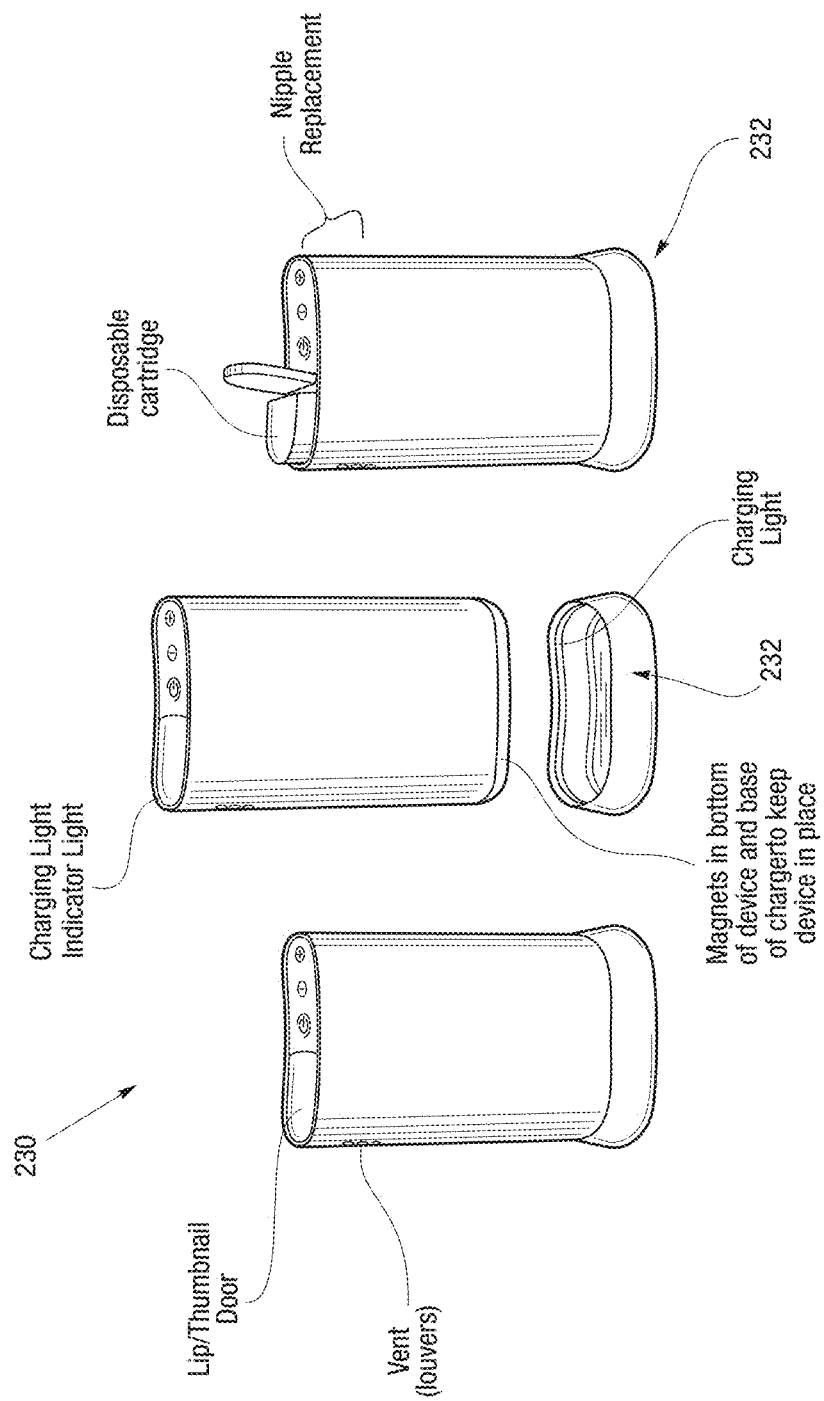

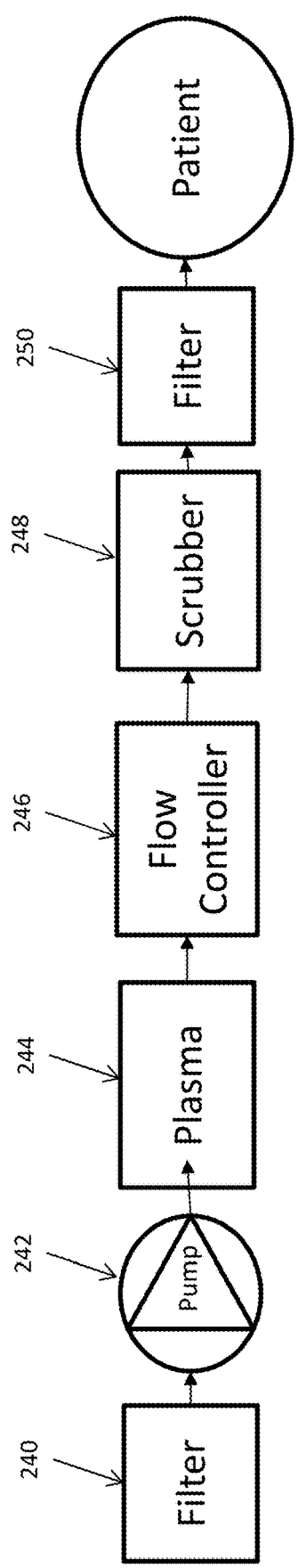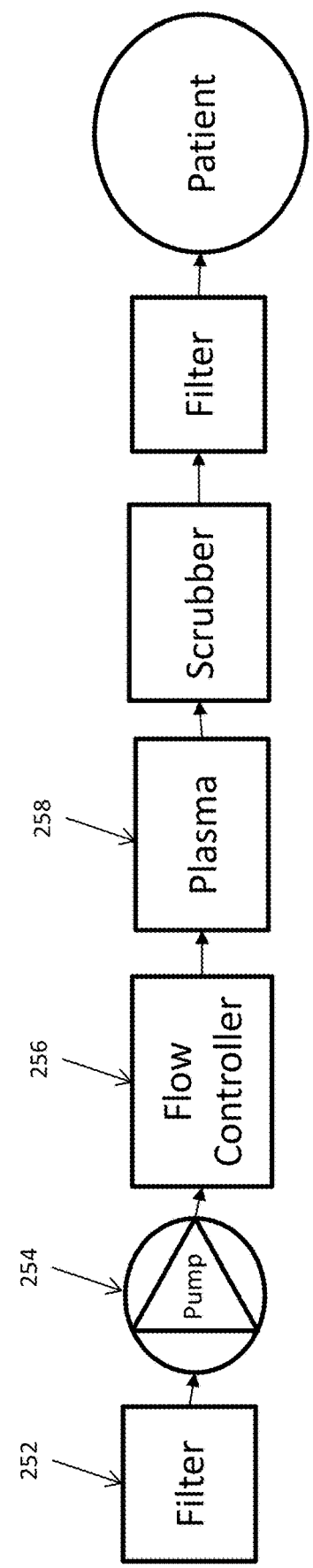

| Flow Level | Valve 1 | Valve 2 |
|---|---|---|
| 1 | Closed | Closed |
| 2 | Open | Closed |
| 3 | Closed | Open |
| 4 | Open | Open |

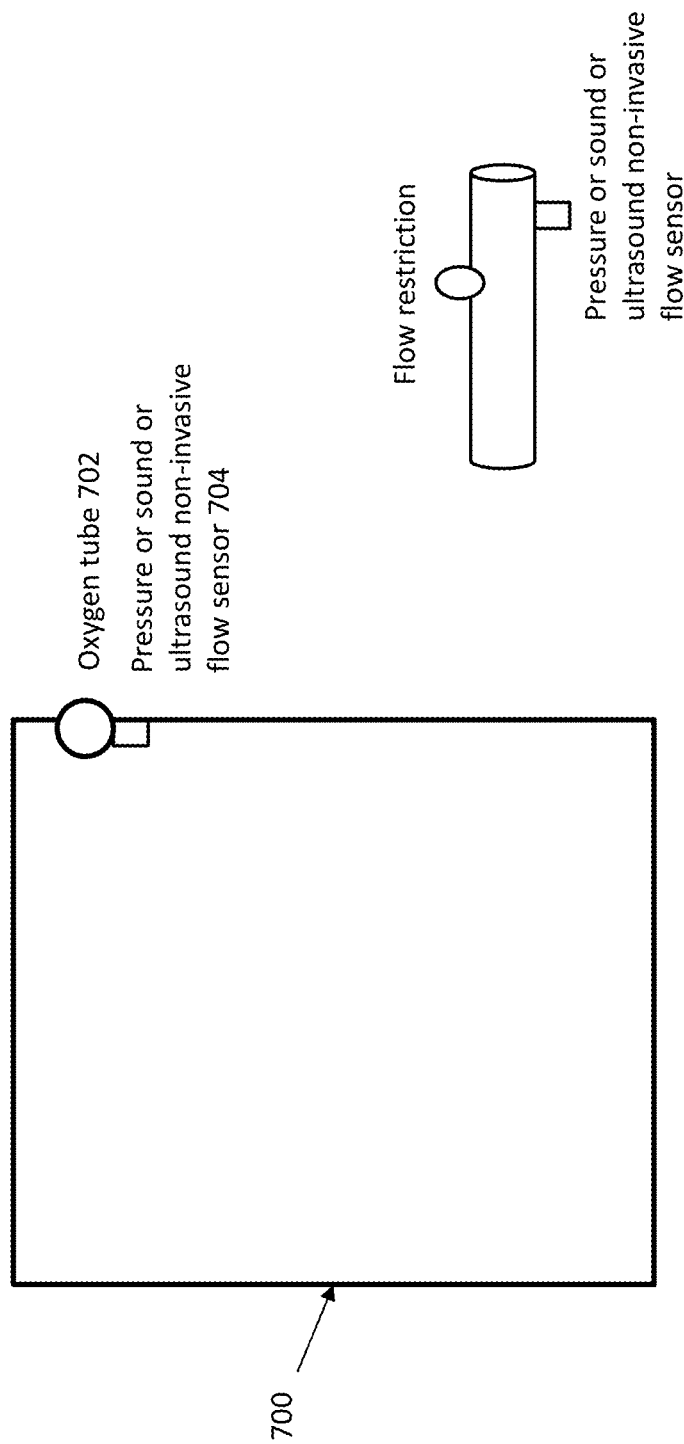

End view showing clips grasping the ground end

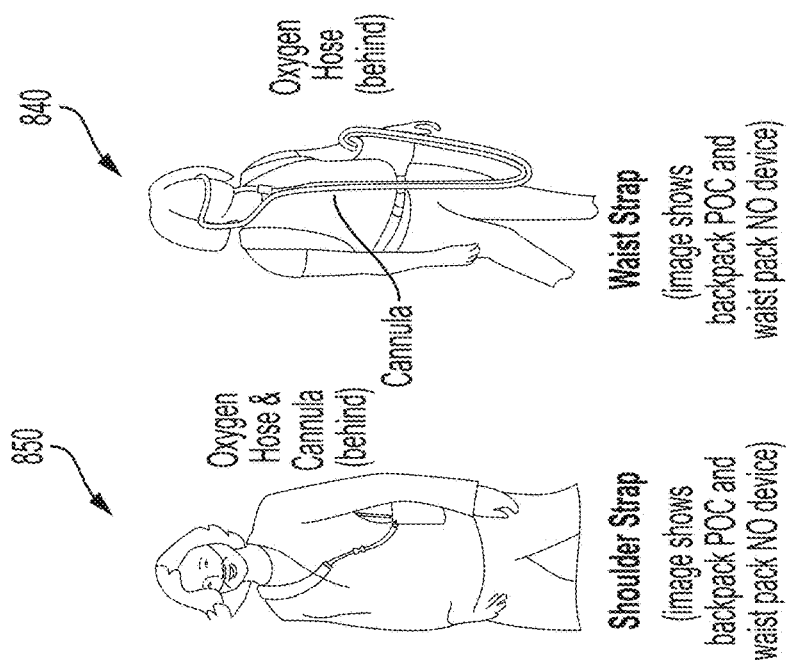
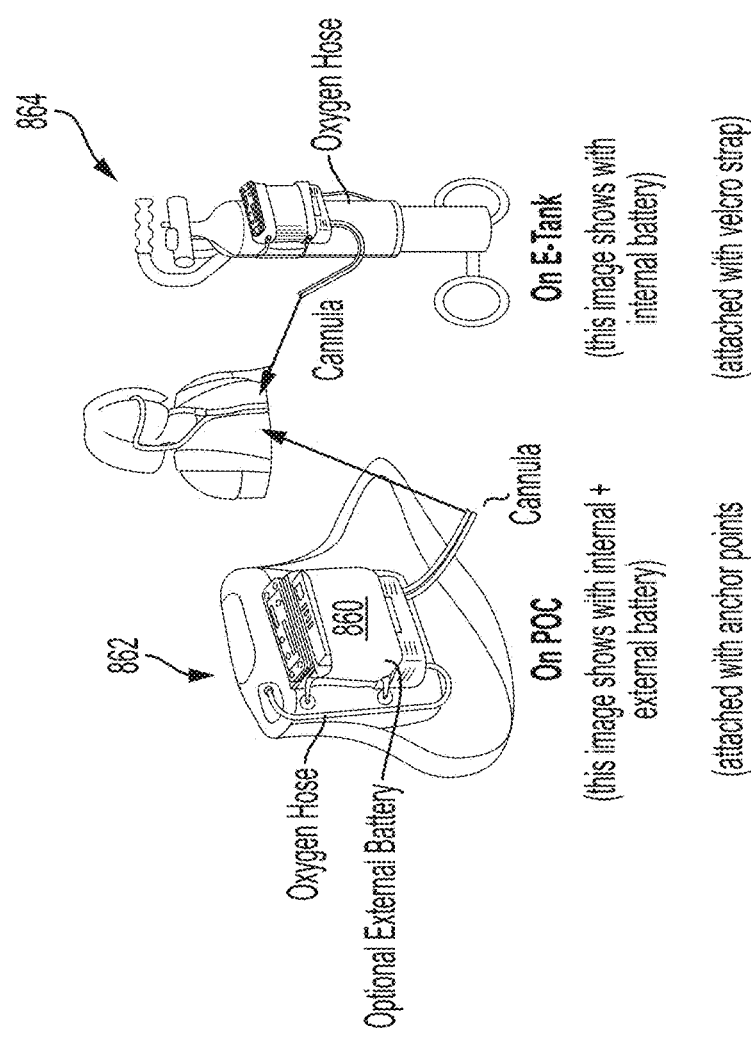
FIG. 62A  FIG. 62B  FIG. 62C  FIG. 62D

SYSTEMS AND METHODS FOR AMBULATORY GENERATION OF NITRIC OXIDE

RELATED APPLICATIONS

This application is a continuation patent application of U.S. application Ser. No. 16/363,505 filed Mar. 25, 2019, which is a continuation of U.S. application Ser. No. 15/907,258 filed Feb. 27, 2018, now U.S. Pat. No. 10,328,228, which claims the benefit of and priority to U.S. Provisional Application No. 62/463,943 filed Feb. 27, 2017, U.S. Provisional Application No. 62/463,956 filed Feb. 27, 2017, U.S. Provisional Application No. 62/509,394 filed May 22, 2017, U.S. Provisional Application No. 62/553,572 filed Sep. 1, 2017, U.S. Provisional Application No. 62/574,173 filed Oct. 18, 2017, and U.S. Provisional Application No. 62/614,492 filed Jan. 7, 2018, and the contents of each of these applications are hereby incorporated herein by reference in their entireties.

FEDERALLY SPONSORED RESEARCH OR DEVELOPMENT

This invention was made with government support under Grant No. R44 TR001704, awarded by the National Institutes of Health (NIH). The government has certain rights in the invention.

FIELD

The present disclosure relates to systems and methods for generating nitric oxide for use with a ventilation device.

BACKGROUND

Nitric oxide has found to be useful in a number of ways for treatment of disease, particularly cardiac and respiratory ailments. Previous systems for producing NO and delivering the NO gas to a patient have a number of disadvantages. For example, tank-based systems require large tanks of NO gas at a high concentration and are required to purge with NO when treatment is resumed. Synthesizing NO from $NO_2$ or $N_2O_4$ requires the handling of toxic chemicals. Prior electric generation systems involve generating plasma in the main flow of air to be delivered to patients, and generate unsafe quantities of $NO_2$ or $O_3$.

SUMMARY

The present disclosure is directed to systems, methods and devices for portable nitric oxide generation and delivery for use both in and out of the hospital.

A wearable nitric oxide generation system is provided and in some embodiments comprises a housing configured to be wearable, and a reactant gas flow path located in the housing. The reactant gas flow path is configured to provide release of a pressurized reactant gas at specific flow rates to one or more plasma chambers. One or more electrodes are located in the one or more plasma chambers and are configured to generate a product gas containing nitric oxide using a flow of the reactant gas through the one or more plasma chambers. A controller is configured to regulate the amount of nitric oxide generated in the reactant gas, and disposable cartridge including one or more scavenger paths is configured to remove $NO_2$ from the product gas generated by the one or more plasma chambers. A connector to deliver the product gas to a patient delivery device is also provided.

In some embodiments, the disposable cartridge includes an inlet filter, an exhaust scavenger, and/or one or more exhaust filters. In some embodiments, the system also includes one or more filters positioned to receive NO-enriched air from the one or more scavenger paths and configured to filter the NO-enriched air. In some embodiments, the patient delivery device is selected from a group consisting of a nasal cannula, a tube located near an ear, and a tube in communication with a trachea.

In some embodiments, the system is used with a device selected from a group consisting of a resuscitation instrument, a ventilator, a defibrillator, a ventricular assist device (VAD), a Continuous Positive Airway Pressure (CPAP) system, a Bilevel Positive Airway Pressure (BiPAP) system, a non-invasive positive pressure ventilator (NIPPV), a heated high-flow nasal cannula application, a nebulizer, an extracorporeal membrane oxygenation (ECMO); a cardiopulmonary bypass system, an automated CPR system, an oxygen delivery system, an oxygen concentrator system, an oxygen generation system, and/or an automated external defibrillator (AED) In some embodiments, the system is used with an oxygen generator or an oxygen concentrator to increase nitric oxide production.

In some embodiments, the controller is configured to control the shape of an AC waveform by controlling a frequency and a duty cycle. In some embodiments, the controller measures a resonant frequency of a high voltage circuit and controls a frequency and a duty cycle of an AC waveform to maximize excitation of the high voltage circuit. In some embodiments, the resonant frequency is determined throughout a service life of the system to accommodate changes in environmental conditions, system wear, and/or manufacturing variance. In some embodiments, the resonant frequency is automatically determined at a power-up of the system. In some embodiments, the resonant frequency is automatically determined at the beginning of each patient treatment. In some embodiments, the resonance frequency is stored in memory between uses so that a resonance search is not required at power-up of the system.

In some embodiments, the user interface allows a user to interact with the system, view information about the system and nitric oxide production, and control parameters related to nitric oxide production. In some embodiments, the user interface includes illuminated indicators for alarm status, battery charge status, external power connection, cartridge remaining life, $O_2$ flow detection, GSM connection, and/or NO generation.

In some embodiments, the system also includes a microphone to receive user voice inputs. In some embodiments, the system also includes one or more antennae for GSM, Bluetooth, WiFi and/or other connectivity. In some embodiments, the system also includes a reactant gas source in the form of a reservoir in fluid communication with the one or more plasma chambers. In some embodiments, the reactant gas source is a pump. In some embodiments, the system is portable for use outside a hospital.

In some embodiments, a wearable nitric oxide generation system is provided and comprises a reactant flow path configured to provide release of a pressurized reactant gas at specific flow rates to one or more plasma chambers, and one or more electrodes located in the one or more plasma chambers configured to generate a product gas containing nitric oxide using a flow of the reactant gas through the one or more plasma chambers. A controller is configured to regulate the amount of nitric oxide generated in the reactant gas. The controller measures a resonant frequency of a high voltage circuit and controls a frequency and a duty cycle of an AC waveform to maximize excitation of the high voltage circuit. A disposable cartridge includes one or more scavenger paths configured to remove $NO_2$ from the product gas generated by the one or more plasma chambers. A connector to deliver the product gas to a patient delivery device is also provided.

In some embodiments, the system is integrated with a device selected from a group consisting of resuscitation instrument, a ventilator, a defibrillator, a ventricular assist device (VAD), a Continuous Positive Airway Pressure (CPAP) system, a Bilevel Positive Airway Pressure (BiPAP) system, a non-invasive positive pressure ventilator (NIPPV), a heated high-flow nasal cannula application, a nebulizer, an extracorporeal membrane oxygenation (ECMO); a cardiopulmonary bypass system, an automated CPR system, an oxygen delivery system, an oxygen concentrator system, an oxygen generation system, and an automated external defibrillator (AED). In some embodiments, the system is portable for use outside a hospital.

In some embodiments, a wearable nitric oxide generation system is provided that comprises a reactant gas flow path configured to provide release of a pressurized reactant gas at specific flow rates to one or more plasma chambers, one or more electrodes located in the one or more plasma chambers configured to generate a product gas containing nitric oxide using a flow of the reactant gas through the one or more plasma chambers, and a controller configured to regulate the amount of nitric oxide generated in the reactant gas. A disposable cartridge includes one or more scavenger paths configured to remove $NO_2$ from the product gas generated by the one or more plasma chambers, and an oxygen generator or an oxygen concentrator is used to increase nitric oxide production. A connector to deliver the product gas to a patient delivery device is provided.

In some embodiments, the system is integrated with a device selected from a group consisting of resuscitation instrument, a ventilator, a defibrillator, a ventricular assist device (VAD), a Continuous Positive Airway Pressure (CPAP) system, a Bilevel Positive Airway Pressure (BiPAP) system, a non-invasive positive pressure ventilator (NIPPV), a heated high-flow nasal cannula application, a nebulizer, an extracorporeal membrane oxygenation (ECMO); a cardiopulmonary bypass system, an automated CPR system, and an automated external defibrillator (AED). In some embodiments, the system is portable for use outside a hospital.

A method for generating NO with a portable, wearable system is also provided, and includes providing a reactant gas flow path located in a wearable housing. The reactant gas flow path releases a pressurized reactant gas at specific flow rates to one or more plasma chambers. The method also includes generating a product gas containing nitric oxide using a flow of the reactant gas through the one or more plasma chambers using one or more electrodes that are located in the one or more plasma chambers. A controller regulates the amount of nitric oxide generated in the reactant gas, and disposable cartridge including one or more scavenger paths removes $NO_2$ from the product gas generated by the one or more plasma chambers. The product gas is delivered to a patient delivery device using a connector.

In some embodiments, the NO generation system can be integrated with other systems. In an embodiment, patients that have left or right heart failure can receive a ventricular assist device (VAD) to provide assistance in pumping blood, and a NO generation system can be used in conjunction with or integrated with a VAD system to decrease the effort to pump blood through the lungs. This reduced pumping effort can decrease the size of the VAD, VAD battery requirements, and improve patient oxygenation. In an embodiment, an NO generation device can be used with an AED People suffering from cardiac arrest suffer from oxygen deprivation in their tissues including heart (Myocardial infarction or heart attack) and brain (stroke). NO administration during CPR can increase blood oxygenation, thereby improving the potential for the heart to restart beating when defibrillated or restart on its own. An NO generation device can be constructed as a subsystem within or augment resuscitation instrumentation (e.g. defibrillator, AED, ventilator, manual resuscitation bag, manual chest compression device, automated chest compression device). In an embodiment, an NO generation system can be used as a diagnostic tool in a catheter lab for testing vasoreactivity. In an embodiment, an NO generation system could be used in conjunction with CPR to improve oxygenation of the blood. For example, the NO generation system can be integrated into an automatic CPR system, sharing the same battery, user display, alarm system, speaker and microprocessor. In an embodiment, an NO generation system can be designed to work with manual CPR whereby the device can detect passive respiration as a result of chest compression and supplement inhaled air with NO. In an embodiment, the device can resemble a safety barrier for mouth-to-mouth resuscitation, serving as a physical barrier between mouths to prevent the spread of disease whilst supplementing gas flowing to the patient with NO. The device can generate NO when the rescuer breathes into the patient by detecting the presence of the rescuer and or air flow directed at the patient. In an embodiment, an NO generation system can be used for patient activity, rather than continuously. For example, the NO generation system can be used by patients with medical conditions or athletes that use the device for performance enhancement, such as mountaineers, airplane pilots, and cyclists, by improving oxygen uptake particularly in high altitudes. In an embodiment, an NO generator can also be used in conjunction with or integrated into a ventilator or a system that delivers Continuous Positive Airway Pressure (CPAP) and Bilevel Positive Airway Pressure (BiPAP) to improve oxygen uptake. In an embodiment, an NO generation system can be used with or integrated into a non-invasive positive pressure ventilator (NIPPV) and/or a heated high-flow nasal cannula application. In an embodiment, an NO generation system can be used in conjunction with or integrated into a nebulizer to increase improve oxygen uptake and drug absorption. In an embodiment, an NO generation system may be used in conjunction with extracorporeal membrane oxygenation (ECMO) or cardio-pulmonary bypass to reduce the need for anticoagulants (e.g. heparin).

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 3A, FIG. 3B, and FIG. 3C illustrate an embodiment of an ambulatory, portable NO generation system;

FIG. 4A, FIG. 4B, FIG. 4C, FIG. 4D, and FIG. 4E are multiple views of an embodiment of an ambulatory NO generation device;

FIG. 5A is an embodiment of an ambulatory NO generation device having a scavenger cartridge located in the side of the device;

FIG. 5B is an embodiment of an ambulatory NO generation device having a scavenger cartridge located in the bottom of the device;

FIG. 5C is an embodiment of an ambulatory NO generation device having cannula and $O_2$ connections on the top of the device and a user interface on the side;

FIG. 5D is an embodiment of an ambulatory NO generation device having a scavenger on the side of the device;

FIG. 5E is an embodiment of an ambulatory NO generation device having a scavenger insertion, gas connections and user interface located on the same surface of the device;

FIG. 8C and FIG. 8D are embodiments of a nasal cannula having prongs for use with an ambulatory NO generation system;

FIG. 9 is an exemplary embodiment of a nasal cannula with tricuspid valves at the end of the nasal prongs;

FIG. 13A and FIG. 13B illustrate an embodiment of a nasal cannula prong design for use with an NO generation system;

FIG. 19A, FIG. 19B, and FIG. 19C illustrates an embodiment of an NO generation system positioned in a docking station;

FIG. 20A and FIG. 20B are embodiments of a pneumatic pathway through a wearable NO generator that can operate at higher pressure;

FIG. 51A and FIG. 51B are cross-sectional views of an embodiment of a controller enclosure;

FIG. 62A, FIG. 62B, FIG. 62C, and FIG. 62D illustrate various wearable portable NO generation devices;

Figure 1:
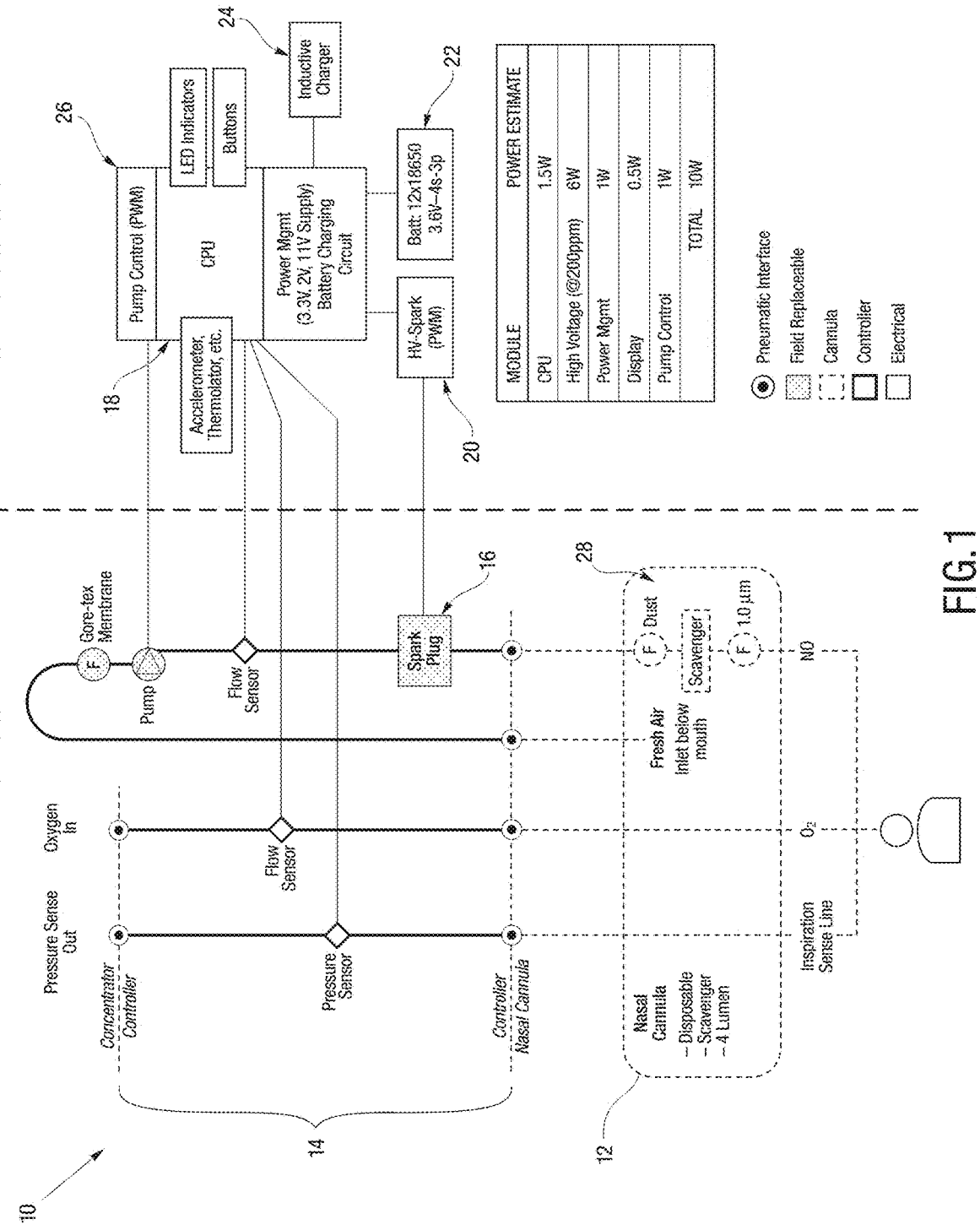
FIG. 1 is an embodiment of an ambulatory NO generation system.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments.

Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Throughout this document, the term "pump" is used to represent a component that can generate a flow and/or pressure head in a gas. Examples include but at not limited to blowers, centripetal pumps, piston pumps, diaphragm pumps, ultrasonic pumps, piezo pumps, fans, etc. Designs requiring a flow of reactant gas can also receive a flow of reactant gas from an external pressurized source, eliminating the need for an internal pump component.

Throughout this document, the term "scavenger" is used to represent a component that removes one or more of $CO_2$, $NO_2$ or $O_3$ from a gas mixture. This is also referred to interchangeably in the document as a "scrubber." Examples include but are not limited to soda lime, noXon and zeolite.

Throughout this document, the term "cannula" is used to describe a conduit for conveying NO-containing product gases from an NO generator to a patient. For the purposes of this document, other types of delivery conduits such as face masks, CPAP masks, Bi-PAP masks, Scoop catheters, single lumen trans-tracheal catheters, multi-lumen trans-tracheal catheters and the like are considered synonymous.

The present disclosure relates to systems and methods for portable and compact nitric oxide (NO) generation that can be embedded into other therapeutic devices or used alone. The portable NO generation device allows NO to be generated and delivered to a patient in any location or setting as the device is small enough to be mobile and used anywhere, including in a home of a patient or during travel. The size and portability of the ambulatory NO generation system allows a patient to use the system in a hospital or on-the-go outside a hospital and to have the benefit of NO delivery through a respiratory gas delivery device without having to be in a hospital, clinic or other medical setting. In some embodiments, an ambulatory NO generation system can be comprised of a controller and disposable cartridge. The cartridge can contain filters and/or scavengers for preparing the gas used for NO generation and/or for scrubbing and/or filtering output gases prior to patient inhalation. In some embodiments, the system can utilize an oxygen concentrator to increase nitric oxide production, reduce the rate of $NO_2$ formation and compliment oxygen generator activity as an independent device.

Figure 2:
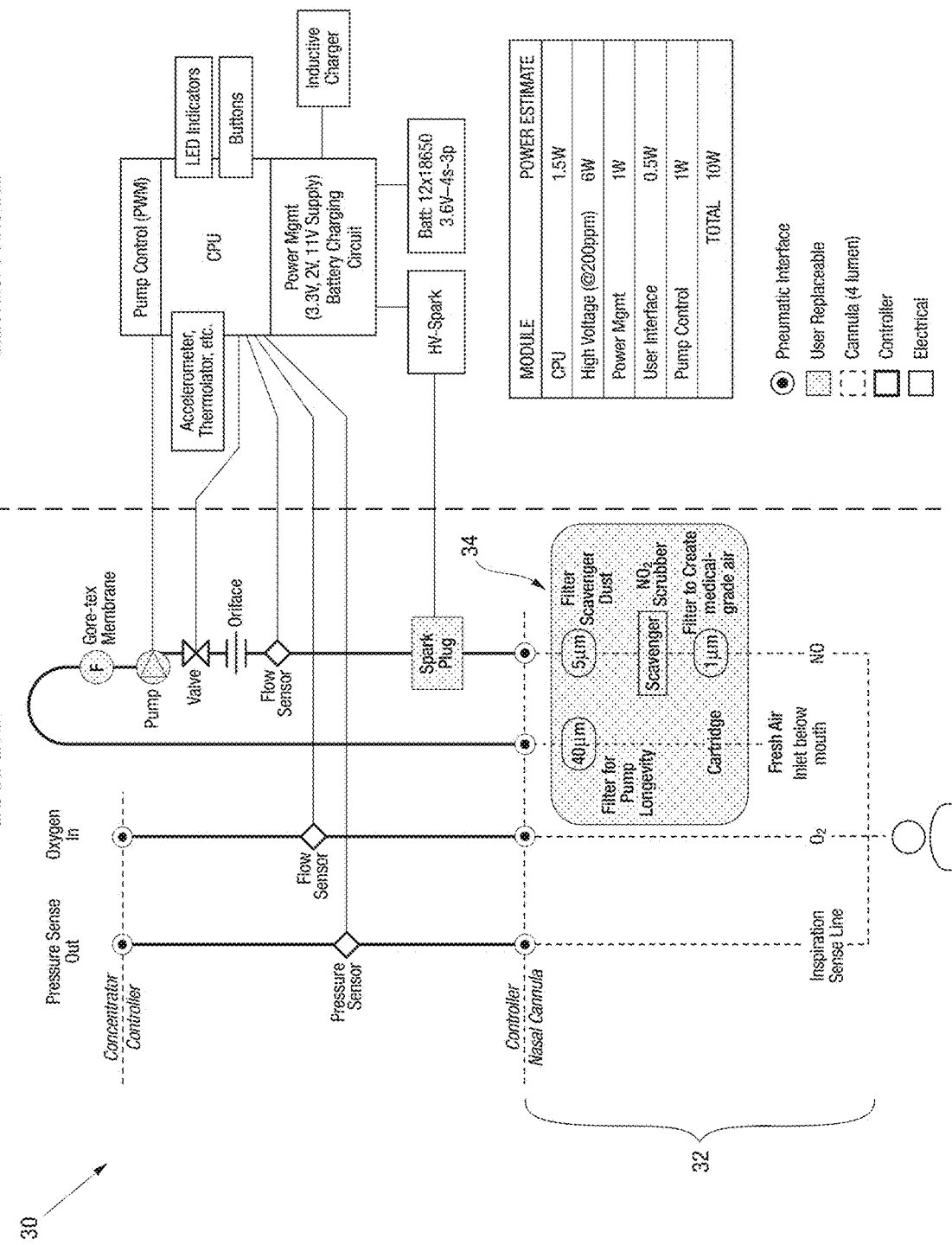
FIG. 2 is an embodiment of an ambulatory NO generation system.

FIG. 1 and FIG. 2 illustrate embodiments of ambulatory NO generation systems. FIG. 1 illustrates an embodiment of a portable ambulatory NO generation system 10 that includes a delivery device, such as a cannula 12, for delivering a product gas containing NO to a patient, that includes a filter/scavenger 28. A controller 14 is configured to control the production of NO by a plasma chamber 16 using a variety of sensors. The controller 14 includes a CPU 18 with LEDs and buttons for communication therewith by a user, a high voltage circuit 20, a power source 22, an inductive charger 24, and a pump controller 26. FIG. 2 illustrates an embodiment of a portable ambulatory NO generation system 30 that includes a delivery device, such as a cannula 32, and a disposable replaceable cartridge 34 that includes a scavenger therein.

In some embodiments, an exemplary portable NO generation system includes components for reactant gas intake and delivery to a plasma chamber. The plasma chamber includes one or more electrodes therein that are configured to produce, with the use of a high voltage circuit, a product gas containing a desired amount of NO from the reactant gas. The system includes a controller in electrical communication with the high voltage circuit and the electrodes that is configured to control the concentration of NO in the product gas using one or more control parameters relating to conditions within the system and/or conditions relating to a separate device for delivering the product gas to a patient and/or conditions relating to the patient receiving the product gas. The controller is also in communication with a user interface that allows a user to interact with the system, view information about the system and NO production, and control parameters related to NO production.

FIG. 3A, FIG. 3B, and FIG. 3C illustrate an embodiment of an ambulatory, portable NO generation system 40. The system 40 includes a controller 42 and a disposable cartridge. A base 44, or docking station can be used to hold the controller and can be configured to charge a battery of the controller.

FIG. 4A, FIG. 4B, FIG. 4C, FIG. 4D, and FIG. 4E illustrate various views of an exemplary embodiment of an ambulatory NO generation system 50. As discussed above, the system is configured to be portable and compact to allow for ease of use and transport. In some embodiments, the size and mobility of the system allows the system to be used in conjunction with other respiratory devices, or to be integrated therein. Various options for the location of a cartridge 52a, 52b, 52c are shown in FIG. 4C, FIG. 4D, and FIG. 4E, respectively.

In some embodiments, the top of the device is reserved for a user interface including buttons and display information. Cannula and oxygen connections are made on the upper edge of a bump on the side of the enclosure. A scavenger cartridge 62 can be located in several locations, including the side of a device 60 (FIG. 5A). A scavenger cartridge 66 can be location on the bottom 66 of a device 64 (FIG. 5B). In some embodiments, cannula and $O_2$ connections are on the top of a device 68, a user interface 70 is on the side (FIG. 5C), and a scavenger 72 can be on the side (FIG. 5D) or bottom. In some embodiments, the scavenger insertion, gas connections and user interface are all located on the same surface 76 of a device 74 (FIG. 5E).

Figure 6:
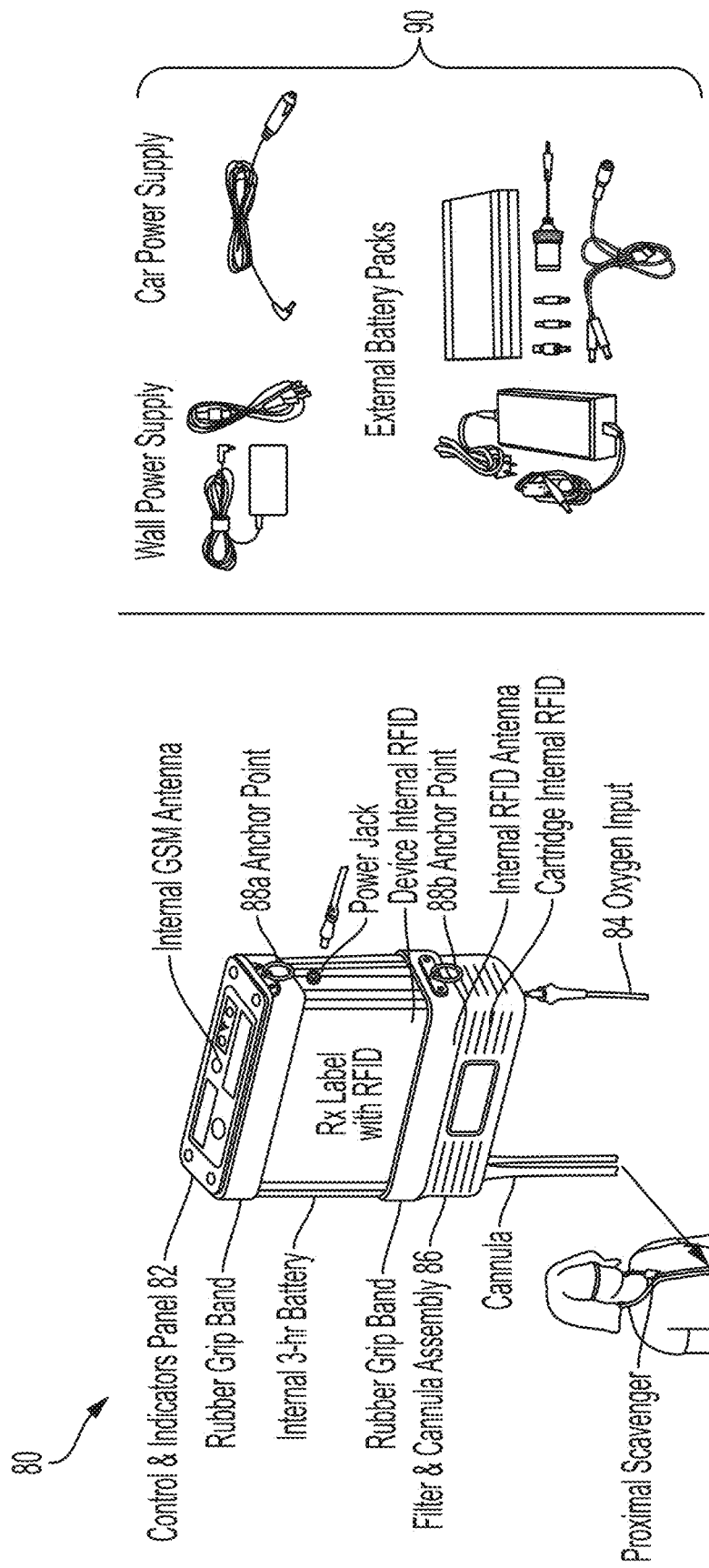
FIG. 6 is an exemplary embodiment of an NO generation system with a user interface on one surface and a scavenger cartridge removably attached to another surface.

FIG. 6 depicts an embodiment of the NO generation device 80 with a user interface 82 on one surface and a scavenger cartridge removably attached to another surface. In some embodiments, oxygen from an external source 84 flows through the removable cartridge. A dual lumen cannula connection 86 on the cartridge provides independent outputs for oxygen and NO-containing gas. In some embodiments, oxygen connects directly to the device 80. Anchor points 88a, 88b on the enclosure enable the connection of a shoulder strap, backpack, belt or other means of carrying the device. Accessory components 90 shown on the right side of the figure include adaptors to automobile cigarette lighters, wall supplies, and external battery packs.

Figure 7:
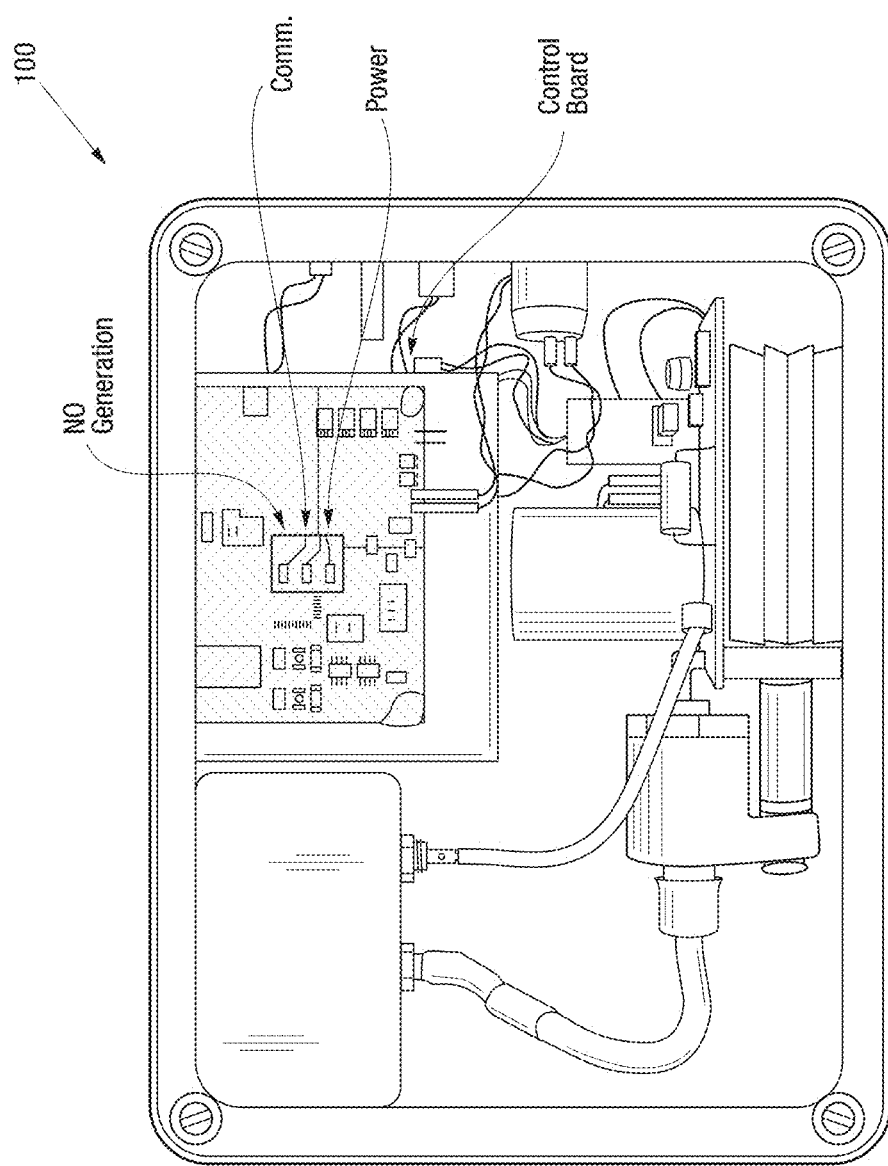
FIG. 7 is an exemplary embodiment of an ambulatory NO generation system.

FIG. 7 illustrates an embodiment of the internal components of a portable NO generation device 100.

Patient Delivery Devices

Figure 8A:
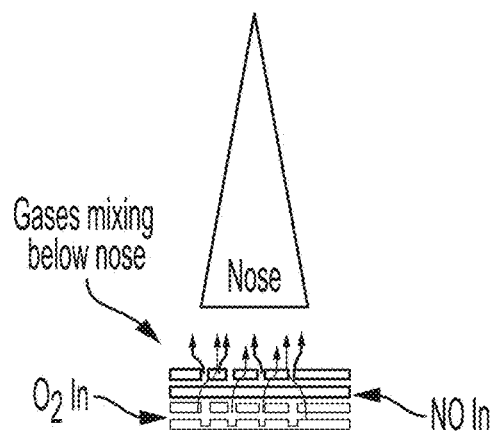
FIG. 8A and FIG. 8B are embodiments of a nasal cannula for use with an ambulatory NO generation system.
Figure 8B:
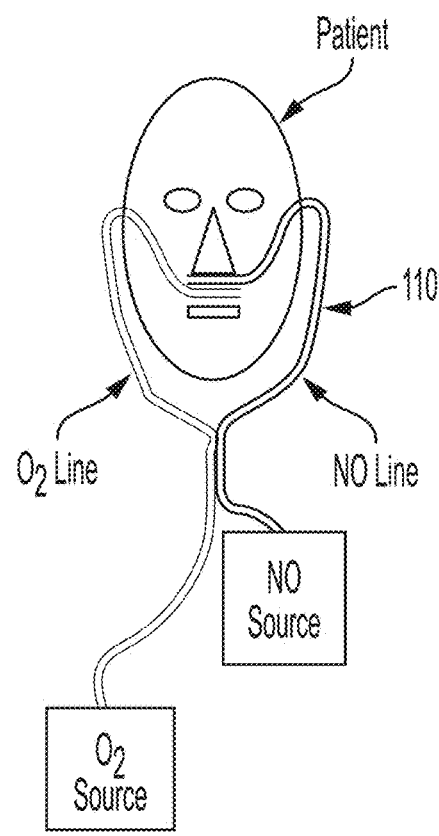

The generated NO in the form of the NO-enriched product gas can be delivered to the patient in a variety of ways. In some embodiments, the NO is delivered through a nasal cannula. In some embodiments, the gases exit an array of holes in the vicinity of the nose of the patient and mix in the space between the cannula and the nose. The cannula can include a variety of configurations. In some embodiments, holes of a cannula 110 are positioned underneath the nose without the use of prongs, as illustrated in FIG. 8A and FIG. 8B. In some embodiments, a cannula 120 can include prongs 122a, 122b that can be positioned within a portion of the nose of a patient, as illustrated in FIG. 8C and FIG. 8D. The prongs 122a, 122b can serve as mixing chambers and direct flow into the nose. It will be understood that prongs of a cannula can also be directed into the mouth. Prongs can include a single lumen or multiple lumens.

In some embodiments, the device can include a dual-lumen cannula with one lumen for NO and one lumen for $O_2$. In some embodiments, the two gases mix at the base of the nose before exiting the cannula. In some embodiments, NO and $O_2$ are transported in independent lumens and delivered through dual-lumen nasal prongs so that $O_2$ and NO are delivered to each nostril and mixing occurs within the nostril. This allows for the delivery of both medical gases to the patient in the event that one nostril is compromised (partially or fully blocked). This configuration also ensure that the NO is exposed to elevated levels of $O_2$ as late as possible, thereby minimizing the formation of $NO_2$.

Figure 10:
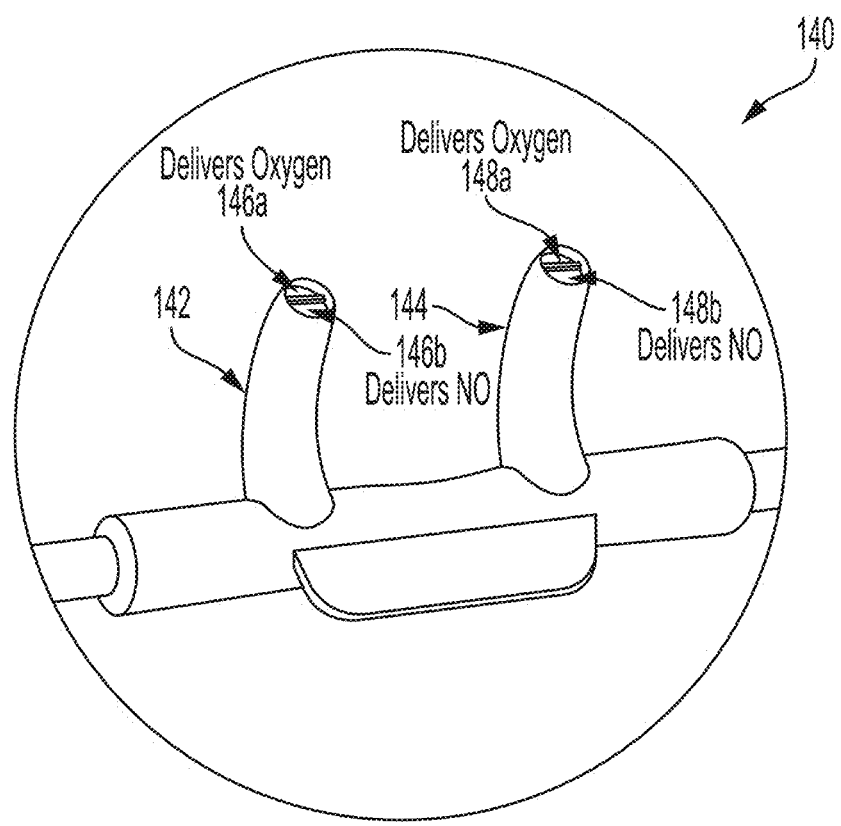
FIG. 10 is an exemplary nasal cannula with two lumens in each prong.
Figure 11:
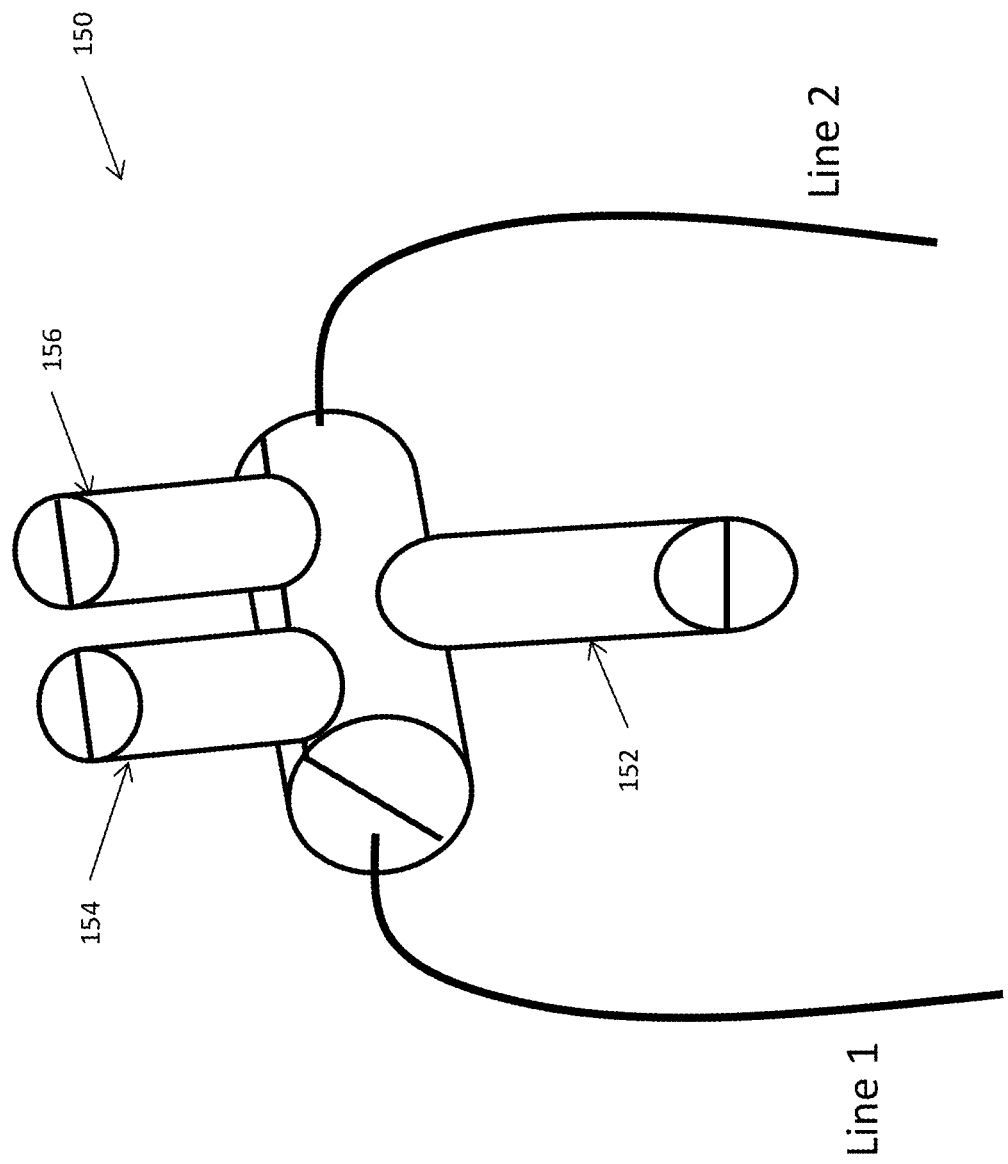
FIG. 11 is an exemplary nasal cannula with a prong for the mouth.
Figure 12A:
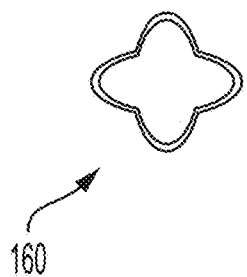
FIGS. 12A, 12B, 12C, and 12D are cross-sectional views of various embodiments of nasal cannulas in inflated and uninflated states.
Figure 12B:
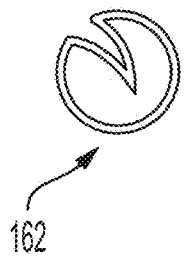
Figure 12C:
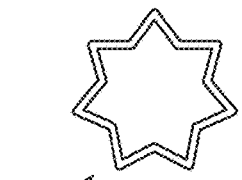
Figure 12D:
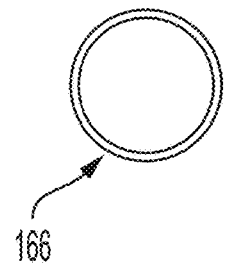

FIG. 9 depicts an exemplary nasal cannula 130 with tricuspid valves 132, 134 at the end of the nasal prongs 136, 138. The valve opens when NO is pushed to the patient. The valves are closed during exhalation, preventing exhaled gases and humidity from entering the cannula. FIG. 10 depicts an exemplary nasal cannula 140 with two lumens 146a, 146b, 148a, 148b in each prong 142, 144. Within each prong, NO is delivered through one lumen and $O_2$ is delivered through the second lumen. Inspiration detection can be done through either lumen. FIG. 11 depicts an exemplary nasal cannula 150 with a prong 152 for the mouth. Each of the three prongs 152, 154, 156 can be dual lumen to deliver $O_2$ and NO independently.

In some embodiments, a controller of the NO generation device is configured to deliver NO in a pulsatile fashion, synchronized with patient respiration. The nasal cannula prongs inserted into the patient nostrils can expand in diameter during inspiration flow. The inflated prong can obstruct a larger portion of the nostril than when the prong is not inflated, which allows the inflated prong to partially block the flow of air into the nostril and give preference to the NO-containing gas from the nasal cannula. As the prong decreases in cross-sectional area during exhalation, the uninflated prong does not present a significant obstruction to exhaled gases. The increase in the cross-sectional area of the prong can be accomplished by a non-destructive deformation of the prong material in the radial direction. With sufficient flow, elastomeric materials will contort to increase cross-sectional area. The cross-sectional area also increases by circumferential elastic deformation (hoop strain) of the nasal prongs during pumping of gases to the nose.

FIGS. 12A-12D illustrate various embodiments of nasal cannula cross sections in uninflated and inflated states. Three exemplary cross sections of nasal prongs 160, 162, 164 are shown in a relaxed state during patient exhalation. A prong 166 illustrates a cross section of a prong in an inflated state. The circular shape to the cross section of the inflated prong 166 can be the inflated cross section of all three prongs 160, 162, 164 in an inflated state as NO is pumped to the patient. It will be understood that the nasal prongs can have any cross section, and that cross section of an inflated prong can have any shape as long as the inflated state of the prong always increases the blockage of the nose during NO delivery to the patient thereby decreasing entrainment of ambient air.

In some embodiments, a valve at the end of the cannula nasal prong prevents entry of exhaled gases and related humidity into the prong. This can aid in prevention of condensation of humidity within the nasal cannula. In some embodiments, a passive valve in the shape of a cuspid valve or duckbill valve can reduce blocking of exhaled gases through the nose because it becomes smaller in cross-section when gas is not flowing through it. In some embodiments, an active valve is located at the distal end of the nasal prong. In some embodiments, NO-containing gas is pressurized within the cannula behind a valve between breaths and released when inspiration is detected by actively opening the valve. In some embodiments, a pressure-activated "pop-off" valve passively opens when the cannula pressure exceeds the cracking pressure of the valve. Pressure within the cannula is controlled so that the passive valve opens in synchrony with inspiration.

When the patient inspires gas from a nasal cannula, air from the environment entrains and is added to the flow, thereby diluting the gas delivered. An exemplary nasal cannula 170 having features to prevent dilution of the delivered gas is shown in FIG. 13A and FIG. 13B. In some embodiments, the nasal cannula 170 includes unique nose prongs 172 that have a skirt 174 around them can be used to decrease the dilution of the delivered gas. The skirt 174 acts like a lip seal or check valve, permitting exhalation flow around the prong, but sealing against the nostril wall to prevent entrainment of ambient air.

A nasal cannula can also include features to allow for identification of the device. In some embodiments, a nasal cannula includes a unique identifier to identify it. The unique identified can be positioned in various locations, including in a connector of the nasal cannula. The identifier can be in various forms, including an RFID for wireless communication, a smart chip for direct electrical connection, or a smart bar code to be read optically, or any other mechanism that would allow for identification. In some embodiments, the controller monitors how long the cannula is in use and writes to the memory device to indicate it has been used for the entire duration of its service life. This can also prevent the use of a non-compatible cannula that could result in higher $NO_2$ levels. Other types of information that can be written to the cannula memory device are: part number, lot number, date of manufacture, date of expiration, date of first use, new/used status, patient treatment information, a device settings log, a device alarm log, patient log entries, patient parameter data (respiratory rate, heart rate, body temperature, $SpO_2$ level, $EtCO_2$, activity level.

Figure 14:
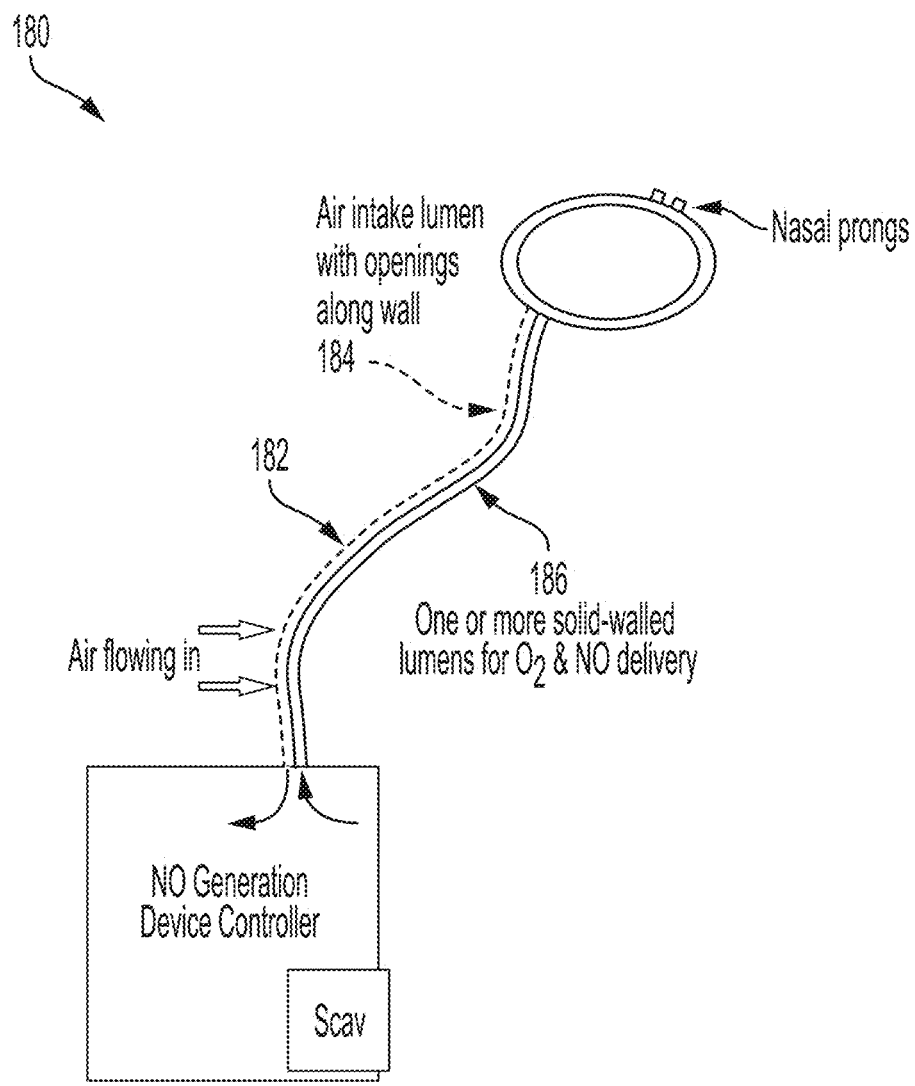
FIG. 14 is an embodiment of a cannula and tubing with a perforated air lumen.
Figure 17:
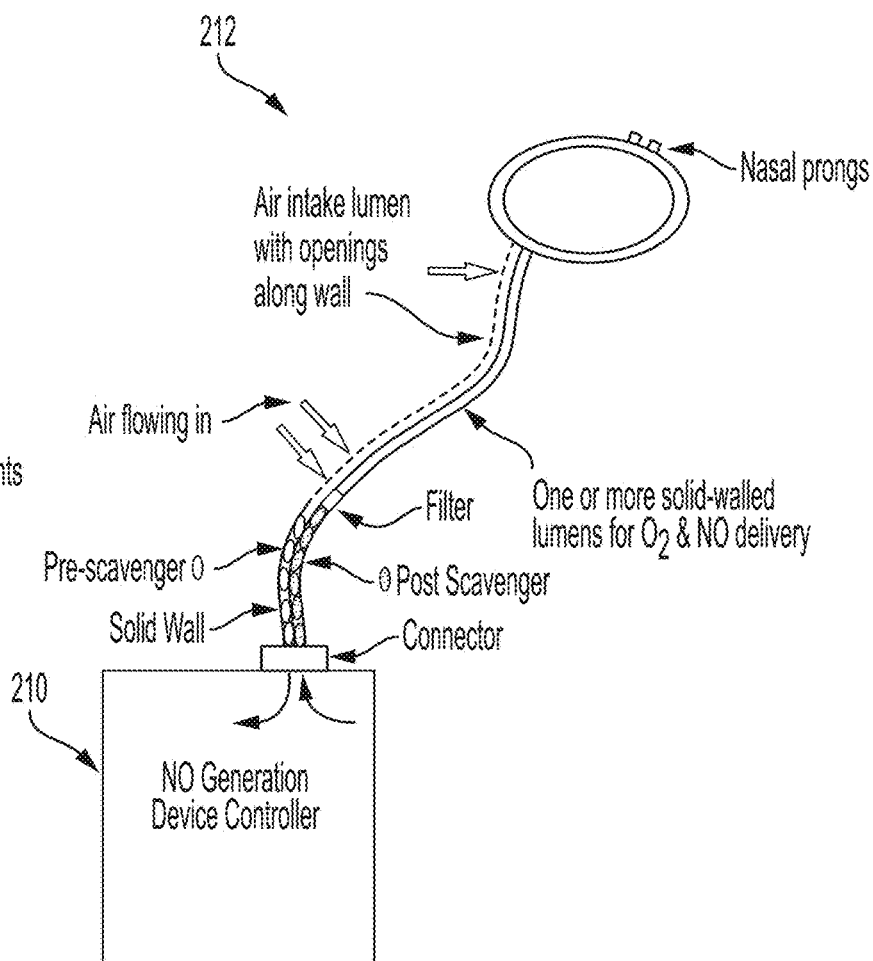
FIG. 17 is an embodiment of a cannula and tubing with a perforated air lumen and scavenger

Depending on the placement of the portable NO generation device, the amount of reactant gas, for example ambient air, that is sourced by the device can vary. For example, the ambulatory device can be placed in a bag or worn under a coat of a patient. In this type of scenario, the device may not be able to source sufficient air to be used as the reactant gas to generate a therapeutic amount of NO. In some embodiments, the gas delivery method (cannula, face mask, CPAP mask, etc.) can include an extra lumen for sourcing air, as shown in FIG. 14. The air lumen 182 can have one or more openings 184 (such as perforations) so that air can enter the lumen from anywhere along the length of the cannula. The perforations help ensure that the device can pull air from somewhere along the length of the NO delivery conduit (FIG. 17). An embodiment of a cannula 180 with first and second lumens 182, 186 is shown in FIG. 14. It will be understood that any type of opening along any portion of the delivery device can be used as long as air can pass therethrough in sufficient amounts to allow a desired amount of NO to be generated.

Figure 15:
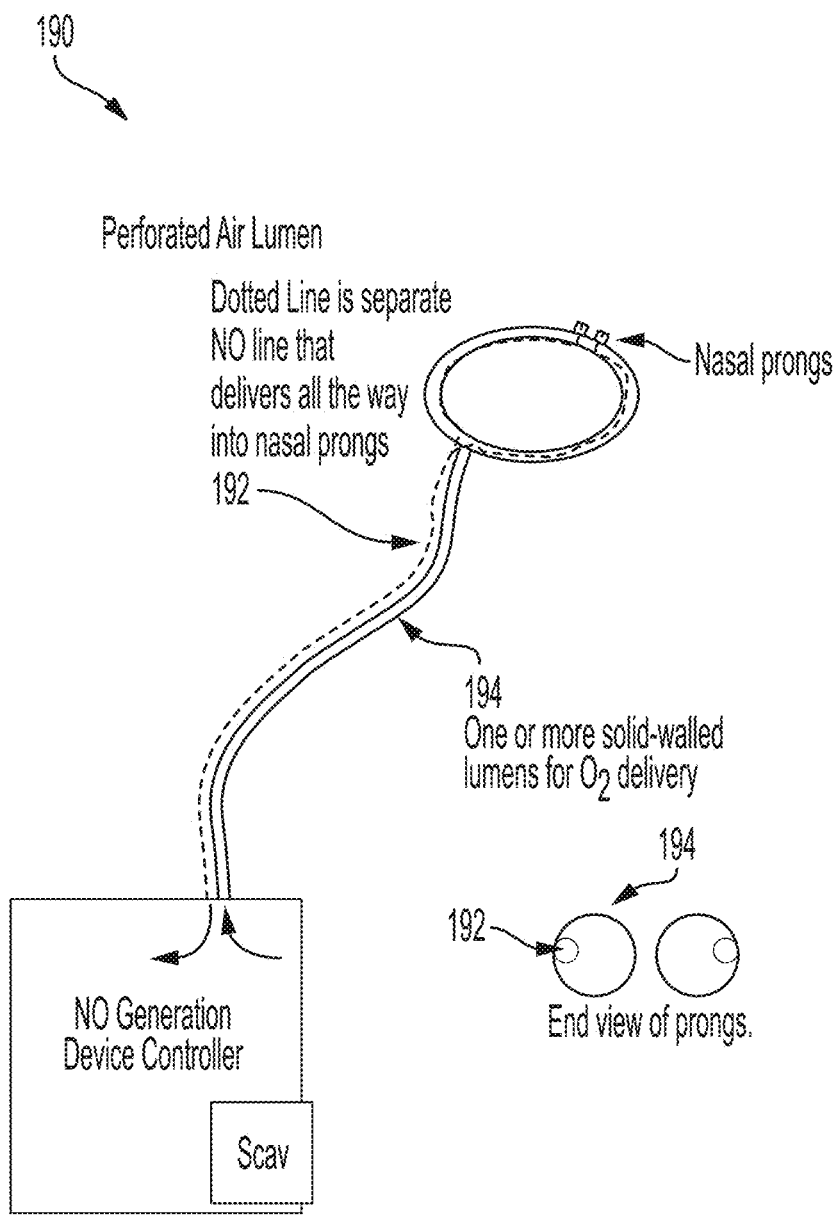
FIG. 15 is an embodiment of a cannula and tubing with a perforated air lumen.

It is a common understanding that keeping NO away from $O_2$ as long as possible minimizes $NO_2$ formation. Thus, a delivery device, such as a cannula 190 as shown in FIG. 15, can include features to separate the NO and $O_2$ as long as possible before patient delivery. In some embodiments, a nasal cannula 190 features an independent lumen 192 for NO delivery to the patient that terminates in small NO tubes that go through each prong so that $O_2$ does not suppress NO flow due to its greater flow rate and pressure, and an $O_2$ lumen 194, as shown in the exemplary cannula 190 shown in FIG. 15. In some embodiments, a nasal cannula uses a venturi or jet configuration to draw NO into either the $O_2$ flow or the inspiratory flow.

Figure 16:
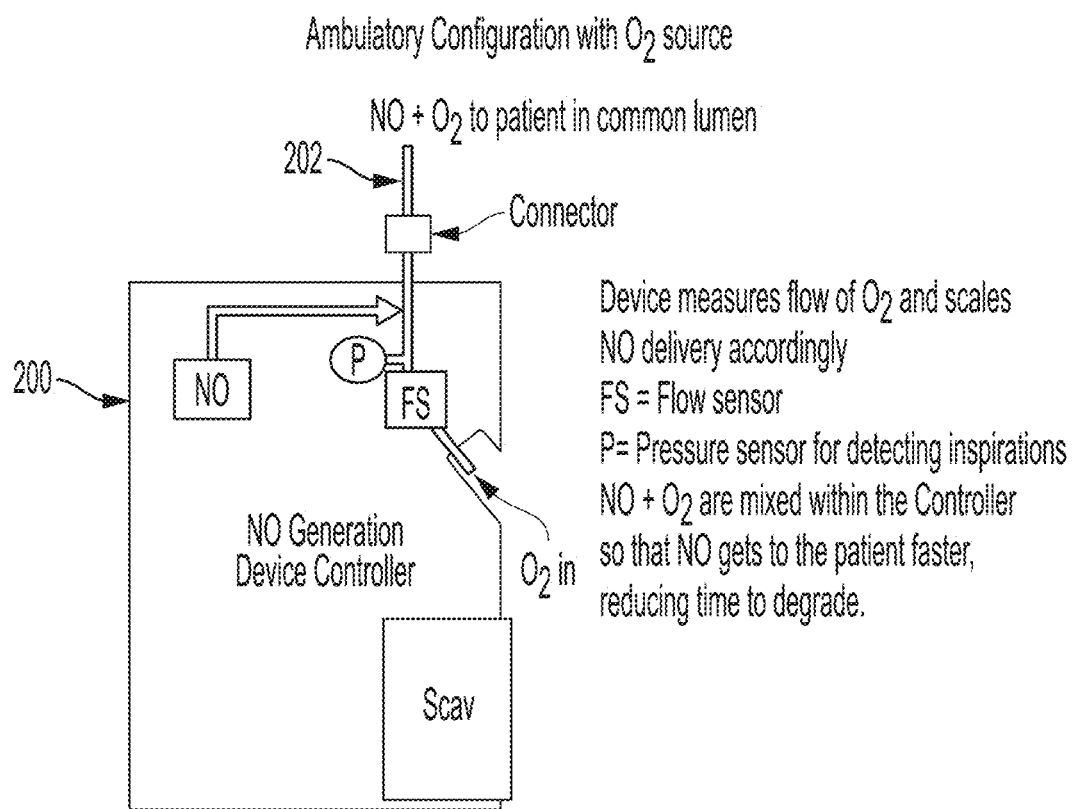
FIG. 16 is an embodiment of an ambulatory NO generation device.

There are different points along the cannula at which the $O_2$ and the NO can be mixed before the gases reach a patient. In some embodiments, it is possible to keep the NO and the $O_2$ separate as long as possible until it enters a patient's nose in order to reduce $NO_2$ formation. The $NO_2$ formation due to high NO concentration is the predominant effect. In some embodiments, it is possible to mix NO with the $O_2$ flow into a common lumen 202 as soon as possible so that transit time to the patient is reduced. Thus, an ambulatory device 200 that introduces high concentration NO to the $O_2$ flow within the ambulatory device can offer reduced $NO_2$ levels at the patient, as shown in an embodiment of an NO generation device 200 shown in FIG. 16.

Typically, NO-containing gases are scavenged for $NO_2$, however this is not necessary if the $NO_2$ levels within the product gas (the post-plasma gas) are sufficiently low. In some embodiments involving a scavenger, the scavenger can be located at/within the controller and/or within the delivery tube and/or proximal to the patient. In some embodiments, the cannula tube is filled with scavenger material partially or completely along its length. In some embodiments, the tubing of the cannula is thin because kink-resistance comes from the scavenger material within the tubing rather than the tubing itself. In some embodiments, the cannula tubing is lined with an $NO_2$-absorbing scavenger material fully or partially along its length. In some embodiments, a nasal cannula with pre-scavenger in addition to NO scavenger can be used.

In some embodiments, a nasal cannula includes a scavenger and there is no scavenger at the controller in the portable NO generation device. A device 210 does not have a cartridge at all, such that the system has one disposable component 212 (a cannula) instead of a cannula and a scavenger cartridge, as shown in FIG. 17. In some embodiments, a nasal cannula 212 can include a scavenger near the point of inspiration (e.g. close to the nose).

Figure 18:
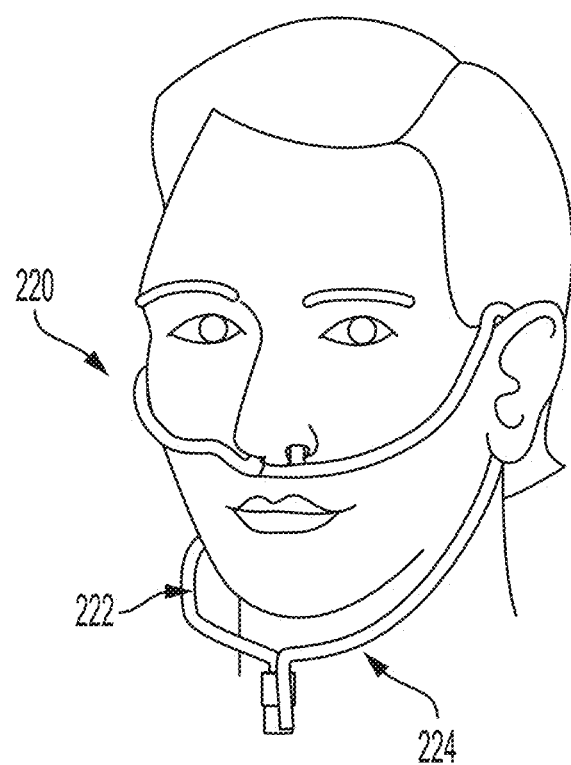
FIG. 18 is an embodiment of a dual lumen cannula having two lumens, with an $NO_2$ absorbent material within one of the cannula lumens.

FIG. 18 depicts a dual lumen cannula 220 having first and second lumens 222, 224 with an $NO_2$ absorbent material within one of the cannula lumens 224. Oxygen flows within the first lumen 222. In some embodiments, the $NO_2$ absorbent material is a coating or lining on the inner diameter of the cannula tubing. In some embodiments, the scavenger material consists of particles or pellets within the cannula lumen with a filter at each end. In some embodiments, the oxygen and NO product gases exit though separate lumens with each nasal prong.

In some embodiments, a nasal cannula includes a scavenger near the point of inspiration (e.g. close to the patient, for example, the nose of the patient). In some embodiments, a scavenger is located behind the patient's ear, where the cannula tubing wraps around the ear. In some embodiments, a scavenger housing is located at the base of the patient's neck, like a pendant.

A cannula design can also be varied. Due to the continuous conversion of NO to $NO_2$, it can be advantageous to scavenger the NO-containing gas immediately before it enters the patient. In some embodiments, a nasal cannula can include a scavenger below the nose so the gas passes through the scavenger right before the gas enters the patient. In some embodiments, a scavenger along the length of the cannula tubing hangs like a pendant at the base of the User's neck. In some embodiments, a tubing of a nasal cannula can be lined or coated with scavenger material. In some embodiments, a nasal cannula tube lined with scavenger material contains a material that changes color as an indicator of scavenger exhaustion. In some embodiments, the color-changing material is similar to litmus paper, changing color in the presence of pH changes. In some embodiments, the cannula tubing material itself absorbs $NO_2$ sufficiently that no additional scavenger material is required.

Many patients are self-conscious about using a nasal cannula because it covers part of their face. In some embodiments, NO can also be delivered from a location near the ear to the respiratory tract. In some embodiments, an NO delivery tube is tunneled from the ear to the trachea. In some embodiments, NO is delivered through the ear drum and travels to the respiratory tract through the Eustachian tube. In some embodiments, NO is delivered directly to the trachea through an opening at the base of the anterior neck.

In some embodiments, NO is added to the flow of $O_2$ from an oxygen concentrator within or immediately after the NO controller. This approach is particularly helpful in reducing $NO_2$ formation when a high volume of $O_2$ is used, thereby reducing transit time of NO from controller to patient. Thus, an ambulatory device that introduces high concentration NO to the $O_2$ flow within the device has the potential of reducing $NO_2$ levels at the patient.

Docking Station and Power Source

In some embodiments, a base, or docking, station is provided. The base station can be used to provide charging to the NO generation device battery. Charging may be done using an electrical connection or an inductive connection. The base station can be connected to external devices using a variety of techniques, including but not limited to a telephone line, a cable TV connection, a Wi-Fi connection, and a cellular network connection. In an embodiment, the NO generation device and/or charging station can project information onto a surface. For example, the charging station can project the status of battery charge to the ceiling of a bedroom.

The base station can include various sensors. In some embodiments, the base station can include one or more gas analysis sensors to check calibration of the NO generation device. When the NO generation device is docked, the base station can pull NO-containing air into the base station for analysis of NO levels and/or $NO_2$ levels to ensure safe operation. In some embodiments, the base station can perform calibration on a controller by connecting to a cannula connection. Battery charging can provide time for calibration, although calibration is performed independent of battery charging. Gases for analysis can be sourced from the cartridge connector to the controller, a T-fitting that splits the flow of the controller output gases to enable simultaneous cannula gas delivery and gas analysis, or a dedicated gas port for calibration purposes. The measurements can be made with electrochemical cells, however optical and chemiluminescent means can also be used. The base station can receive power from either an AC power outlet or a DC connection. For example, 12 VDC can be used as this voltage can be found in automobiles. The base station can be used to download data from the NO generation device. The downloaded data can be stored within the base station or exported using the internet, Wi-Fi, wired connection, or cellular network or optical means to a separate external storage location.

Various sources can be used to provide power to the NO generation device. Some users can require use of the NO generator at all times day or night. These users can also need to wear the device in an environment where fluid is present, such as the shower. To address the risk of fluid ingress, in some embodiments the NO generation device is designed with a housing that has minimal openings. For example, the device can be water-proof. Battery charging can be accomplished in a variety of ways, but in an embodiment the battery can be charged via inductive means through the wall of the enclosure. Various other contacts can be used to charge the device, including but not limited to sealed, gold plated contacts. In some embodiments, a base station, or docking station, can be provided as a nest for the NO generator to reside in during charging.

FIG. 19A, FIG. 19B, and FIG. 19C illustrate an embodiment of a mobile NO generation device 230 positioned in a docking, or base, station 232. The docking station 232 can include features to allow for communication of status of the device, or an illumination feature to locate the docking station in the dark. The docking station 232 can also include a door that covers the disposable bay.

In some embodiments, battery charging can be accomplished through an electrical connection within the enclosure that is fluid-tight. Air for plasma generation is sourced through a micro-filter, such as Gore-Tex to prevent fluid ingress. In some embodiments, the microfilter is hydrophobic to further prevent the ingress of liquid water. The air inlet can have an additional filter to capture large particulate. It can also be protected with louvers and/or a water trap.

In some embodiments, an accessory docking station can plug into a car cigarette lighter or other electrical connection in a vehicle. The docking station can fit within a standard cup holder in a car or hang on the car door. To hang on a car door, the docking station can include a feature that inserts between the inside surface of the car window glass and the window seal. One or more magnets within the generator enclosure and accessory docking station aid the user in seating the generator within the docking station.

It can be understood that the power delivery capability of the base station to NO generator needs to exceed the sum of battery charging power and NO generator operating power so that the batteries can charge. The battery life can vary, but in an embodiment the target battery life is 12 hours. The charging time is required to be less than the battery life, for example 12 hours, so a user can use one device while charging a second device.

In some embodiments, an NO generation device does not include its own battery. Instead, the device can be electrically connected to a separate device, such as an $O_2$ generator, and draw power from the other device's battery or power supply. In some embodiments, an NO generator can be embedded within the $O_2$ generator housing and the NO generator can share the battery, memory, micro-controller, alarm buzzer, user interface, housing, and other components of the $O_2$ generator. It will be understood that the NO generator can be embedded or integrated with other devices as well, including but not limited to a VAD, nebulizer, humidifier, CPR machine, Bi-PAP machine, CPAP machine, heated and humidified jet cannula and/or AED.

Air Sources

In some embodiments, the system can utilize an oxygen concentrator. Patients with pulmonary hypertension are treated with high levels of oxygen ($O_2$). Devices exist that process atmospheric air to increase the oxygen content by separating out the nitrogen content. These devices are portable and battery powered. This concomitant use of NO with an $O_2$ concentrator or oxygen tanks will decrease the demand for $O_2$ and/or improve patient mobility.

NO production is optimized when plasma is generated in a Stoichiometric ratio of 50/50 oxygen to nitrogen. Atmospheric oxygen levels are 21%, but an oxygen concentrator can be used to increase the percentage of oxygen in air. In some embodiments, an output from an oxygen concentrator can be used as the reactant gas and routed through an NO-generation device so that NO production is optimized. This could reduce the size of the battery several fold for a given amount of runtime.

The sources of reactant gas can vary beyond the output of the $O_2$ concentrator. In some cases, a patient is connected to a tank with 100% oxygen or an oxygen concentrator that produces 100% oxygen. In some embodiments, an ambulatory NO generation device can blend the high $O_2$ content gas with atmospheric air to reduce the $O_2$ concentration and increase $N_2$ concentration to optimal levels in the plasma chamber, or use pure air. NO converts to $O_2$ more rapidly in the presence of high concentrations of oxygen. Thus, the device can include features to keep the NO and the $O_2$ separated as long as possible. In some embodiments, air is compressed into a chamber within the NO generation device containing a material with an affinity for $N_2$, such as zeolite. When the chamber is depressurized with reactant gas, the exiting gases have higher oxygen concentration than the ambient air thereby producing higher levels of NO when exposed to plasma. The $N_2$ loaded into the material with affinity for $N_2$ is vented to atmosphere periodically. In some embodiments, the $N_2$ is vented to atmosphere during patient exhalation. In some embodiments, the $N_2$ is vented to atmosphere during patient inspiration. In some embodiments, the $N_2$ is pumped through the plasma chamber with the plasma OFF to the patient during patient exhalation so that there is an alternating pulse train of NO-containing product gases followed by gases that are have little to no NO and higher $N_2$ than the initial reactant gas.

Respiratory events occur quickly, requiring a fast system response to delivery an NO pulse. In some cases, such as when it is desirable to synchronize the pulse with the leading edge of inspiration, the pulse can begin within 50 milliseconds of the beginning of inspiration. This is faster than a timescale over which a pump alone can accelerate from rest to deliver a bolus of NO-containing gas into a tube which will conduct it to the nose. To achieve a fast response, in some embodiments, an ambulatory device prepares a bolus of NO-containing air in a reservoir during patient expiration. When an inspiration is detected, air from a compressed source is released, pushing the NO bolus through the cannula to the patient. In one embodiment, the staging reservoir is one or more cannula lumen. In one embodiment, the lumen within the cannula is a dedicated NO-delivery lumen. The NO-containing gas can pass through a scrubber before staging in the reservoir, after the reservoir, at a location near the patient within the cannula, or not pass through a scrubber at all if $NO_2$ levels are sufficiently low. The reservoir decouples the action of the pump from the delivery of NO-rich gas. The pump stores mechanical potential energy invested in pressurized gas in the reservoir. This store of potential energy can be released more quickly from the reservoir than a small pump could deliver directly. In one embodiment, a large pump delivers gas at a fast rate however it has more mechanical inertia that hinders its ability to change its output rate quickly enough. Both solutions, a pump and/or a pump and reservoir can service a wide range of flow rates while maintaining a fast response time. The reservoir does not need to be an explicit pressure vessel. Any volume in the pneumatic circuit between the pump and the flow control valve or valves can serve as the reservoir. In one embodiment with a reservoir, the reservoir as a volume of 150 ml.

In some embodiments, the ambulatory device sources air from the atmosphere. Air is pulled into the device with a pump and processed with one or more of a mechanical filter, one or more scavengers, and/or one or more carbon filters. At a minimum, an ambulatory NO generation device filters the incoming air prior to generating NO. The mechanical filter size can vary, but in an embodiment is on the order of about 0.22 micron pore size to prevent entry of bacteria. The scavenger can be formed from a variety of material, but in an embodiment is soda lime. The carbon filter is used to remove organic compounds from the air prior to entering the plasma chamber.

FIG. 20A illustrates an embodiment of pneumatic pathway through a wearable NO generator that can operate at higher pressure resulting in faster response times than systems relying solely on a pump. In the system illustrated in FIG. 20A, ambient air or another other reactant gas is drawn into the system through a filter 240 by a pump 242. Pressurized gases travel on through a plasma chamber 244, where high voltage electrodes produce electrical discharges that disassociate $N_2$ and $O_2$ molecules to form NO and some $NO_2$. Then the product gas flows through a flow controller 246 that can be configured to govern the level of flow that is actually delivered to the patient. In some treatment conditions, flow levels are varied in a continuous fashion as boluses of NO-containing gas are delivered, usually in sync with patient inspiration. From the flow controller 246, gases flow through a scrubber 248 to remove $NO_2$ from the product gas and a filter 250 prior to delivery to a patient.

In some embodiments, after a filter 252 and a pump 254, a flow controller 256 can also be located before the plasma chamber 258, thereby controlling the flow of reactant gases instead of product gases, as shown in FIG. 20B. This approach provides a benefit in not exposing the flow controller to NO-containing gases and shortening the pneumatic pathway from plasma to scrubber since pathway length relates to transit time and greater transit time results in greater $NO_2$ formation. In some embodiments, the flow controller can be in the form of one or more proportional valves. Between breaths, the one or more proportional valves can be used to allow pressure to build up within the system enabling the delivery of short, high pressure pulses. In some embodiments, the one or more proportional valves are not able to fully close so that the system can deliver NO to the patient in the event of a proportional valve failure. In addition to flow controller activity, throttling the pump provides additional flow control.

Figure 21:
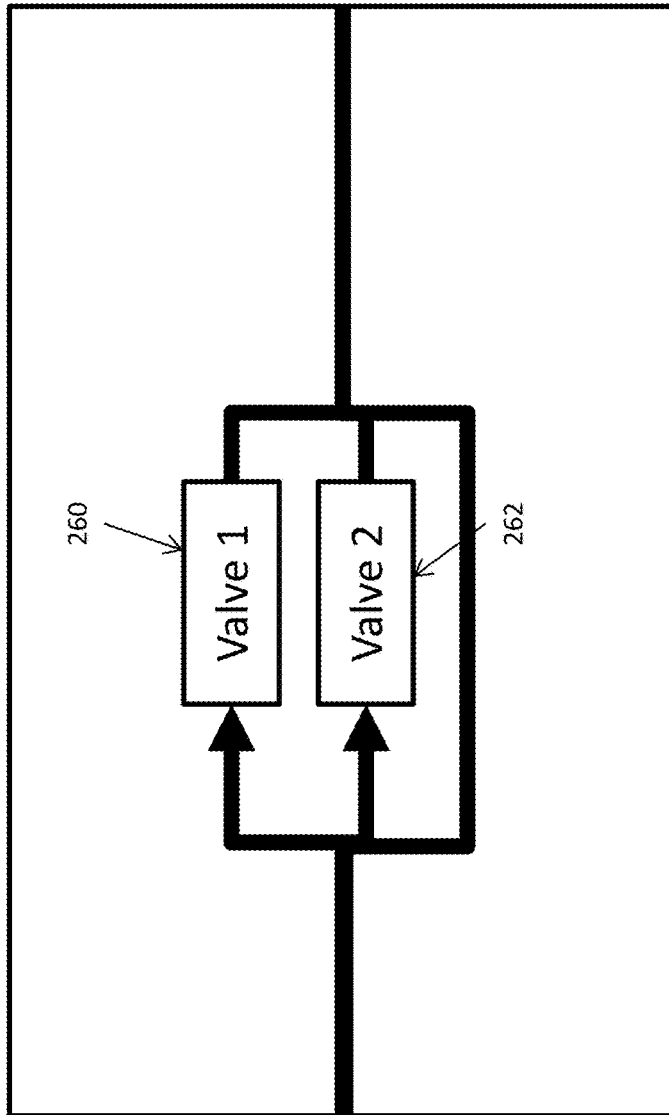
FIG. 21 is an embodiment of a valve assembly where the flow control is accomplished by first and second valves.

FIG. 21 illustrates an embodiment where the flow control is accomplished by first and second valves 260, 262. This approach offers benefits in weight and power draw over a proportional valve approach. An optional bypass path is also shown. The effective orifice size of the first and second valves can be identical or can be different, depending on the flow levels required. This approach provides a step-wise approach to flow delivery to the patient, rather than a continuously variable approach offered by a proportional valve. Embodiments involving more than two valves can provide additional discrete flow levels for the system. In some embodiments, one or more fixed orifices are used to control the flow of air through the system.

Figure 22:
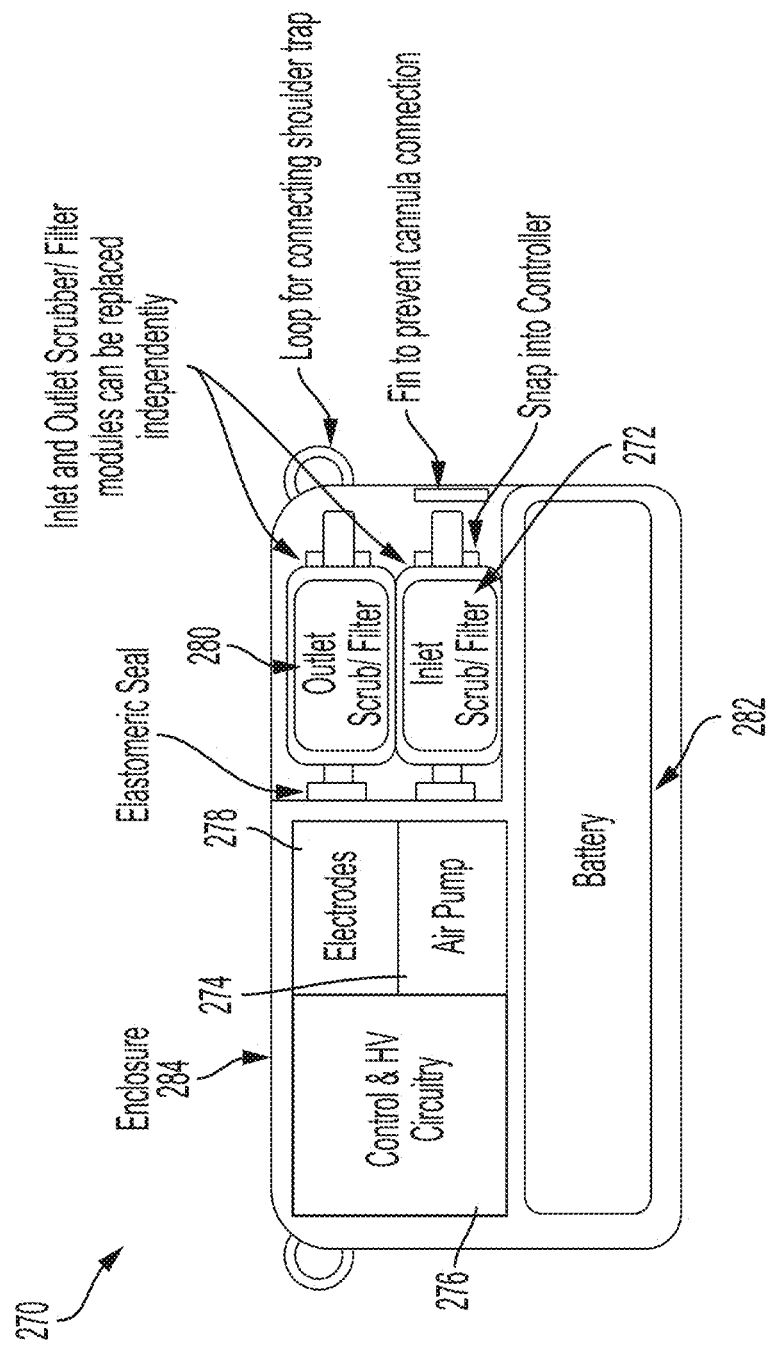
FIG. 22 is an embodiment of wearable NO generation system.

FIG. 22 illustrates an embodiment of a wearable NO generator 270 with an inlet scrubber/filter combination 272, an air pump 274, control and high voltage circuitry 276, one or more electrodes 278, an outlet scrubber/filter 280, a battery 282, and an enclosure 284. The inlet and outlet scrubber/filters can be replaced independently. The scrubber/filters have a tapered or barbed end that is pressed into an elastomeric ring for retention and sealing. The opposite end of the scrubber filter is retained by one or more spring clips that grasp the outer surfaces of the scrubber filters. The user inserts one end of the scrubber/filter into the elastomeric seal, and rotates the body of the scrubber/filter towards the controller enclosure so it "snaps" into position with the one or more spring clips holding it in place, or simply presses the scrubber filter into the device so that it locks into place, and then presses down in order to release it. The scrubber filters can optionally be covered with a cover to protect them from being dislodged during use.

Scrubber/filter combinations do have finite service life due to the finite $NO_2$-absorbing capacity of the scrubber material and coating of filters with particulate matter. This presents a risk that a patient may not replace their scrubber/filter on time, thereby elevating the risk of $NO_2$ exposure. In one embodiment, the NO generation device prompts the user to replace the scrubber/filter when they remove the device from the charger in the morning. In another embodiment, the device generates an audible alarm at time points leading up to complete scrubber/filter exhaustion so that the user can replace the scrubber/filter in time.

The cover of the scrubber/filter has corresponding openings to permit gas entry and exit, as required. In an embodiment, the device can also have a fully-integrated molecular sieve that removes some of the $N_2$ from the incoming air to optimize the $N_2$ to $O_2$ ratio for increased NO production, improved power efficiency and decreased $NO_2$ scrubbing needed. In some embodiments, a molecular sieve can be located post-plasma chamber to remove a specific gas, such as $N_2$, thereby increasing the fraction of NO and $O_2$ in the effluent gases. In some embodiments, a molecular sieve removes some or all of the $O_2$ post plasma chamber to slow the conversion of NO into $NO_2$.

Cartridges

A cartridge for use with the ambulatory NO generation system can include various features and designs. The system can utilize various different types of cartridges that can be used for different applications. For example, cartridges can vary in size of scavenger depending on the expected duration of use and required NO levels. Cartridges could have one or more pneumatic connections, depending on the application. In an embodiment, a single pneumatic connection can be for a single-lumen nasal cannula connection to the device. In an embodiment, two pneumatic connections can be used for a device that adds NO to an existing gas flow. A first pneumatic connection can be for gas flow into the system, and a second pneumatic connection can be for NO+gas output. In some embodiments, three pneumatic connections can be used for a device that measures the flow of an incoming gas flow, but does not add NO to the gas flow. A first pneumatic connection can be for the incoming gas. A second pneumatic connection can be for outgoing gas to the patient. A third pneumatic connection is for NO-containing gas to the patient. The device can source ambient air through a pneumatic connection in the top of the cartridge or through a grille on the side of the controller or cartridge.

Pneumatic connections may be oriented in a concentric fashion, a line, a polygon or some other shape. In one embodiment, all pneumatic connections are established with one user-motion by use of an integrated pneumatic connector.

In some embodiments, the gas handling can occur within the cartridge. Thus, there are no cleaning issues within the controller, and the controller can lack any openings in the enclosure that can allow for fluid or particular ingress.

Figure 23A:
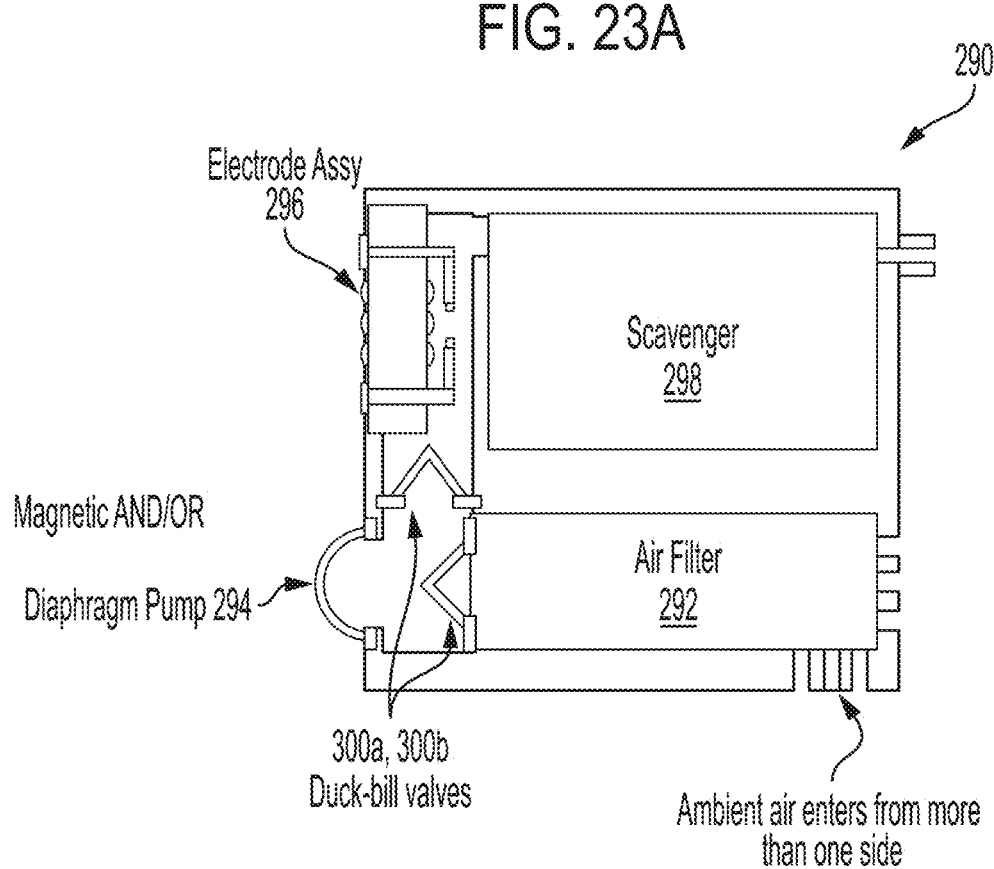
FIG. 23A and FIG. 23B illustrate views of an embodiment of a cartridge for use with an NO generation system.
Figure 23B:

FIG. 23A and FIG. 23B illustrate an embodiment of a cartridge 290 that includes an integral air filter 292, a pump 294, an electrode assembly 296, and a scavenger 298 (cartridge end-view on right). Air flows into the cartridge 290 and through an air filter to the pump. The pump, that can include two one-way valves 300a, 300b (e.g., duck-bill, flapper, ball in cage, tricuspid or similar) and a diaphragm, can be actuated in a variety of ways, including but not limited to the use of a solenoid, a diaphragm, a lever, or other mechanism in the controller. Air exits the pump to the plasma chamber with the electrode assembly and flows on through the output scavenger. The output scavenger can include a filter to capture potential electrode particles and scavenger particles.

The cartridge of the ambulatory NO generation device can have a variety of configurations. In some embodiments, an ambulatory device has a disposable cartridge which may include one or more of the following features: an inlet filter, an inlet scavenger, an inlet carbon filter, an exhaust scavenger, and an exhaust filter. In some embodiments, a connector for a patient delivery device (for example, a nasal cannula) can be connected to the cartridge/disposable portion of the device, rather than the reusable controller. This reduces the number of pneumatic connections to the controller and can decreases the potential of a user to connect the cannula or other delivery device directly to the controller without a scavenger for removing $NO_2$. The connection from a cannula to the cartridge can be different than the connection from cartridge to controller. In some embodiments, the cartridge housing is reusable and only filter elements and/or scavenger material is replaced.

Figure 24:
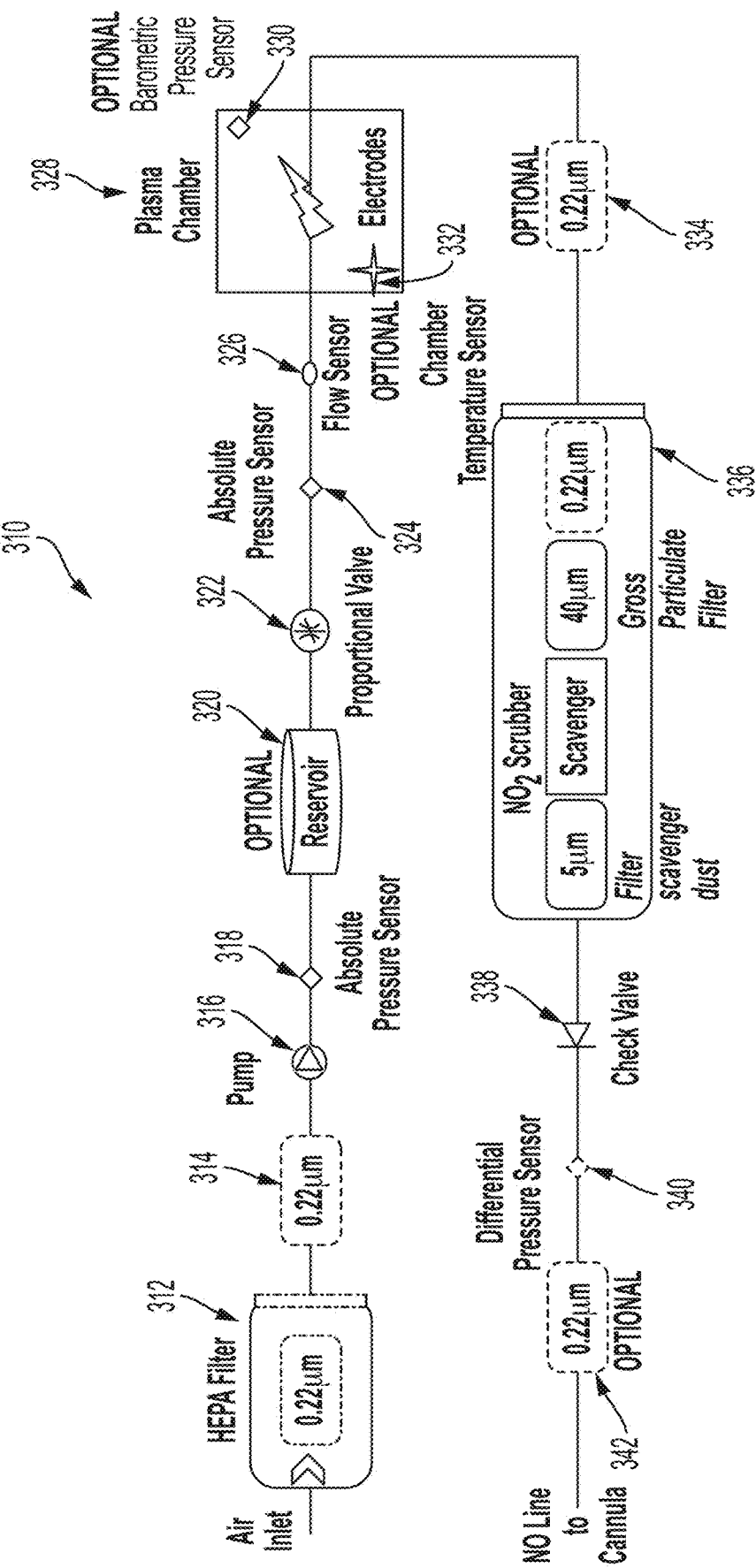
FIG. 24 illustrates an embodiment of a pneumatic pathway within a portable NO generation device.

FIG. 24 depicts an exemplary pneumatic pathway 310 within a portable NO generation device. Shaded portions are removable and disposable. In some embodiments, the removable/disposable elements are located in a single disposable cartridge. In the embodiment depicted, ambient air or other reactant gas is drawn through a disposable filter 312 and then through a permanent filter 314 within the device. The air then flows to a pump 316. The pressure distal to the pump is measured by an absolute pressure sensor 318. This pressure is used to confirm pump activity and measure reservoir pressure when a reservoir 320 is used. The reservoir 320 serves as an accumulator that can provide rapid flow of high pressure air. In some embodiments, the pump alone can sufficiently deliver air flow to the treatment, rendering the reservoir unnecessary. In some embodiments, the air pump pumps against an orifice or one or more valves. A pressure sensor 324 beyond the proportional valve 322 shown is used to measure pressure within the plasma chamber. A flow sensor 326 prior to the plasma chamber 328 is used for closed-loop control to ensure accurate air flow through the plasma chamber. The closed-loop control can be used as input to one or more of the following: pumping effort/speed, valve position, reservoir pressure. The plasma chamber 328 houses one or more electrodes used to create plasma in the air. Optional barometric pressure and temperature sensors 330, 332 connected to the plasma chamber provide additional input to the control algorithm. An optional third filter 324 within the air flow is located within the controller to provide further protection from contaminates entering the controller. Nitric oxide and air then flows through an $NO_2$ scrubber 336 that consists of one or more filters, an $NO_2$-absortive scrubber and another filter. The NO plus air then flows through a check valve 338, a differential pressure sensor 340 used for breath detection, another optional filter 342 and a connection to the delivery tube (e.g. a nasal cannula, catheter, or other tube).

Figure 25:
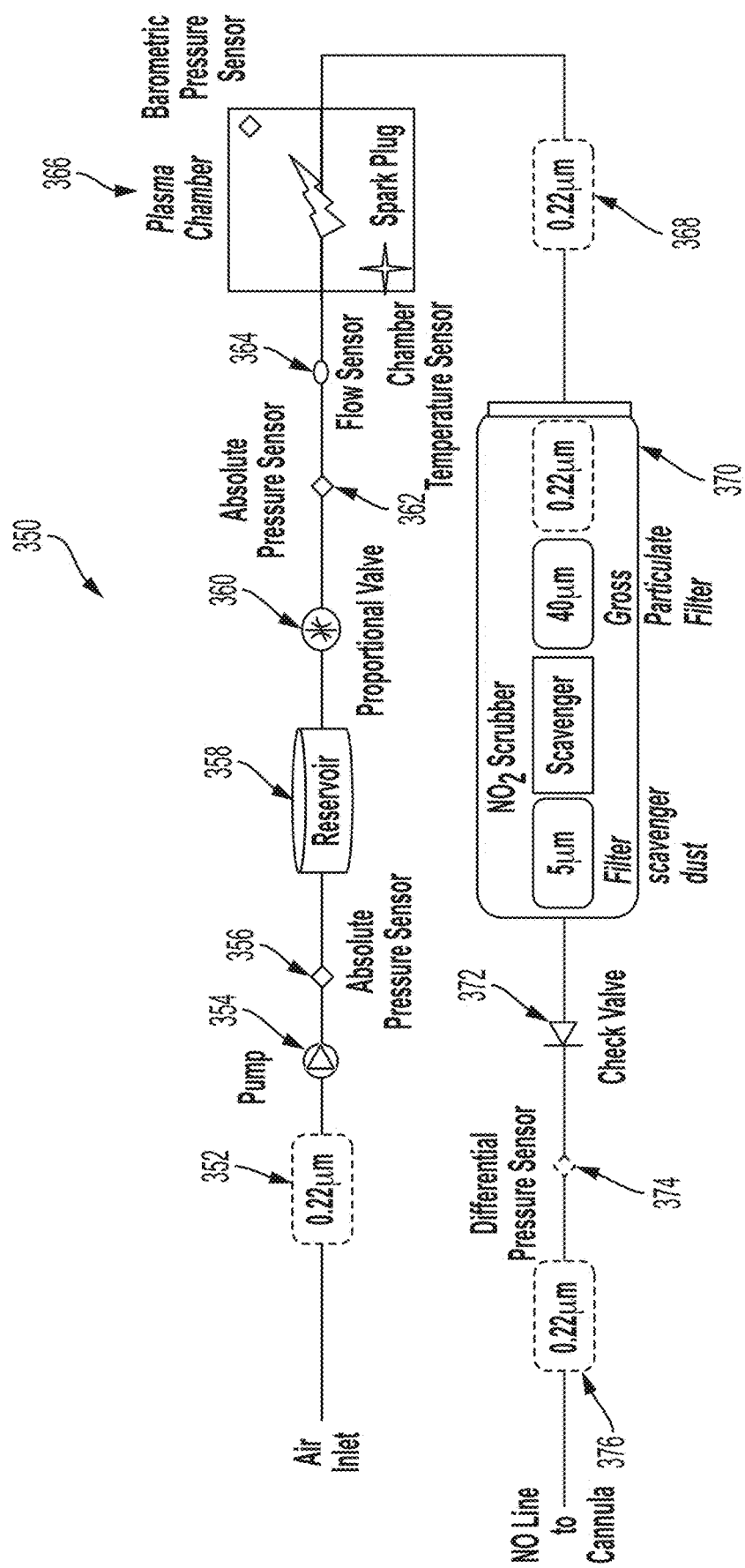
FIG. 25 illustrates an embodiment of a pneumatic pathway within a portable NO generation device.
Figure 26:
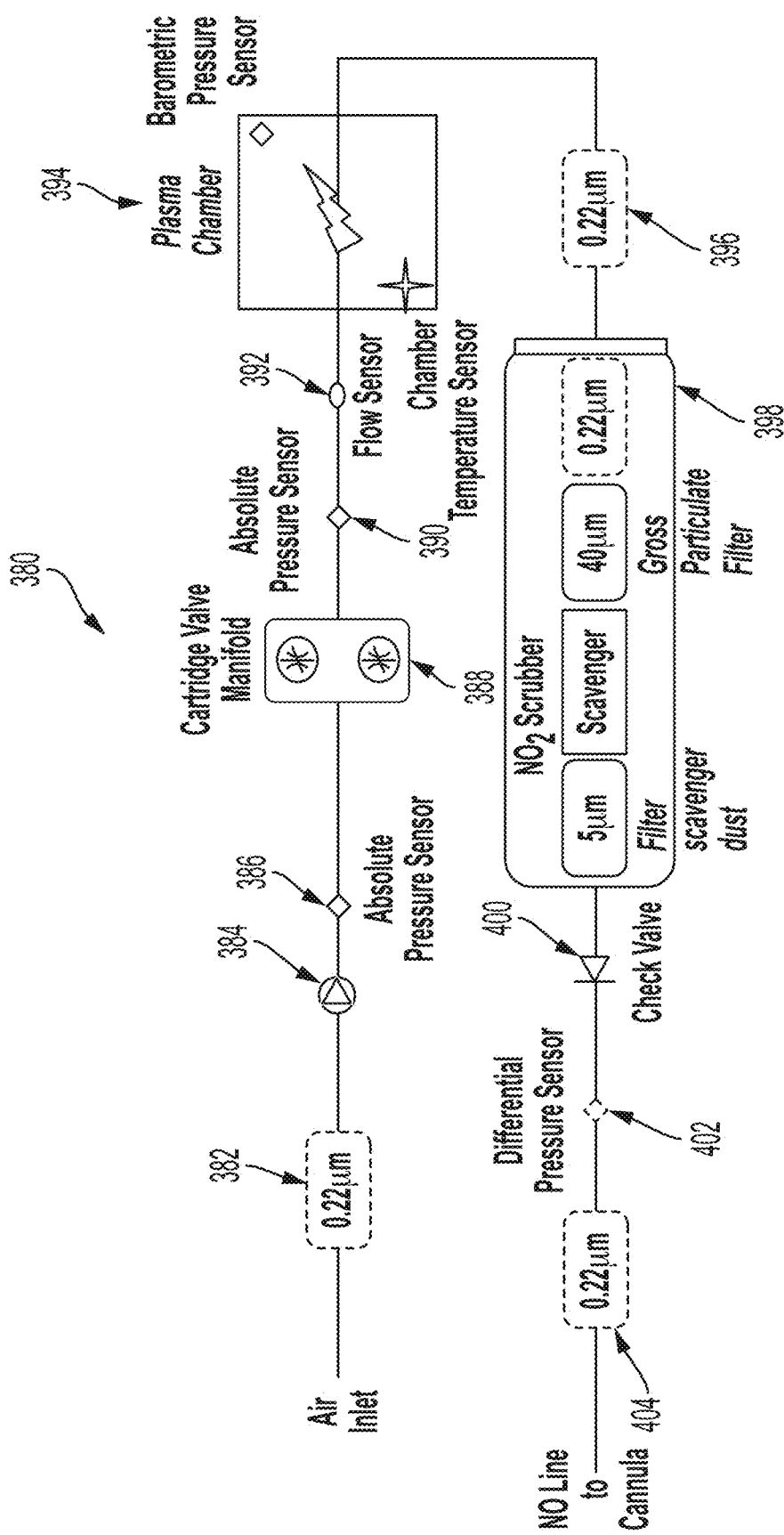
FIG. 26 illustrates an embodiment of a pneumatic pathway within a portable NO generation device.

FIG. 25 and FIG. 26 depict additional exemplary pneumatic pathways within a portable NO generation device. A pneumatic pathway 350 of FIG. 25 illustrates ambient air or other reactant gas drawn through a permanent filter 352 within the device. The air then flows to a pump 354. The pressure distal to the pump is measured by an absolute pressure sensor 356. This pressure is used to confirm pump activity and measure reservoir 358 pressure. A pressure sensor 362 beyond the proportional valve 360 shown is used to measure pressure within the plasma chamber. A flow sensor 364 prior to the plasma chamber 366 is used for closed-loop control to ensure accurate air flow through the plasma chamber. Optional barometric pressure and temperature sensors connected to the plasma chamber provide additional input to the control algorithm. A filter 368 within the air flow is located within the controller to provide further protection from contaminates entering the controller. Nitric oxide and air then flows through an $NO_2$ scrubber 370 that consists of one or more filters, an $NO_2$-absortive scrubber and another filter. The NO plus air then flows through a check valve 372, a differential pressure sensor 374 used for breath detection, another filter 376 and a connection to the delivery tube.

A pneumatic pathway 380 of FIG. 26 illustrates ambient air or other reactant gas drawn through a permanent filter 382 within the device. The air then flows to a pump 384. The pressure distal to the pump is measured by an absolute pressure sensor 386. The air flows through a cartridge valve manifold 388. A pressure sensor 390 is used to measure pressure within the plasma chamber. A flow sensor 392 prior to the plasma chamber 394 is used for closed-loop control to ensure accurate air flow through the plasma chamber. Optional barometric pressure and temperature sensors connected to the plasma chamber provide additional input to the control algorithm. A filter 396 within the air flow is located within the controller to provide further protection from contaminates entering the controller. Nitric oxide and air then flows through an $NO_2$ scrubber 398 that consists of one or more filters, an $NO_2$-absortive scrubber and another filter. The NO plus air then flows through a check valve 400, a differential pressure sensor 402 used for breath detection, another filter 404 and a connection to the delivery tube.

Figure 27:
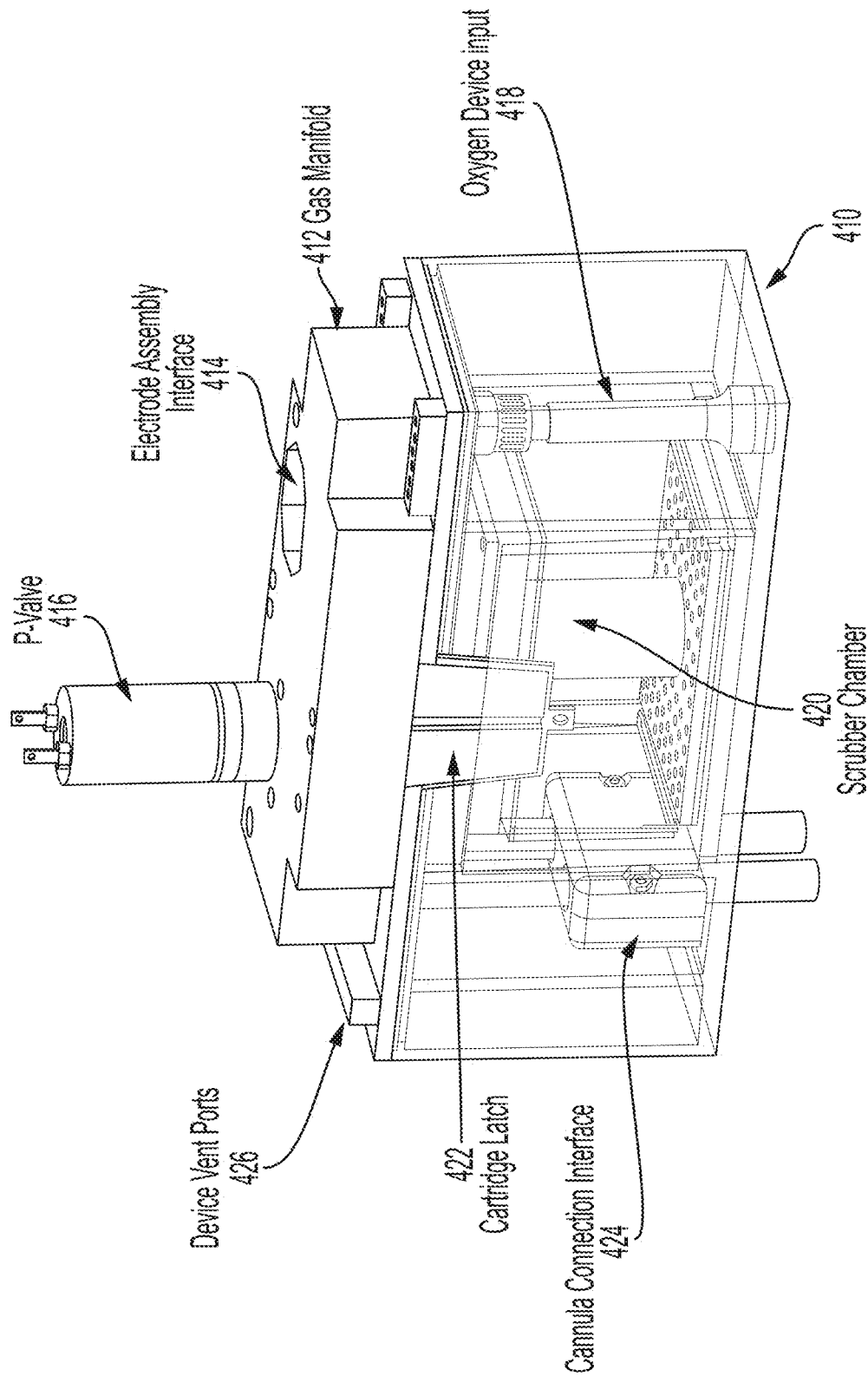
FIG. 27 is an embodiment of a disposable scrubber cartridge and mating pneumatic components for a portable NO generation system.
Figure 28:
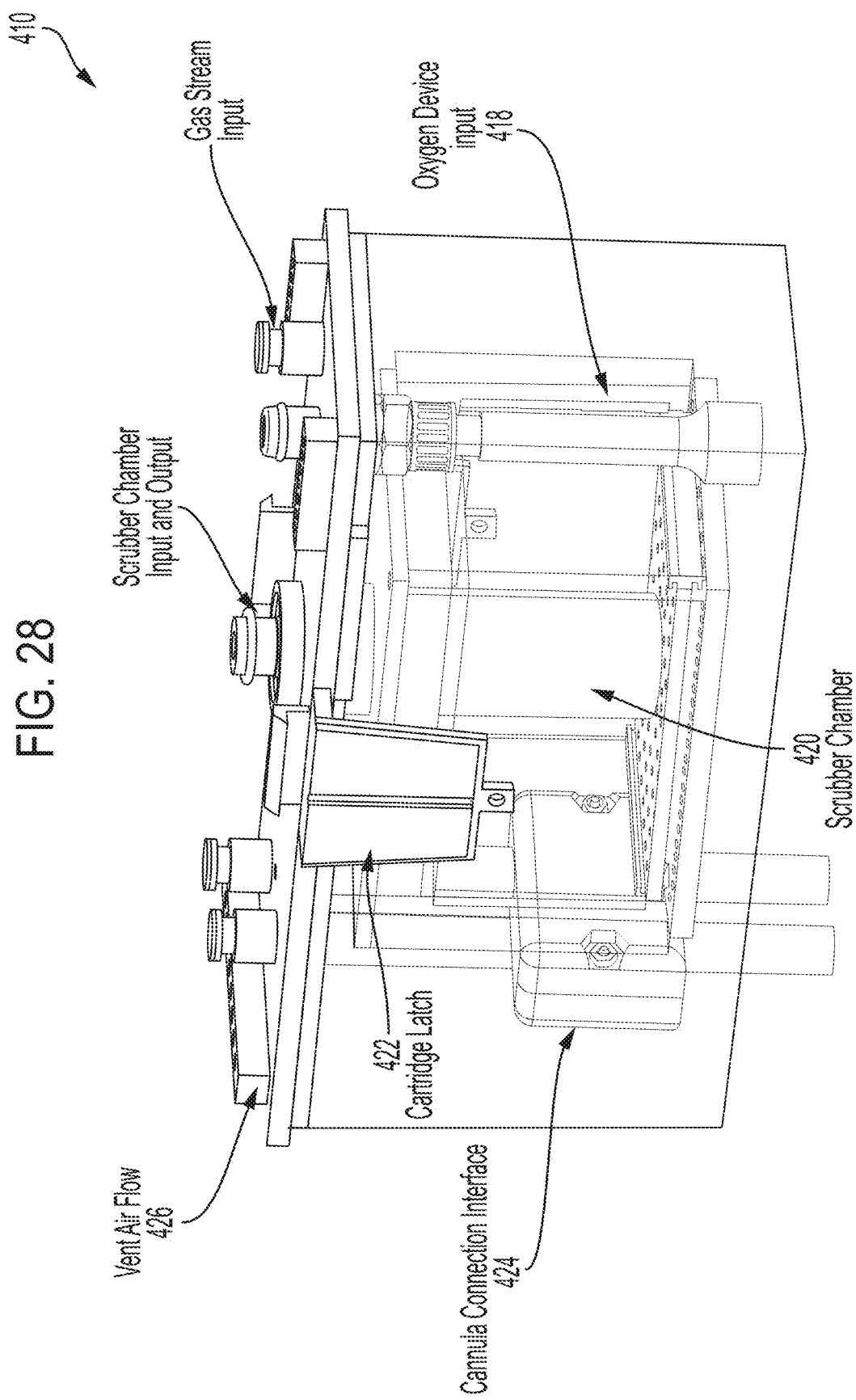
FIG. 28 illustrates the disposable scrubber cartridge of FIG. 27.

FIG. 27 depicts an embodiment of a disposable scrubber cartridge 410 and mating permanent pneumatic components for a portable NO generation and delivery system. At the top of the figure, there is a reusable manifold 412 with an electrode assembly interface 414 and proportional valve 416 attached. The lower portion of the figure shows the disposable scrubber cartridge 410 which includes $O_2$ connections 418, a scavenger chamber 420, a cartridge latch 422, one or more cannula connection lumens 424, and vent ports 426 for controller cooling. FIG. 28 depicts the disposable scrubber cartridge 410 of FIG. 27 alone, without the reusable manifold shown.

Figure 29:
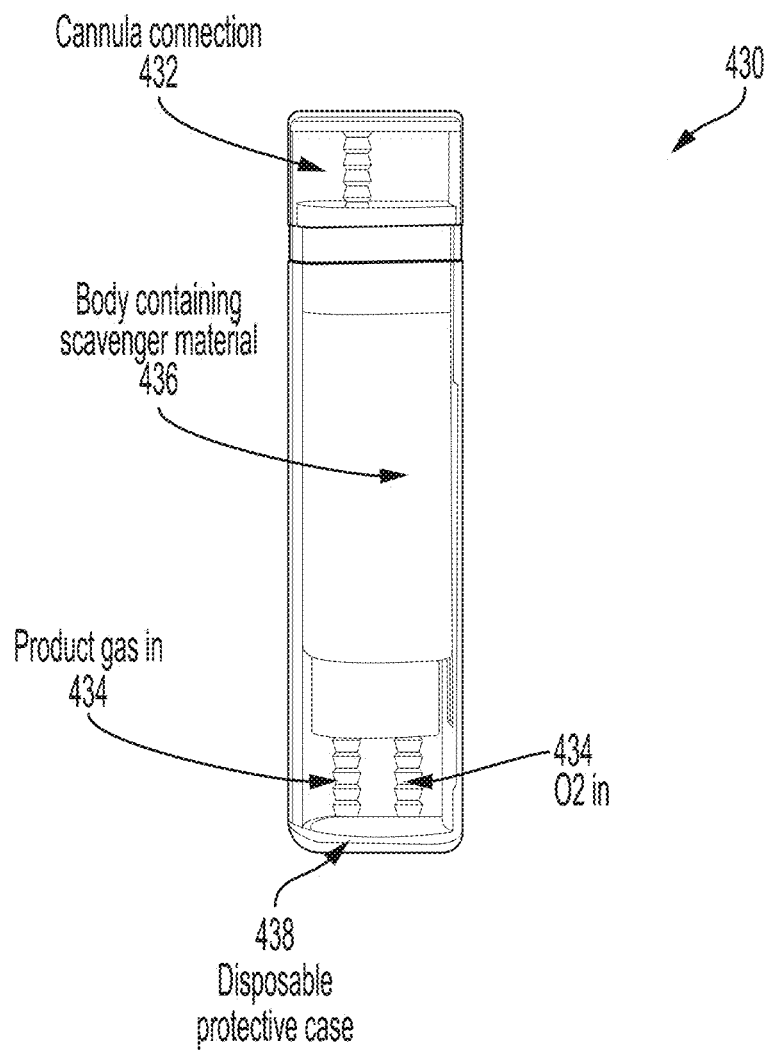
FIG. 29 depicts an embodiment of a scavenger cartridge.

FIG. 29 depicts an embodiment of a scavenger cartridge 430. The scavenger cartridge receives product gas and oxygen from the device through independent pneumatic connections 434. The product gases are scrubbed within the cartridge body 436 by flowing over soda lime or another selective $NO_2$ absorbing material. After scrubbing, the product gases are filtered and merged with the $O_2$ before exiting the system in a single cannula connection 432. In some embodiments, the $O_2$ and NO product gases exit in separate connections. The scavenger cartridge is shown inside an air-tight translucent case 438 that protects the scavenger material from impact and $CO_2$ during transport and storage.

In some embodiments, the controller can detect the presence of a cartridge by any mechanism, including but not limited to electronic, optical, radio or mechanical means. In an embodiment, the controller does not activate the NO generation unless a cartridge is present. In an embodiment, the controller can determine whether or not a cartridge has exceeded the cartridge shelf life by reading information from the cartridge using, for example, a bar code on the cartridge and or interrogating a memory device (e.g. RFID tag) located on the cartridge. In some embodiments, the controller marks the time that a cartridge is inserted and limits the service life of the cartridge to a set amount of time from cartridge insertion and/or a set amount of NO molecules passed through the cartridge. The cartridge can also have inputs for sources of other gases (such as $O_2$) to measure flow rate, or to mix with air for synthesis of NO or for patient delivery (such as Helium).

Electrodes

Figure 30:
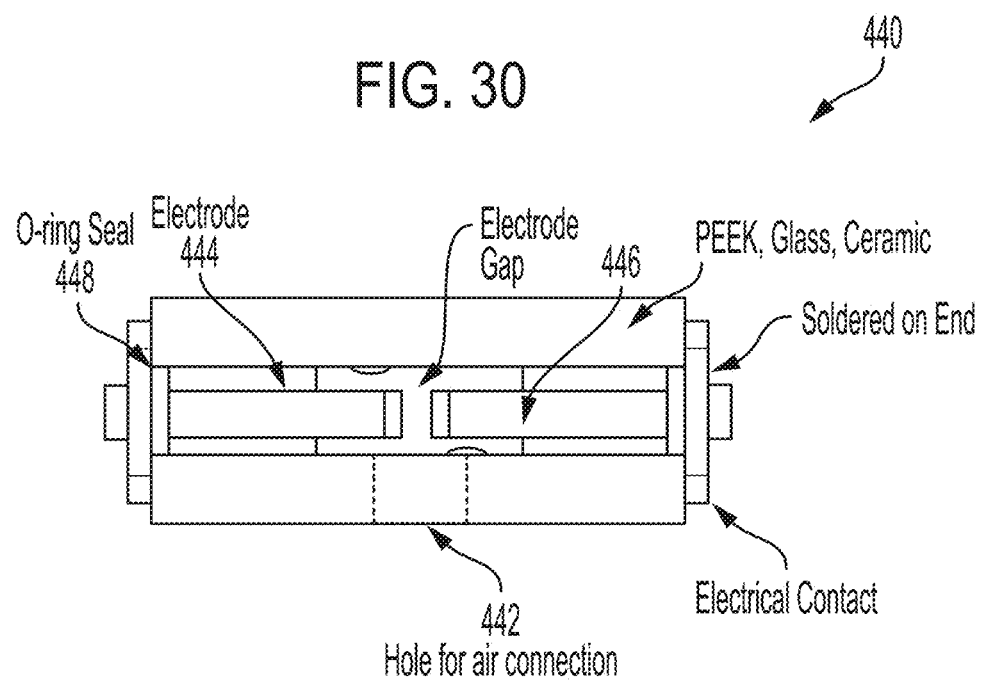
FIG. 30 is an embodiment of an electrode assembly for generating NO in an NO generation system.
Figure 31:
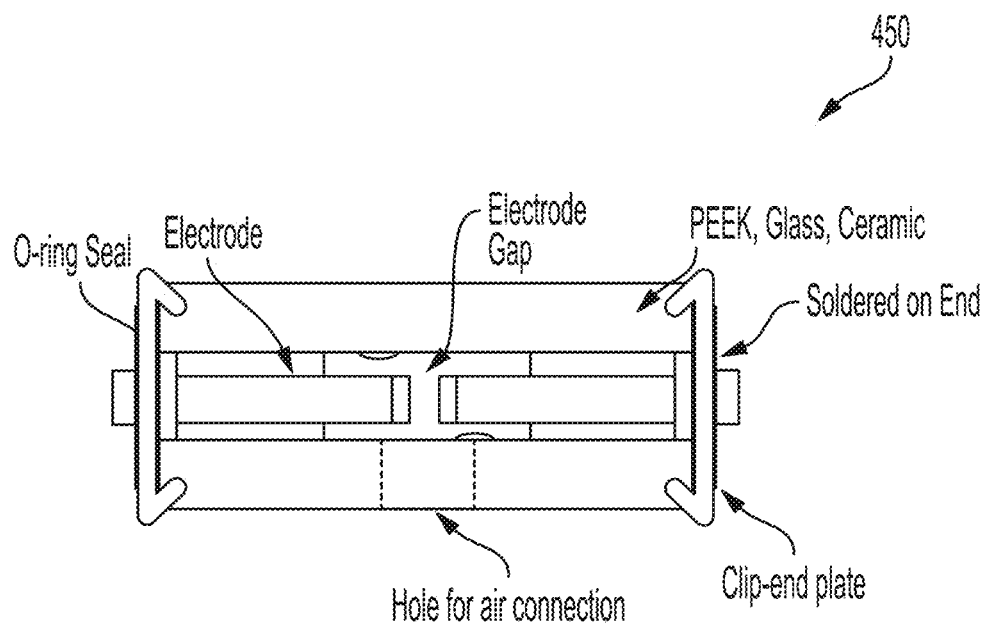
FIG. 31 is an embodiment of an electrode assembly for generating NO in an NO generation system.

Various electrode designs can be used for NO generation. In some embodiments, automotive-style plugs can be used for NO generation, however they can include resistors and more mass and strength than required. An automotive spark plug is designed for strength with a ceramic insulator and heavy metal ground electrode. In the interest of cost and mass, a custom high voltage electrode is desirable. FIG. 30 shows a high voltage electrode 440 that can be manufactured and installed easily. FIG. 30 illustrates an embodiment of an electrode assembly with a blind hole 442 (dashed lines at bottom). Composite electrodes 444, 446 can be inserted into the ends (right and left). In some embodiments, the electrode assembly of FIG. 30 can be manufactured creating composite electrodes by fusing iridium (or other noble metal or alloy) pads to a metallic shaft (for example, copper). O-rings 448 can be inserted into each end of a sleeve. The sleeve can be constructed from PEEK, glass, ceramic or another inert, non-conductive material. Electrodes are inserted through the O-rings from either end into a sleeve. A gap tool is inserted into the hole for air connection. End plates are slid onto each shaft. Electrodes are lightly pressed from either side against the gapping tool. End plates are soldered to the shafts, locking in the gap. The electrodes can be held in place using a variety of techniques, including but not limited to an interference fit, adhesive, threaded fastener, and other means. In an embodiment, the end plate can mechanically snap on to the end of the glass sleeve as shown in FIG. 31, which illustrates an embodiment of an electrode assembly 450 with end plates that clip to the sleeve and solder to the electrodes.

Having a single hole for air connection enables the user to insert an electrode assembly from one side with a single action. Various types of retention features can be used, including but not limited to detents, snaps, clamps and other means, to keep an electrode assembly in position within a controller. In another embodiment, there are two pneumatic connections to the electrode assembly from the same side to facilitate installation and removal.

A custom electrode assembly can interface with a controller by registering the electrodes with electrical contacts in the controller. A dual-lumen nipple from the controller can be inserted into the hole in the side of the electrode assembly to deliver air and remove NO-laden air.

Figure 32:
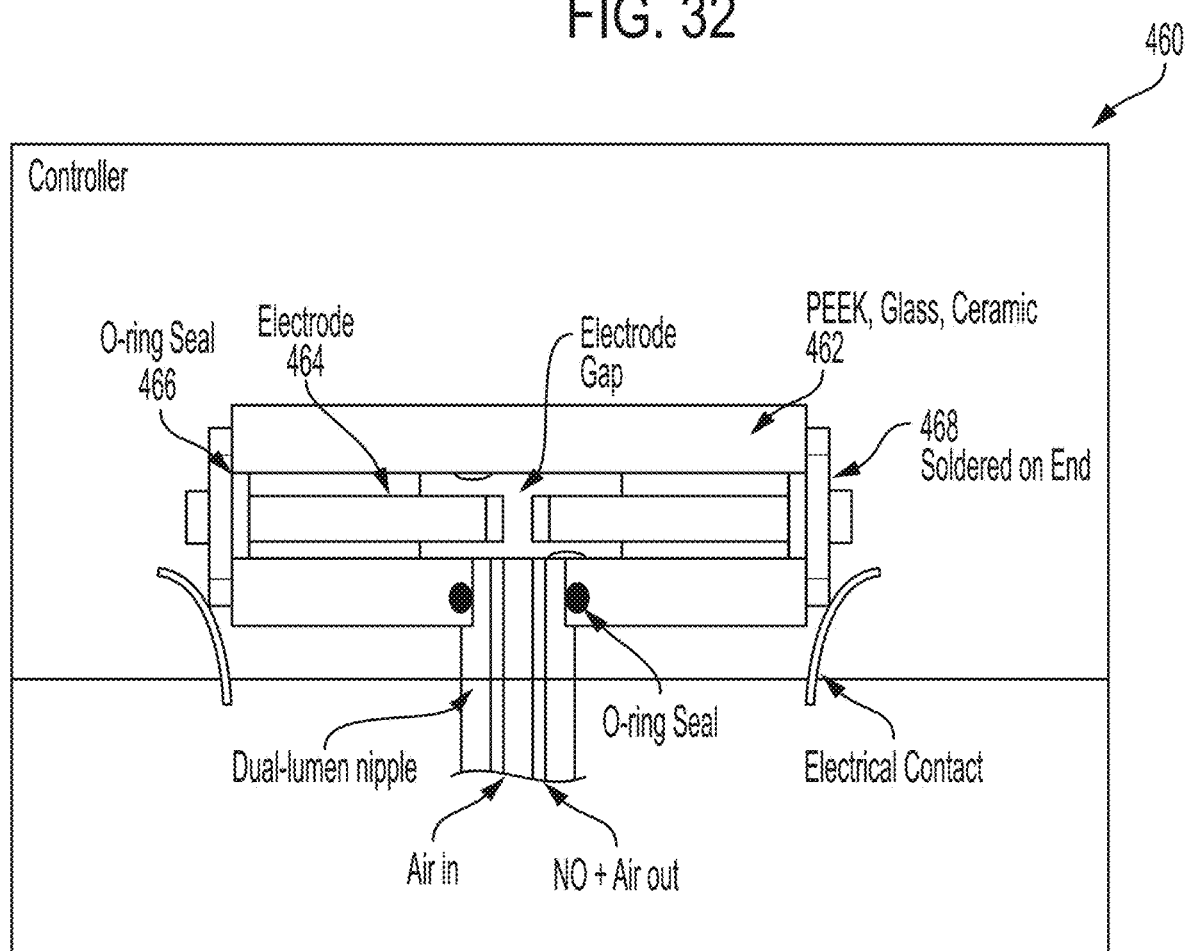
FIG. 32 is an embodiment of an electrode assembly for generating NO in an NO generation system.
Figure 33:
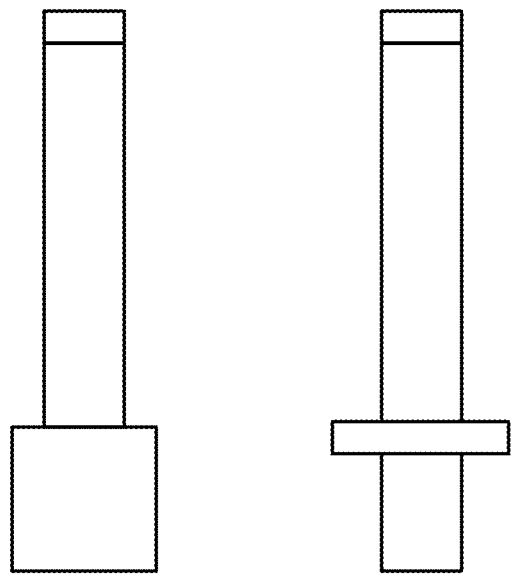
FIG. 33 illustrates various embodiments of electrodes with features for bottoming out.

FIG. 32 illustrates an embodiment of an electrode assembly 460 comprising a sleeve 462, a composite electrode 464 (copper shaft with iridium pad), O-ring seals 466, and end plates 468. The electrode assembly 460 can be inserted into a controller with high voltage electrical contacts contacting each end of the electrode assembly and a dual-lumen nipple inserted into the air connection hole. The composite electrode may have a step in the diameter, flange or other feature that makes the electrode bottom out into a hole at a specific depth. FIG. 33 illustrates embodiments of electrodes with features for bottoming out.

Figure 34:
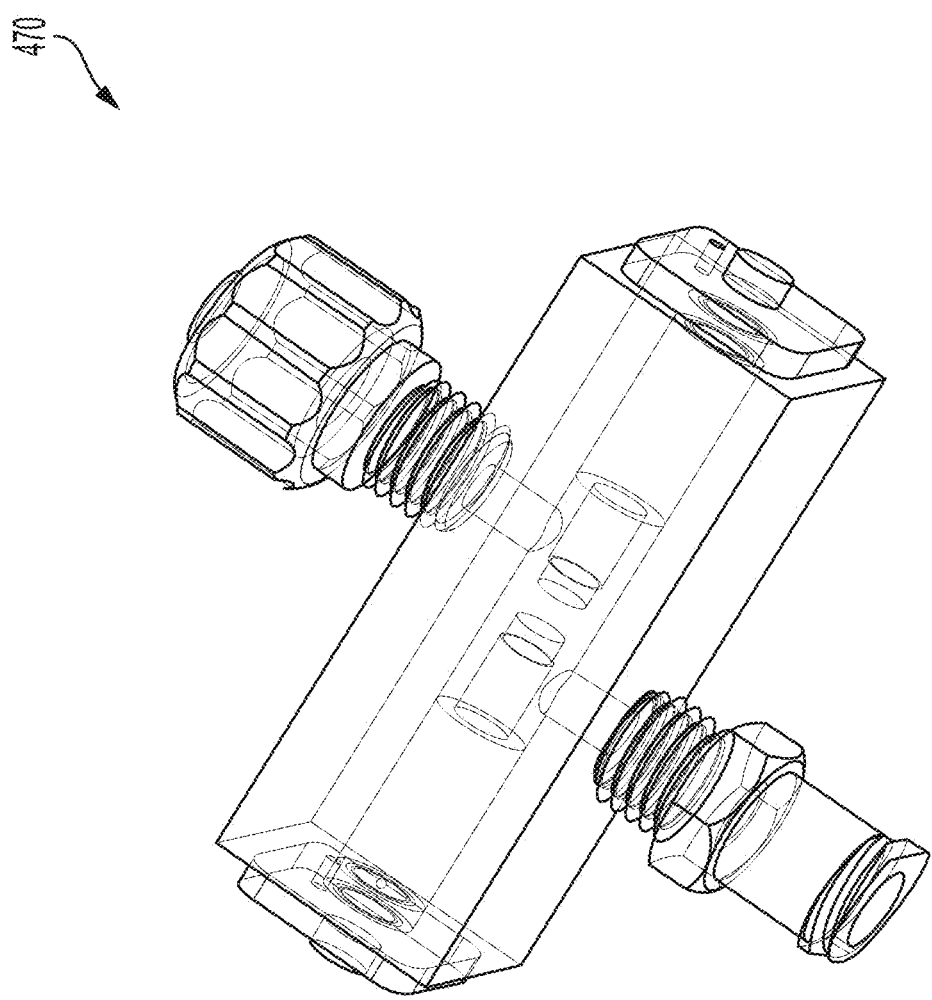
FIG. 34 is an embodiment of an electrode assembly that allows for air flow across an electrode gap.
Figure 35:
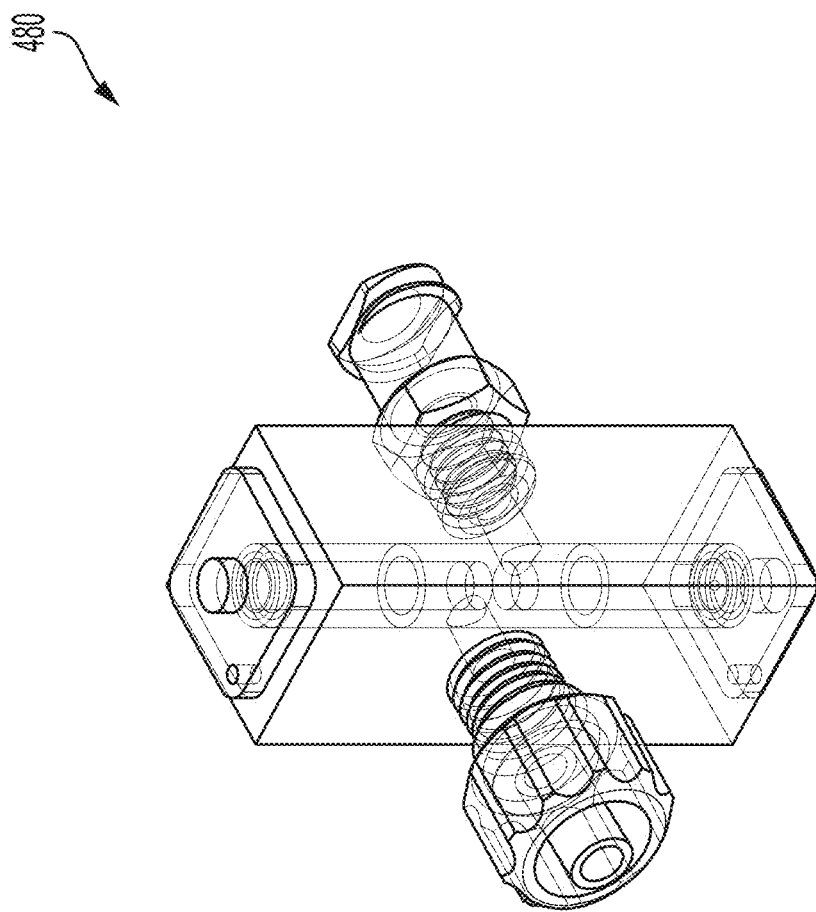
FIG. 35 is an embodiment of an electrode assembly.

In an embodiment, flow of air through the electrode assembly goes across the electrode gap. FIG. 34 illustrates an embodiment of an electrode assembly 470 showing air inlets (bottom left and upper right). Air flows into the electrode assembly on one side and out the opposing side. FIG. 35 illustrates an embodiment of a cross-flow electrode assembly 480 showing end-plate geometry. The hole in the corner of the end plate can be used for soldering a wire to it or fastening the end plate to the sleeve with a threaded fastener. The corners of the end plate can be rounded to reduce the potential of electrical discharge from the end plate.

Air flow within the electrode assembly can be from one side to the other, as shown in FIG. 35. In an embodiment, the flow can be from one side to an adjacent side. In an embodiment, air enters from one side, travels axially in parallel with the electrodes and then exits from the same side. This design shares the benefit of being inserted with a single action.

Figure 36:
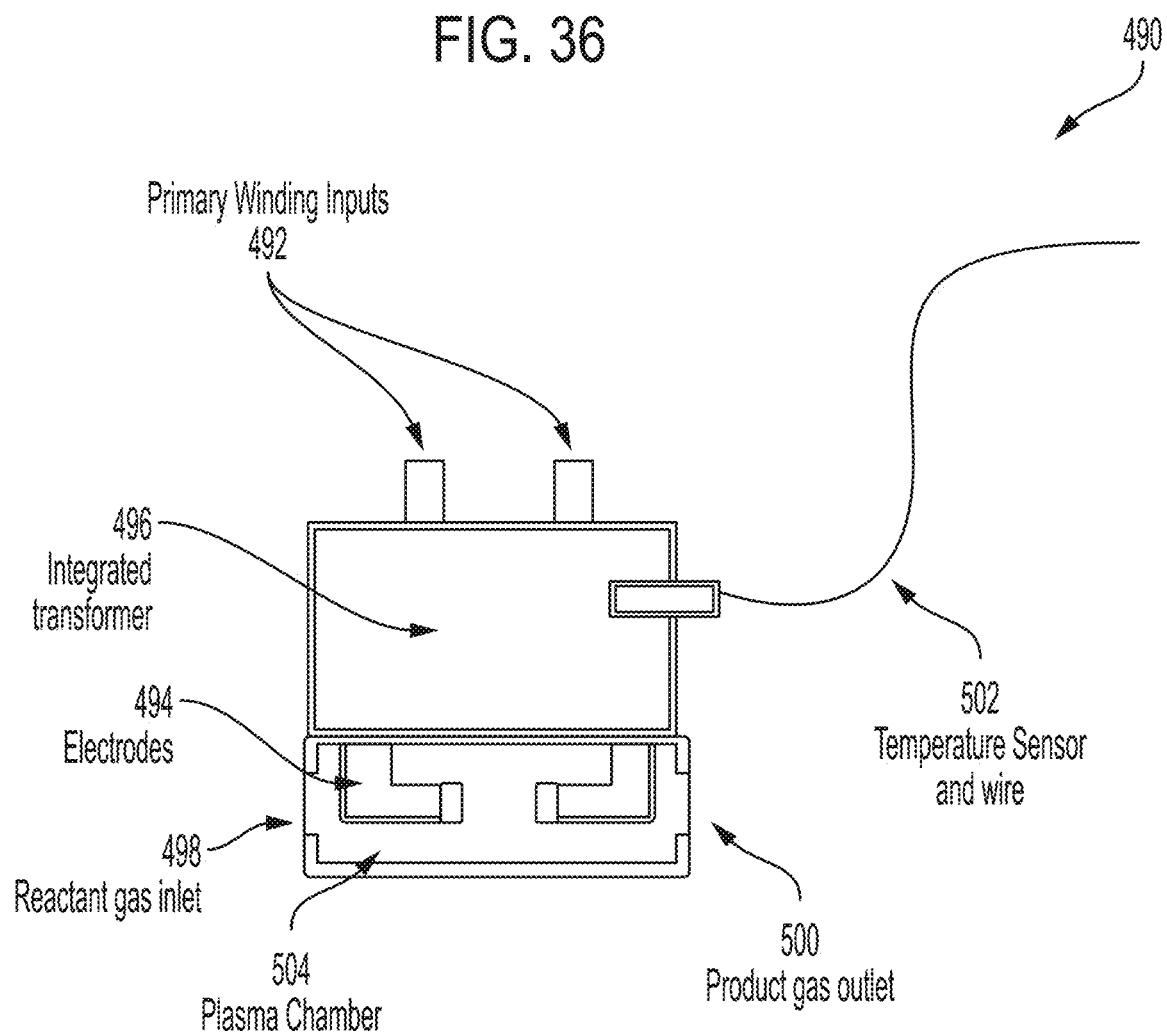
FIG. 36 depicts an embodiment where the electrodes, high voltage transformer and plasma chamber are integrated.

FIG. 36 depicts an embodiment where the electrodes, high voltage transformer and plasma chamber are integrated. This provides the benefit of reducing the volume and mass for these components as well as shortening the length of high voltage conductors, thereby decreasing electromagnetic emissions. In another embodiment, the electrodes and transformer are potted together to form a single unit that is removably coupled with the plasma chamber.

FIG. 36 depicts an integrated transformer/electrode assembly/plasma chamber 490. Primary winding inputs 492 are located at the top of the transformer. In one embodiment, the windings on the primary are made with Litz wire. Secondary winding outputs are electrically connected to electrodes 494. The transformer 496 and electrodes are potted within insulation material with the electrode gap maintained by the insulation material. The potted transformer and electrodes are connected with an air-tight seal to a plasma chamber 504. The plasma chamber has a reactant gas inlet 498 and an a product gas outlet 500. A temperature sensor 502 is potted within the insulation material or otherwise thermally connected to the transformer for a NO generation and delivery system to detect overheating of the transformer and respond accordingly with one or more of generating an alarm, decreasing the power delivered to the transformer, transitioning to a back-up transformer, increase the speed of a cooling fan, or other means to arrest the increase in temperature).

Manifold Configurations

Figure 37:
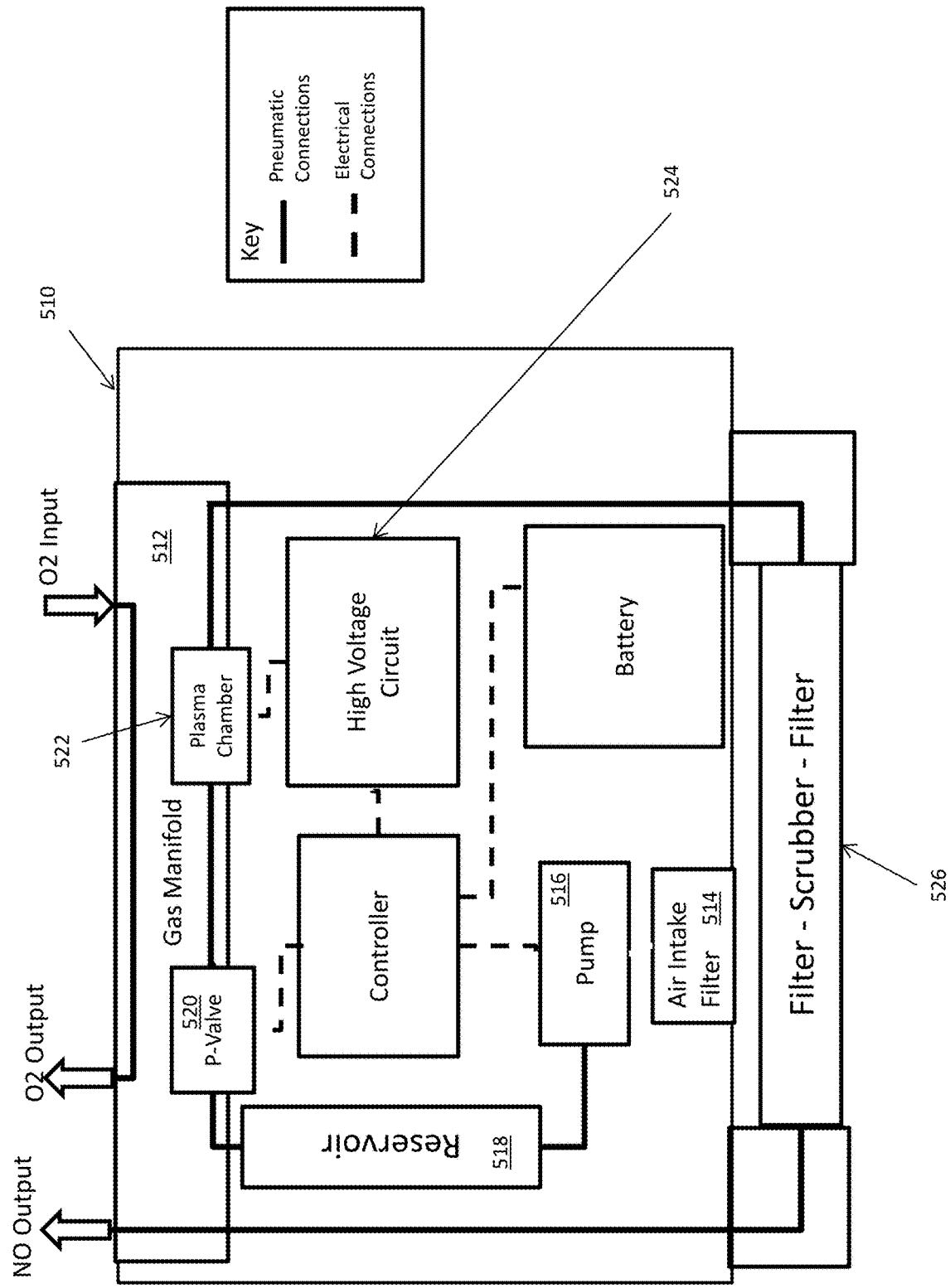
FIG. 37 is an embodiment of a portable NO device with a manifold affixed to one of the side walls of the device enclosure.

FIG. 37 depicts an embodiment where a manifold 512 is affixed to one of the side walls of the device enclosure 510. In this depiction of the device, air is drawn in from the exterior of the enclosure 510 through a filter 514 to a pump 516. The pump 516 delivers air to a reservoir 518 to pressurize the reservoir. The reservoir is connected to a gas manifold 512 in series with a proportional valve 520. The proportional valve regulates the flow of air into the plasma chamber 522. The electrodes within the plasma chamber are driven by the high voltage circuit 524 within the enclosure. After passing through the plasma chamber, the gas is fed through a filter, scrubber and a second filter 526. After the filter-scrubber-filter 526, the gas then returns to the manifold where it exists through a fitting to a cannula or other delivery device. The gas manifold also features an input connection and output connection to enable parallel use of an oxygen source. In one embodiment, a parameter within the $O_2$ line is measured as an indicator of inspiration and/or $O_2$ delivery. The parameter could be one or more of the following: $O_2$ line pressure, $O_2$ line flow, $O_2$ line temperature, $O_2$ tube wall strain, or other parameters. The device is powered by a battery. In some embodiments, the battery is built in, while it is removable in other embodiments. The system is also capable of running off power from an external source, such as an external battery pack, automotive power supply (cigarette lighter), AC power converter and the like.

Figure 38:
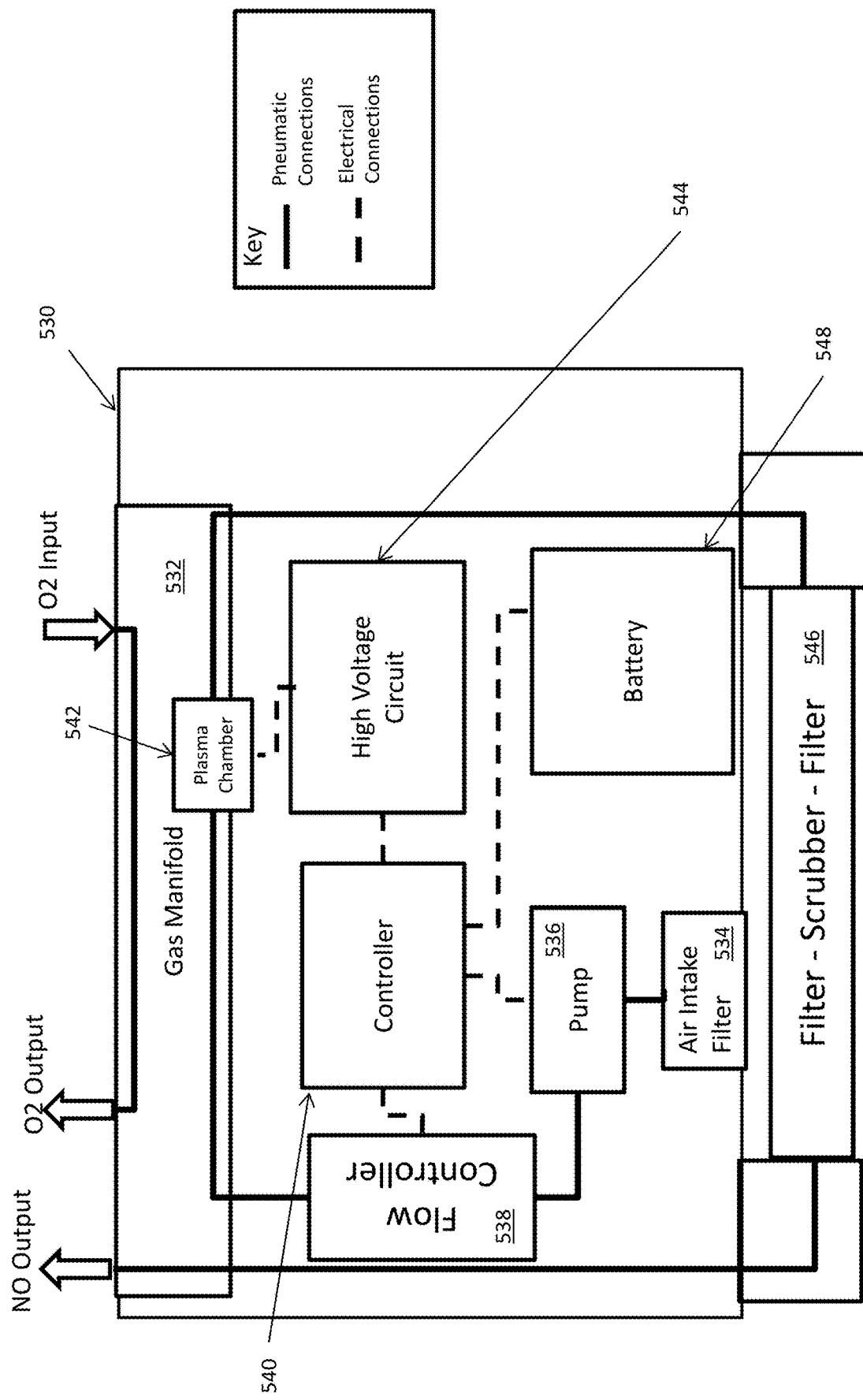
FIG. 38 is an embodiment of a portable NO device with a manifold affixed to one of the side walls of the device enclosure.

FIG. 38 depicts an embodiment where a manifold 532 is affixed to one of the side walls of the device enclosure 530. Air is drawn in from the exterior of the enclosure through a filter 534 to a pump 536. The pump 536 delivers air into a flow controller 538 which determines the timing and duration of pressurized air delivery into the gas manifold 532. In one embodiment, the gas flow controller consists of one or more valves that are controlled by the controller 540. The controller consists of electronic hardware with software control, however embodiments with no software have also been contemplated. The gas manifold directs the flow into the plasma chamber 542. The plasma chamber is driven by the high voltage circuit 544 within the enclosure. After passing through the plasma chamber, the gas travels to a replaceable scrubber 546 on the exterior of the enclosure 530. After the scrubber, the gas returns to the manifold where it is then passed through a connector into cannula or other delivery device. The gas manifold also has a set of input and outputs to allow for parallel use with oxygen delivery. The device is powered by a battery 548 within the enclosure 530.

Figure 39:
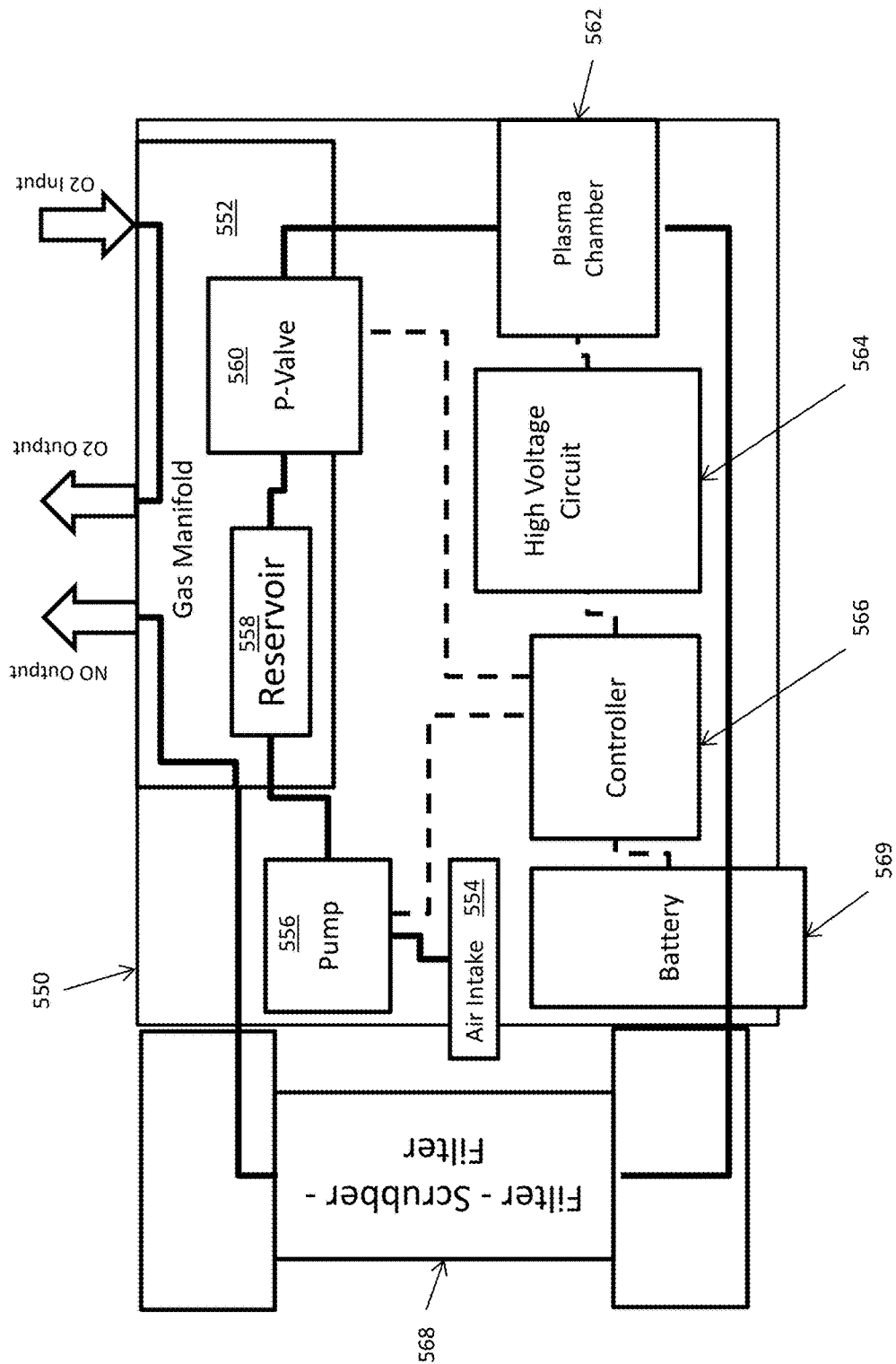
FIG. 39 is an embodiment of a portable NO device with a manifold affixed to a back wall of the device enclosure.

FIG. 39 depicts an embodiment where a manifold 552 is affixed to the back wall of the device enclosure 550. In this depiction of the device, air is drawn in from the exterior of the enclosure through a filter 554 to a pump 556. The pump feeds air into an integrated pressurized reservoir 558. The reservoir consists of a volume within the manifold. Gas release from the reservoir is controlled by a proportional valve 560. The proportional valve regulates the flow into the plasma chamber 562. Electrodes within the plasma chamber (not shown) are driven by the high voltage circuit 564 connected to controller 566 within the enclosure. After passing through the plasma chamber, the gas travels to a replaceable filter-scrubber-filter assembly 568. After the scrubber, the gas then returns to the manifold where it exits the system through a fitting and into a delivery conduit such as a nasal cannula. The gas manifold also has a set of input and outputs to allow for parallel use of oxygen therapy. The battery 569 is removable in this embodiment.

Figure 40:
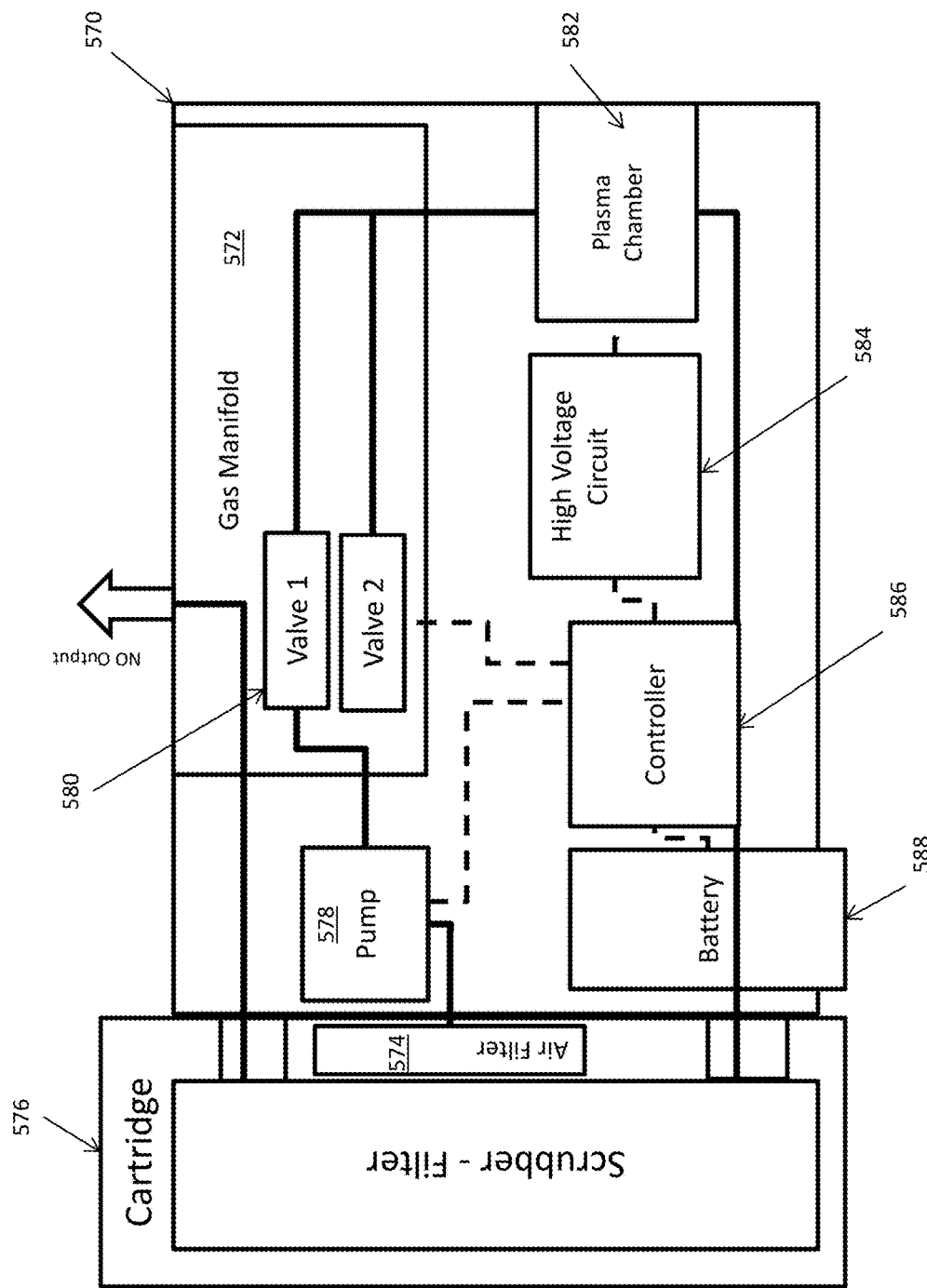
FIG. 40 is an embodiment of a portable NO device with a manifold affixed to a back wall of the device enclosure.

FIG. 40 depicts an embodiment with a manifold 572 affixed to the back wall of the device enclosure 570. Air is drawn in through a filter 574 in a removable cartridge assembly 576 to a pump 578. The pump directs air to an array of valves 580 mounted to the manifold which control the flow rate of pressurized air delivery into the gas manifold. The gas manifold 572 directs the flow to a plasma chamber 582 that is separate from the manifold. Electrodes within the plasma chamber are driven by the high voltage circuit 584 which is controlled by the controller 586 within the enclosure. After passing through the plasma chamber the gas is fed through pneumatic couplings to the removal cartridge where the gas passes through scrubber material and a filter. After the scrubber the gas then returns to the device through a pneumatic coupling to the manifold 572 where it is exits the device through a fitting to the patient delivery tube. This figure depicts an embodiment that does not interface with the flow of $O_2$, so $O_2$ fittings are not required. The device is powered by one removable battery 588.

Figure 41:
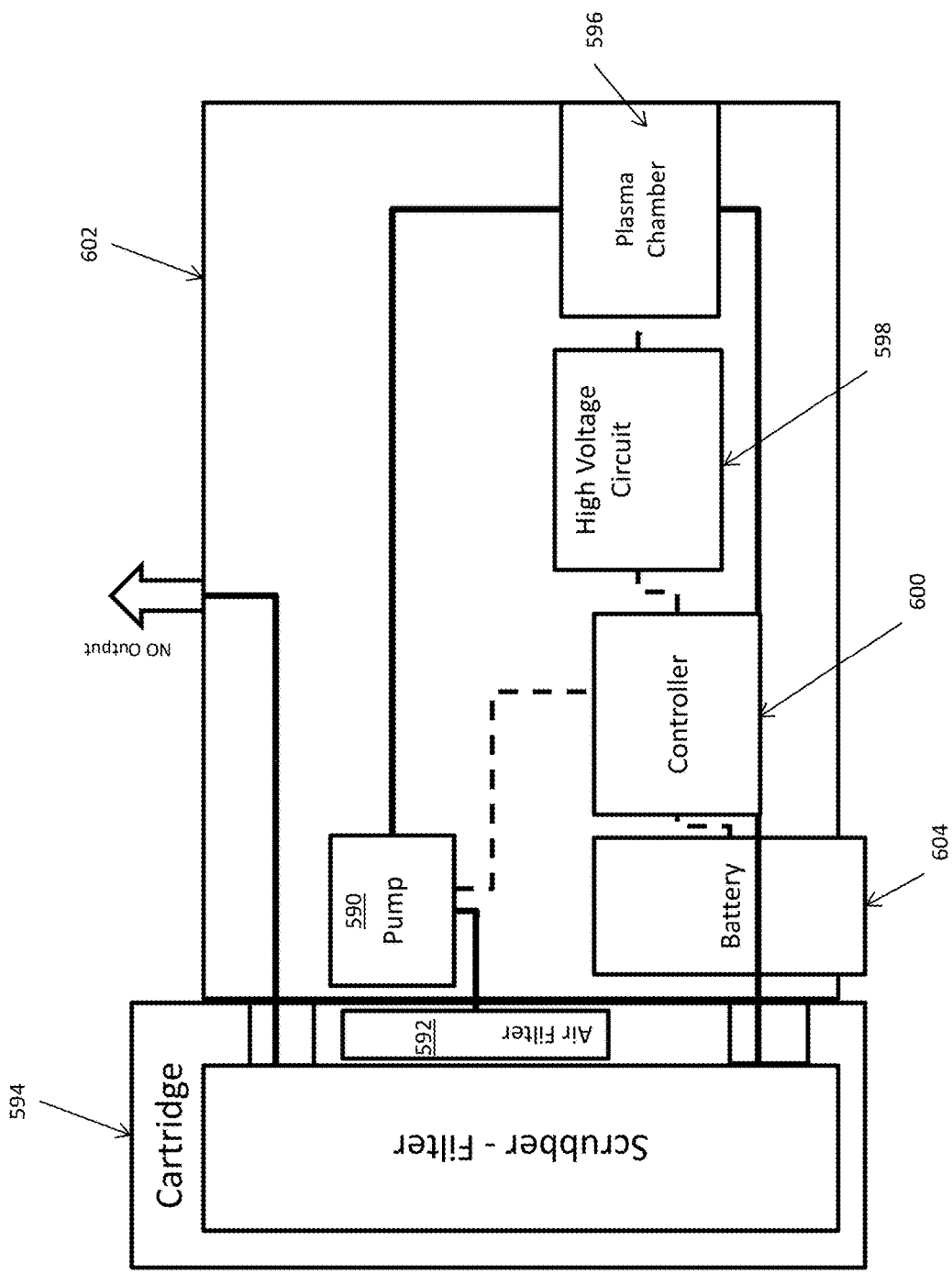
FIG. 41 is an embodiment of a portable NO device with no manifold or gas flow control other than a pump.
Figure 42:
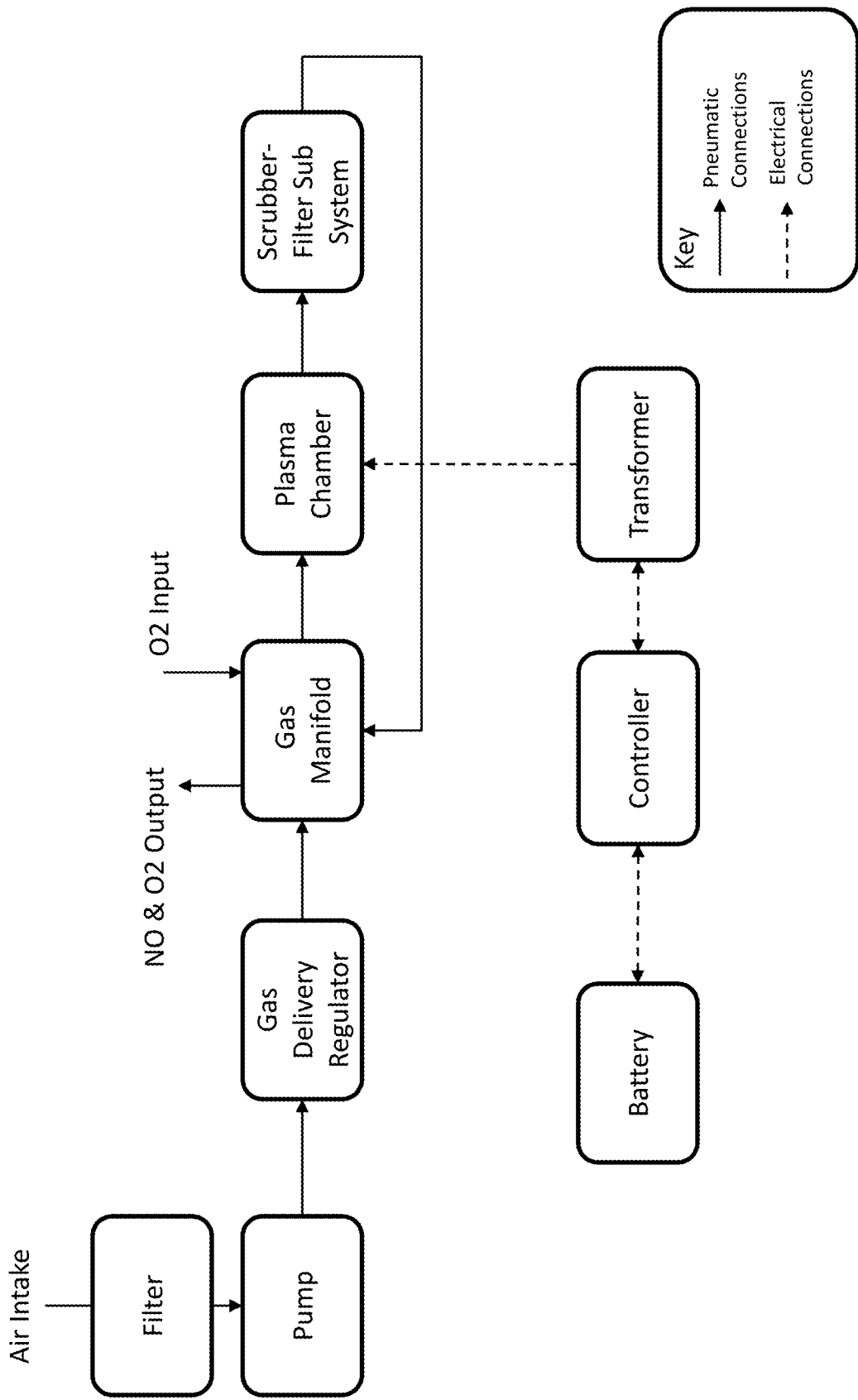
FIG. 42 is an electrical and pneumatic layout of an NO generation system.

FIG. 41 and FIG. 42 depict an embodiment with no manifold or gas flow control other than the pump 590. Air is drawn in through a filter 592 in a removable cartridge assembly 594 to a pump 590. The pump directs air to a plasma chamber 596. Electrodes within the plasma chamber are driven by the high voltage circuit 598 which is controlled by the controller 600 within the enclosure. After passing through the plasma chamber the gas is fed through pneumatic couplings to the removal cartridge 594 where the gas passes through scrubber material and a filter. After the scrubber, the gas then returns to the device enclosure 602 and exits the device through a fitting to the patient delivery tube. The device is powered by one removable battery 604.

User Interface and Connectivity

Figure 43:
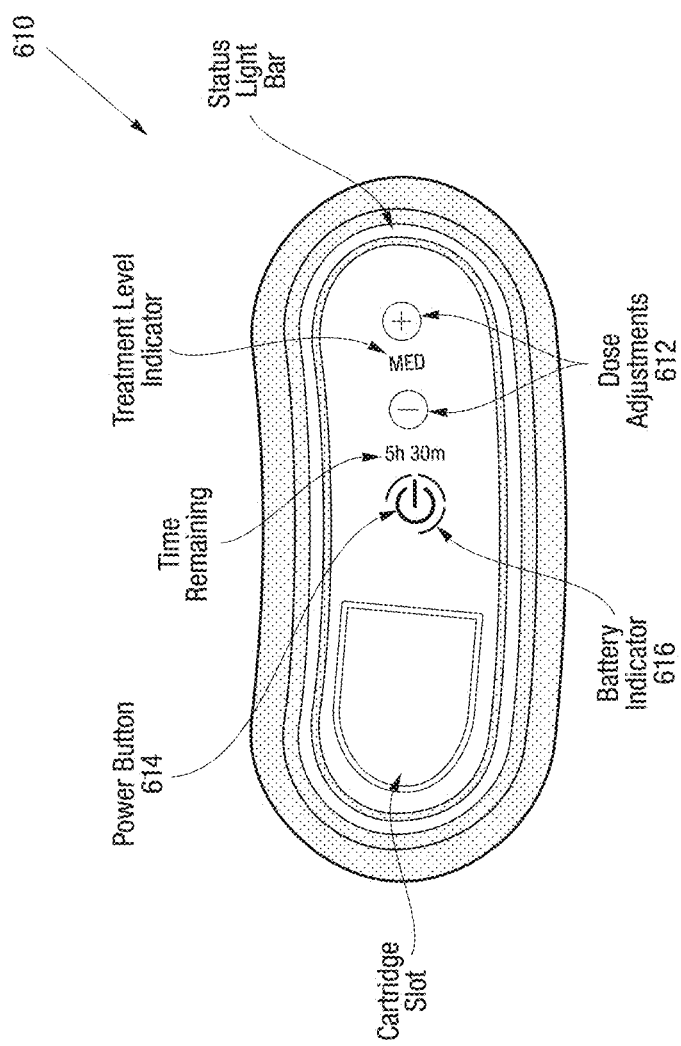
FIG. 43 is an exemplary user interface for use with an NO generation system.

A user interface can be used to display various information relating the functionality of the device and patient information. In some embodiments, an ambulatory NO device 610 can have a user interface that can include a variety of features as shown in FIG. 43. In some embodiments, the user interface includes an NO increase button 612. In some embodiments, the user interface includes an NO decrease button 612. In some embodiments, the user interface includes a panic button that can be used to notify an external source (for example, rescue personnel) of a life-threatening situation and the system can communicate to the outside world through one or more of a wireless or wired connection to a base station, the cellular network or a Wi-Fi connection to the internet. In some embodiments, the user interface includes a power button 614 that can turn the device on/off. In some embodiments, the user interface includes a boost button that can be used to increase NO production from current levels for a set amount of time, such as 5 minutes, a battery charge level indicator 616, and a cartridge life indicator.

Figure 44:
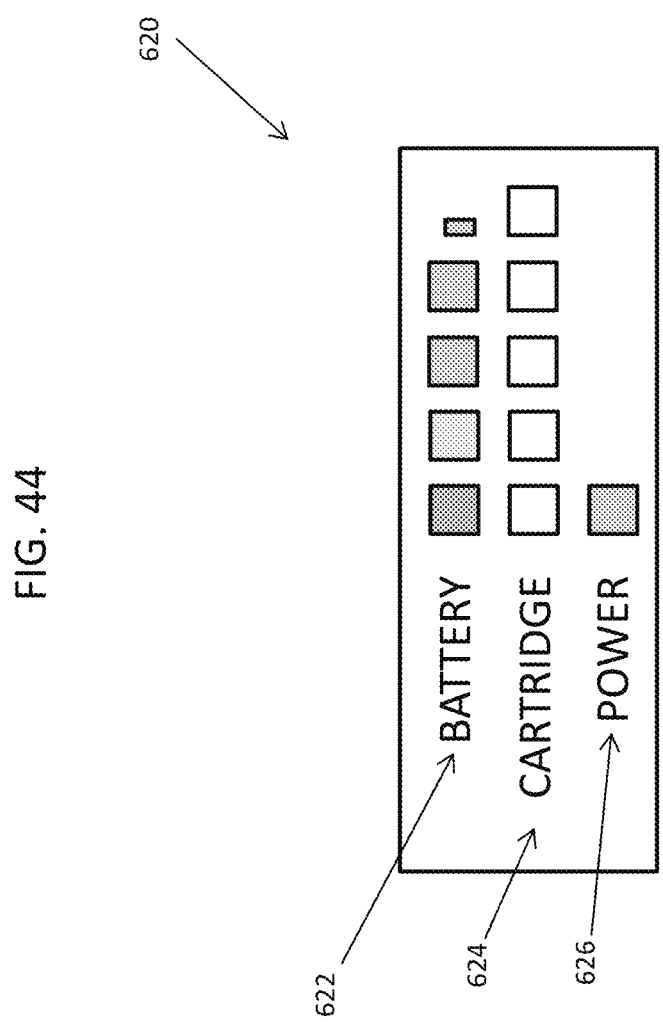
FIG. 44 is an exemplary user interface screen for displaying status indicators relating to battery life, cartridge life, and power.

A user interface 620 can include one or more LED indicator lights, as shown in FIG. 44, that be used to indicate a variety of information, including but not limited to power 626, battery status 622, and remaining cartridge life 624. In some embodiments, the cartridge life can be determined by a variety of indicators, including but not limited to number of NO molecules generated, number of $NO_2$ molecules generated, volume of air containing $CO_2$ flowed through the cartridge, pumping effort (reflective of filter clog status), calendar time since insertion, run time since insertion, $NO_2$ levels in the effluent gas, and color of cartridge life indicator (e.g., Draegersorb®).

Figure 45:
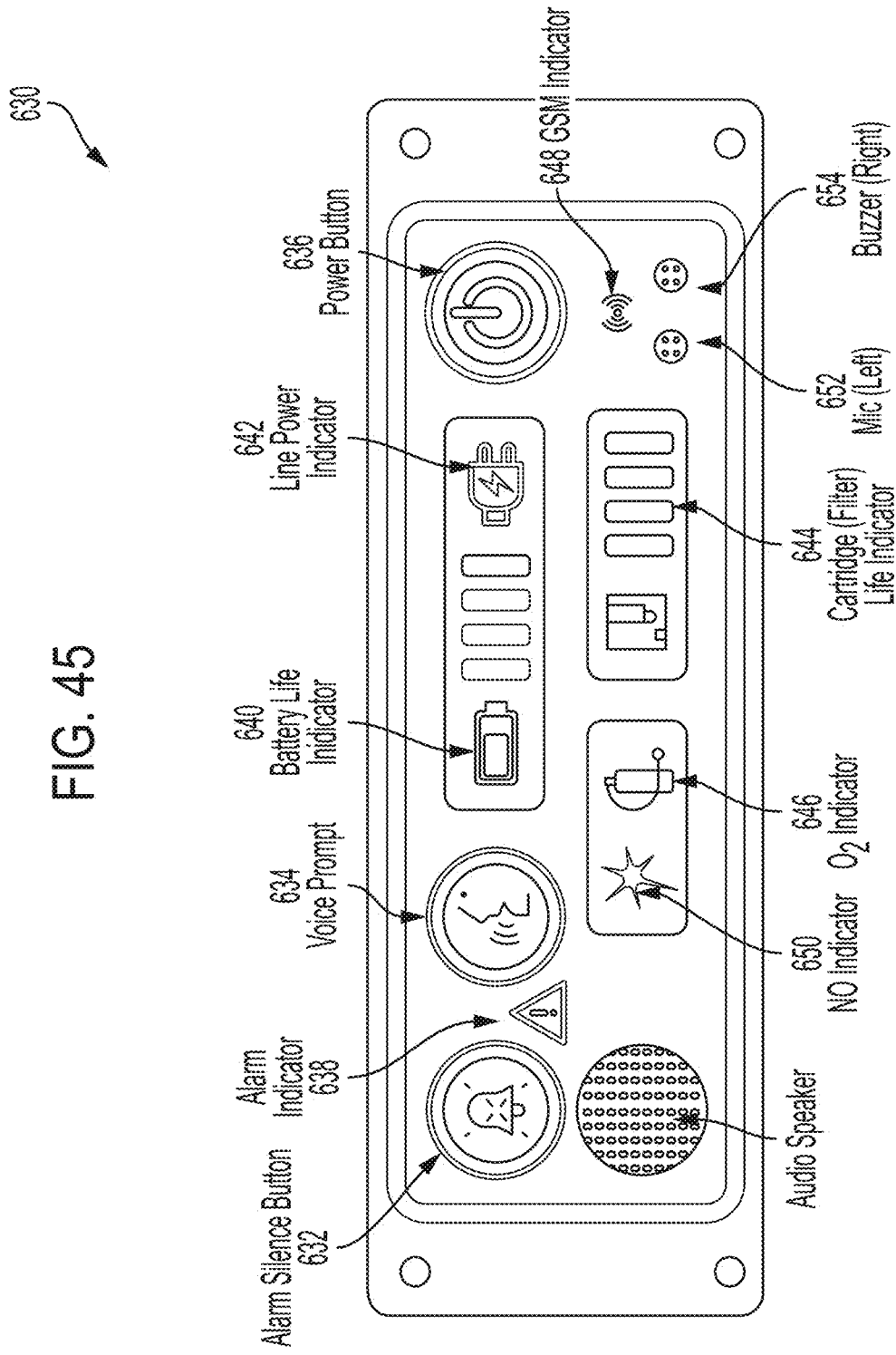
FIG. 45 is an exemplary user interface.

FIG. 45 depicts another exemplary user interface 630. In some embodiments, the user interface 630 can include discrete buttons for alarm silence 632, voice prompt 634, and power 636. Pressing the voice prompt button prompts the device to generate an audible instruction through the speaker (also shown on the user interface). In some embodiments, audible instructions are used to identify alarm conditions, instruct the user on how to respond to alarm, and instruct the user on the device set-up procedure in addition to other instructions to the user. The user interface can also include illuminated indicators for alarm status 638, battery charge status 640, external power connection 642, cartridge remaining life 644, $O_2$ flow detection 646, GSM connection 648, and NO generation 650. The user interface panel also includes a microphone 652 to record user voice inputs and a buzzer 654. In some embodiments, the user interface panel also includes one or more antennae for GSM, Bluetooth, Wi-Fi, and other connectivity. In some embodiments, the user interface can be lifted up to expose the scavenger cartridge insertion slot. In some embodiments, the power button is pressed briefly once to power up the device and held for several seconds to power the device off.

The system can also include alarms to notify the user of various types of information. For example, alarms can be used for a malfunction of the device, such as lack of plasma detected, or a sedentary time limit that notifies the user that they should move around. A light bar on the outside of the NO generation device provides status of the device. For example, a green or blue light can indicate that there are no alarms. A low battery can make the light bar yellow. A low cartridge life remaining could make light bar yellow. A very low battery, very low cartridge life, or lack of plasma activity could turn the light bar red. Alarms can include voice prompt, a bell sound, visual indicators (lights), and haptic events (vibrations).

The system can be remotely configured by an external device (for example, a smart phone, tablet, or Internet-of-Things (IoT) connected device). Configurable settings include one or more of the following: boost settings, dose increments, dose limits, alarm limits, exercise algorithm (duration, step increase in NO), and/or patient sleep settings.

Figure 46:
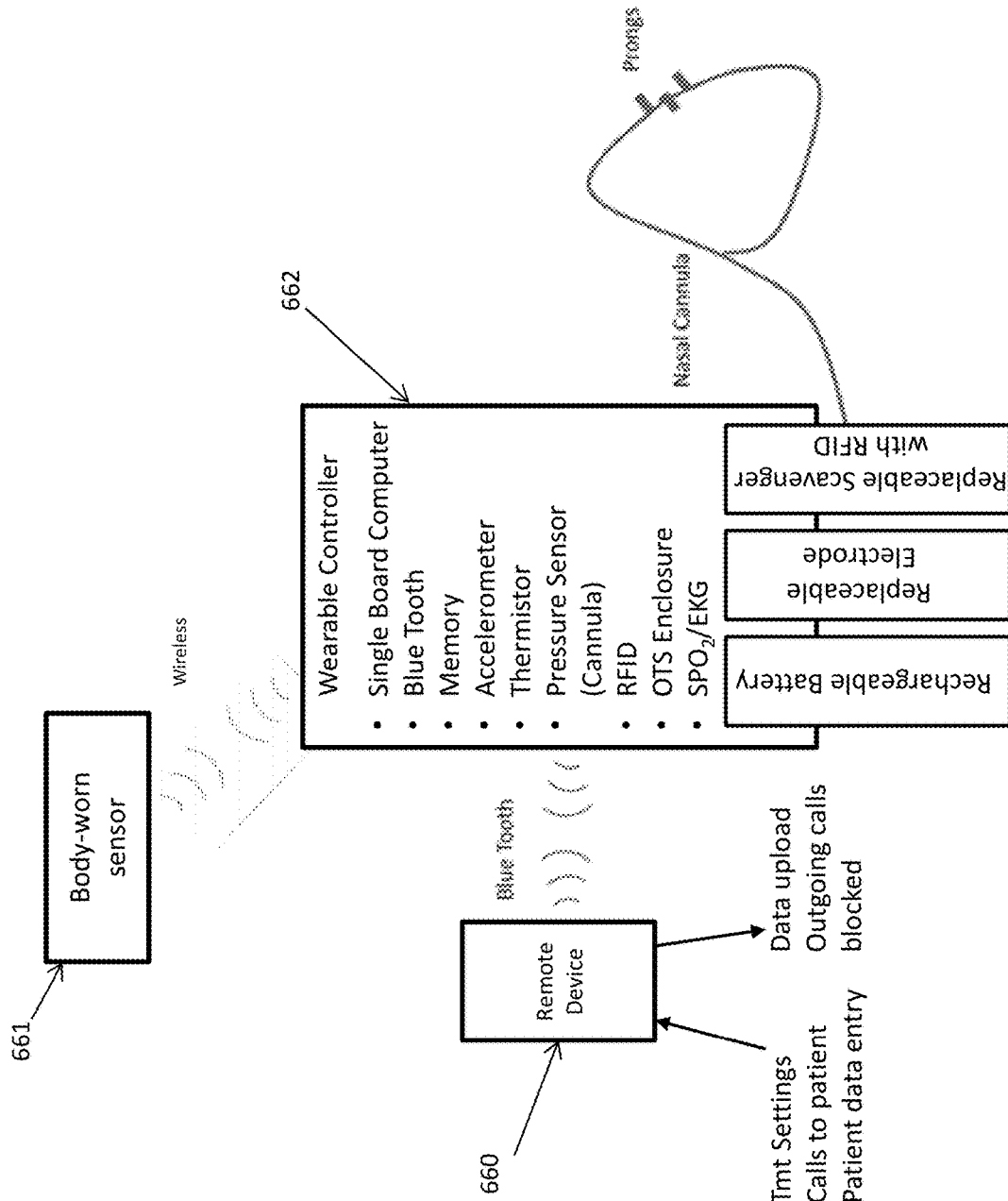
FIG. 46 is an embodiment of an NO generation system that is in communication with an external device.

FIG. 46 illustrates an embodiment of a system that uses a remote device 660 as a graphical user interface, physician interface, and primary patient interface. It will be understood that any external device with a screen or display can be used to communicate with the NO generation device and provide a user interface for information from the NO generation device 662 to be displayed to a user. Examples of a remote device include a tablet computer, smart phone, automobile computer, or smart watch.

In some embodiments, the NO generation device can be designed without any software such that the device can include a power source (for example, a battery), one or more high voltage circuits, a timing circuit, one or more electrodes, a pump and a scavenger. The system can deliver either a fixed flow of air with a fixed concentration of NO or pulses of NO. For example, 1 lpm of air with 20 ppm NO can be used. This streamlined design can also include a buzzer and a red light to notify the user if plasma is not detected. In an embodiment, a lack of plasma activity can be detected when the manifold temperature goes below a temperature threshold. In some embodiments, the device does not include a mechanical pump for air, and instead, air can be pulled through the system via Bernoulli effect, venturi effect, other mixing process or specialized mixing valve from passing $O_2$ as it flows to the patient. In some embodiments, an NO delivery controller can have a very minimal user interface consisting only of battery status, NO level, and alarm indicator. The controller can interface with a secondary device, for example a smart phone. The secondary device can be used to provide a graphical user interface, receive patient inputs, receive physician inputs, store data, communicate with the patient, monitor other physiological parameters (for example, respiratory rate and/or heart rate) communicate with a physician, and/or communicate with emergency personnel, and/or communicate physiological parameters and user inputs to the NO generation device. In some embodiments, an optical fiber resides either within or immediately adjacent to a cannula. The optical fiber extends into the patient nostril and is used to measure $SpO_2$, respiration rate, heart rate and other physiologic factors by optical means. In some embodiments, breath is detected at the distal end of the optical fiber by detecting changes in the reflectivity of the end of the fiber as humidity from exhaled gases condense on the end of the fiber during patient exhalation.

In some embodiments, an NO generation device is used with a smartwatch. The smart watch provides a wearable remote user interface, which facilitates user interaction with the NO device and/or an $O_2$ concentrator when the NO device and concentrator are not easily reached (e.g. NO generation device in a backpack). Patient physiological and activity data measured by the smartwatch or entered into the smartwatch by the user can be utilized in the control of NO and $O_2$ therapy. For example, when an increase in user activity is detected by the smartwatch (e.g. increased heart rate, accelerations indicating ambulation, etc.), the smartwatch can communicate to the NO and $O_2$ devices to increase the delivered concentration of NO and $O_2$, respectively.

Similar connectivity can be accomplished by a smartphone/tablet application. The larger display of a smartphone/tablet can provide additional information, such as trending data, a dashboard, step count, etc. The larger processor and increased connectivity of a smart phone or tablet can enhance treatment with more complex algorithms, cloud-connectivity, remote assistance, and other features. Treatment, physiologic and activity data can be stored on a remote device, such as a smartwatch, smartphone or tablet, or the NO generation device itself. In some embodiments, a web browser application presents a dashboard for the user, including current treatment settings, device history, activity log, trending, alarm history, scrubber remaining life and other information related to the patient and treatment. The browser application can be run on a PC, smartphone, tablet, smart phone or other capable device. Information for the web browser app may be communicated directly to the device running the application, or can be delivered through an indirect means, such as cellular network, internet or cloud.

In some embodiments, an NO generation system provides one or more of the following features through the cloud: service information, device usage data, patient physiological data, device performance data, patient activity data, and/or data from other connected devices. In some embodiments, the Cloud is used to provide services, for example: analytics, product upgrades, centralized algorithms, product improvements, and/or AI/Data mining. An NO generation and delivery device can also be connected to social network technology. In some embodiments, the device and/or ancillary devices can be used to add/remove members/roles, share information, share notifications, share alarms, share patient experiences and treatment tips, and/or perform voice/video calls.

In some embodiments, an NO generation device supports voice inputs and voice outputs. For example, a user can say "NO increase" to increase the NO dose or "NO Stop" to cease treatment. The device can also alert the user with a voice prompt about an alarm condition, such as "Replace Scavenger Cartridge" of "20 minutes remaining on battery."

In one embodiment, an NO generation device has a learning mode when a user begins use of the device. During learning mode, the NO generation device can automatically vary treatment parameters such as NO concentration, NO pulse duration, and NO pulse timing to characterize the patient's physiological response based on $SpO_2$, respiratory rate, heart rate, etc. to optimize the dose delivered. In some embodiments, an NO generation device can sense patient exertion and increase NO output accordingly.

In some embodiments, the NO generation device and/or its ancillary components can detect patient over-exertion and provide a warning. In some embodiments, exertion is detected based on accelerometer data. In some embodiments, exertion is determined by heart rate. In some embodiments, exertion is detected by respiratory rate. In some embodiments, exertion is detected by $SpO_2$ level. In some embodiments, exertion is detected by a combination of one or more of accelerometer measurements, heart rate, respiratory rate, respiratory rate, and/or $SpO_2$.

In some embodiments, an NO generation device has a training/evaluation/placebo mode. In this mode, the user interface, treatment modes and alarms are fully functional except for plasma activity being turned off. Patient parameters can be logged in training mode to aid in clinical evaluations of patient behavior, patient physiological parameters and device use.

In some embodiments, an NO generation device supports a weaning mode. In some embodiments of the weaning mode, the level of NO delivered to the patient is automatically decreased over a set amount of time. In some embodiments, the delivered dose is cut in half every 10 minutes until the dose is <1 ppm prior to the device automatically ceasing treatment. Weaning mode can be interrupted by the user or physician at any time by direct or indirect (wireless, remote control) means in the event that the patient does not respond well to the rate of dose decrease. Weaning mode may also be accomplished interactively with the user, whereby the device serves as a timer and reminds the user/physician to decrease the dose after a predetermined set of time. In some embodiments, weaning is fully-automatic, whereby the dose is decreased based on physiologic parameters measured, such as $SpO_2$, respiratory rate, heart rate and the like. In the event that physiologic parameters indicate that a new dose setting is not being tolerated, the system can automatically return to the prior dose or the dose before that. In another form of weaning, the device doses a subset of breaths rather than decreasing the concentration of NO in each breath. In some embodiments, weaning involves both decreasing the NO concentration and decreasing the number of breaths dosed in a given amount of time.

NO Generation Control

NO generation and treatment control can be achieved in a variety of ways, such that the plasma activity relating to the electrodes can be controlled to control the amount of NO generated in the product gas. In some embodiments, the level of plasma activity can be determined by a look-up-table based on variety of variables, including but not limited to ambient pressure, plasma chamber pressure, $O_2$ concentration, $O_2$ flow rate, target NO level, $SpO_2$ level, air flow level, inspiratory flow level, inspiratory pressure, nasal temperature. Pulsatile plasma generation can be synchronized with patient respirations, but it does not necessarily need to be synchronized with patient respiration for a beneficial clinical effect. Owing to the fairly long half-life of NO (in the order of minutes), NO can reside within the lung over multiple breaths. Patients may not need to breathe fresh NO into the lung every breath, and the NO generation device may not need to generate NO for every breath. In some embodiments, an NO generation device can operate periodically at another frequency or a random frequency, independent of patient respiration and still provide therapeutic benefit. For example, NO generation can be ON for 5 seconds and then OFF for 15 seconds with the intention of providing NO for every third or fourth or any number of breathes.

An NO device can operate in the following additional modes:
  Synchronized Mode with pulsed NO delivery delivered in sync with $O_2$ delivery.
  Independent (of $O_2$) Mode with pulsed NO delivery delivered in sync with patient respirations
  Constant Mode with constant NO flow rate and concentration
  Minute volume dosing mode where the dose delivered each breath is varied so that the number of NO molecules per minute achieves a target.
  Minute volume dosing mode where breaths are skipped if the dosing rate has exceeded the target rate for the trailing x number of seconds.
  Minute volume dosing with a combination of varying dose per breath and skipping breaths.
  Variable concentration mode where the concentration in pulses varies. In one embodiment, the concentration varies based on recent dosing over a set time period. In one embodiment, concentration varies with patient activity. It should be noted that concentration can be varied in addition to other pulse parameters, such as pulse timing, duration, flow rate, etc. In one embodiment, pulse parameters and concentration are varied so that an average concentration can be delivered over time.

In some embodiments, the dosing scheme is based on one or more of the following parameters related to patient or environmental conditions: time of day, patient feedback, patient respiration rate ranges, and/or patient height/ideal body weight. In some embodiments, dosing is prescribed as a certain number of moles of NO per healthy body weight per unit time (Prescription (Rx)=µg/kg/hr).

Given that the patient respiratory rate involves fairly consistent frequency (For example, 10 breaths per minute) and consistent tidal volume (for example 500 ml), an approximate a target dose per breath in µg/breath or moles/breath can be derived (For example, 8 µg/breath). The number of moles of NO delivered in a pulse of product gas is a function of the concentration of NO(X), volumetric flow rate ($\acute{v}$) of the product gas, and duration of the pulse ($\Delta t$). It follows that $N \approx x * \acute{v} * \Delta t$ where N=number of moles delivered in a pulse, X=concentration of NO-containing gas, $\acute{v}$=Volumetric flow rate of NO-containing gas, and $\Delta t$=Duration of pulse. Note that ≈I used because pressure and temperature variation effects are assumed to be negligible.

Based on this understanding of dose delivery, multiple dosing schemes can be conceived. In some embodiments, only the concentration (X) of NO containing gas is varied while concentration and volumetric flow rate are held constant. This approach offers benefits in simplicity and noise levels (constant gas flow rate) since only the plasma activity needs to be varied. In some embodiments, only volumetric flow rate ($\acute{v}$) is varied during a pulse while concentration and duration are held fixed. In some embodiments, only pulse duration ($\Delta t$) is varied while volumetric flow rate and concentration are held fixed. Additional permutations exist if more than one variable is changed at a time. For example, in some embodiments, both concentration and volumetric flow rate could be varied in order to deliver a desired dose in a set amount of time. In some embodiments, the concentration is held constant and volumetric flow rate and pulse duration are varied to dose a breath. In some embodiments, the volumetric flow rate is held constant (constant pump speed) and concentration and pulse length are varied. In another embodiment, all three variables are varied in order to dose patient breaths. One advantage to varying all three variables is that optimal dose control varies with patient activity level and respiratory rate. For example, when a patient is sleeping, breaths are long and seldom. An NO generation and delivery system can generate low concentrations of NO over long pulses to dose the long breaths. Contrastingly, when a patient is active and their breaths are shorter, an NO generation and delivery system can increase the concentration and shorten the pulse duration to ensure that a dose is delivered during inspiration. It should be noted that short pulses can require high flow rates and high NO concentrations which can be uncomfortable to the patient and cause more rapid $NO_2$ formation.

The timing of a pulsed dose can be any time within or before the inspiratory event. Pulses occurring before or at the point of inspiration normally require predictive algorithms that calculate when the next breath will occur based on the timing of a series of prior breaths. Pulsed doses occurring after the initiation of inspiration can be based on actual breath detection. The duration of a pulse can vary from tens of milliseconds to the entire duration of inspiration. In one embodiment, the duration of the inspiratory pulse is targeted at one half the duration of inspiration. In one embodiment, the duration of inspiration is based on the duration of the most recent series of breaths. In one embodiment, the duration of the inspiratory pulse is a set unit of time, such as ½ second. In another embodiment, the NO generation and delivery system targets dosing for a fraction of a breath (½ for example) but has an upper time limit. Dosing before or at the time of inspiration may introduce NO containing gas to the patient before gas flow has begun. In this case, the NO containing gas can exit the nose and enter the ambient air. Similarly, pulses with high flow rates, as is often the case with brief pulses, can exceed the flow rate of inspiration, thereby losing NO to the ambient surroundings. In one embodiment, an NO generation system initiates aa long NO pulse after inspiration detection and delivers the pulse until near the end of inspiration at a flow rate well below the inspiratory flow rate, thereby ensuring that NO delivered enters the patient. One benefit to a long pulse approach with an NO generation and delivery system is that NO concentration levels are lower within the pulse for a given dose/breath prescription, thereby reducing $NO_2$ formation.

In some embodiments, the NO delivery pulse begins 50 milliseconds after inspiration detection and lasts 200 milliseconds. In some embodiments, the NO delivery pulse lasts the duration of inspiration.

The dose prescription can be provided to the NO generation and delivery device in a variety of means, including but not limited to: a user (care provider) enters prescription information, prescription information is read from a label, prescription information is sent to the device. The prescription can be generated based on a variety of factors including, but not limited to: patient gender, patient height, patient ideal body weight, patient current body weight, an estimate of tidal volume, actual measured tidal volume, patient tolerance of nasal cannula flow rate and dose/delivery parameters affecting pulse shape.

In some embodiments, the amount of NO generated can be controlled based on the prescription of medical personnel, including a physician. This can allow for less human errors in NO dosage and/or improve quality control. The prescription can provide the dose/delivery methods. There are many ways the prescription could be expressed, including but not limited to being based on time of day, patient feedback, respiration rate ranges, and, patient height/weight. There are many ways the prescription can be provided to the device, including but not limited to a user (for example, a care provider) entering prescription information, prescription information being read from a label, and prescription information being sent to the device.

When breathing rates and/or flow rates are outside the supported range, the device may alarm. In one embodiment, the device employs an automatic/asynchronous (with breath) delivery mode. The asynchronous breathing mode may continue for a set amount of time, or until breaths are detected, or until respirations return to the supported range. In the event that respiratory rates and/or flow rates remain out of range after an initial timeout period, one embodiment of the system escalates the level of the alarm.

In some clinical conditions where a very short pulse of NO-containing gas is to be delivered to the patient and/or the distance from the NO generation device to patient is very long, an NO generation device can stage a pulsed dose of NO-containing gas within the delivery tubing between device and patient prior to delivery. In one embodiment, the NO generator generates a volume of NO-containing gas and advances the volume of gas to a volume of space between device and patient but not all the way to the patient. The volume of space may be a reservoir within the system or the cannula tubing itself, for example. In one embodiment, a 7-foot long cannula with an internal volume of 24 ml is used. Upon detection of an inspiratory event, the NO generator pushes the volume of NO-containing gas the remaining distance into the patient's nose. Actual timing of the NO pulse delivery may be related to other physiologic and non-physiologic events, such as the end of exhalation, amount of time since the last breath, or average respiratory period for the last "n" breaths, for example. Scrubbing of the NO-containing gas may occur within the NO generation device and/or anywhere along the length of the delivery tube, including the tube itself and very proximal to the patient. For slow respiratory rates, an NO generation and delivery system can minimize $NO_2$ levels in the product gas by producing and staging the NO-pulse into the delivery tubing as late as possible. This is done by starting the NO delivery pulse creation at a time such that it will be staged within the tube just prior to inspiration, based on prior respiratory event timing. In one embodiment, the NO generation device operates so completion of NO pulse staging coincides with the end of patient exhalation. Delivery of the staged volume to the patient can be done by increasing pump speed and/or releasing pressure from a pressure source. In one embodiment, a pressurized reservoir of gas is released by opening a proportional valve to push the NO-containing volume of gas to the patient at the correct time. In one embodiment, release of the NO-containing volume of gas is predictively delivered based on the timing of prior breaths. In another embodiment, the release of NO-containing gas is delivered in response to an event, such as the detection of inspiration or the end of exhalation.

In some embodiments, an NO generation device makes an ongoing pulse train of NO-containing gas and non-NO containing gas pulses. The transit time between device and patient is usually known so that the NO-containing pulses arrive at the patient nose in synchrony with inspiratory events. Non-NO containing pulses flush out the tubing between breaths so that NO-containing gases are continuously moving, reducing idle time which could increase the formation of $NO_2$. The pulse train can be adjusted by varying the flow rate of the pulse train, the width of each pulse and the concentration of NO in each pulse te response to changes in patient respiratory rate and activity level. In some embodiments, the pump flow rate is generally constant in the presence of constant inspiratory activity and only plasma parameters are varied to control NO concentration. In some embodiments, the pump flow rate is varied throughout the respiratory cycle.

A variety of treatment inputs can be used to control the function of the device. In some embodiments, a level of NO generation is set by the user within limits set by a physician. In some embodiments, the user has no control of dose level. In some embodiments, a system can automatically increase NO generation based on indications of increased patient activity from sensor measurements. Examples can include an accelerometer within the NO generator that can sense increased activity of the user, measured $SPO_2$ level within the patient, receiving the breath trigger signal from an $O_2$ deliver device, and a respiration sensor that can detect increased respiratory rate indicative of increased activity.

Figure 47B:
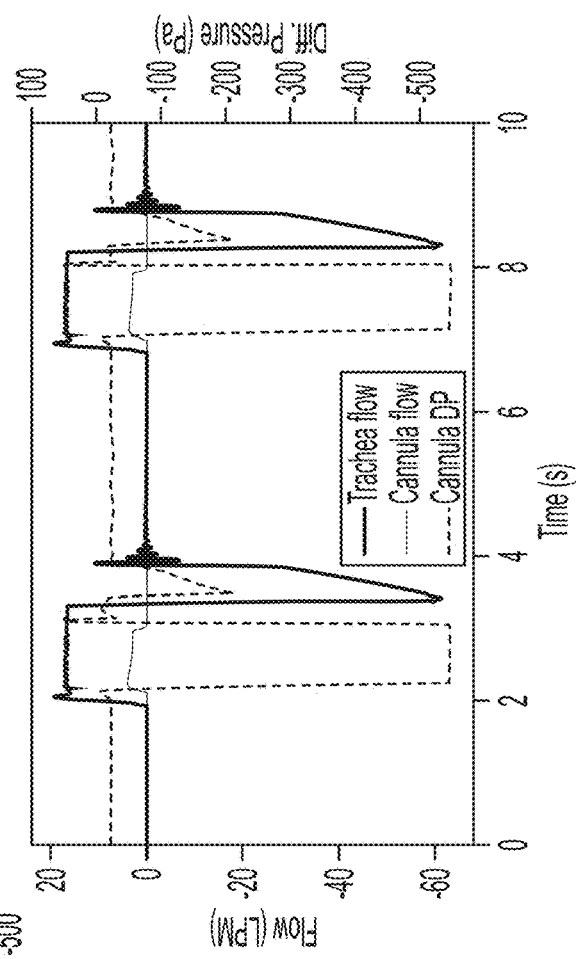
FIG. 47A and FIG. 47B depict graphs related to the detection of an inspiratory event as an increase in cannula delta pressure measured within the NO delivery lumen.
Figure 47A:
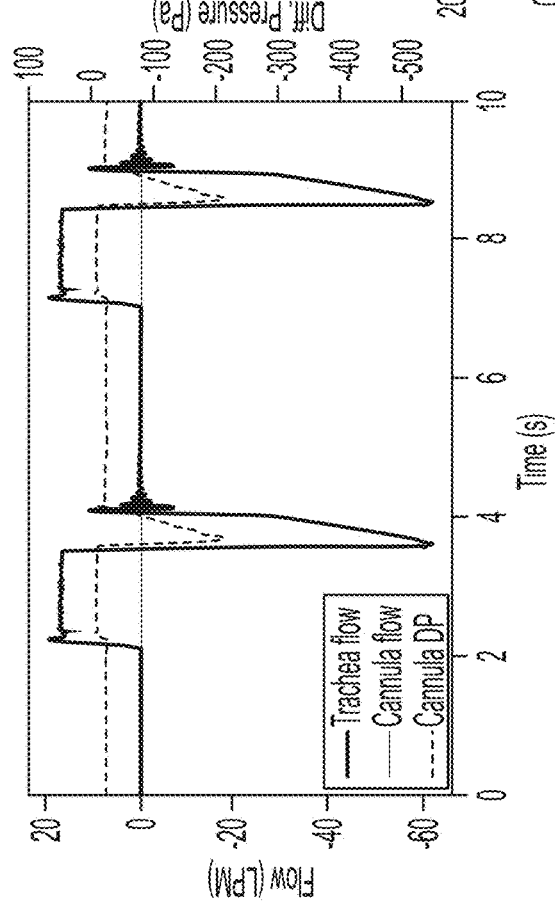

Various methods can be used alone or in concert to detect respiration, such as a strain sensor on the skin of the patient, a microphone, a pressure sensor in the NO delivery line, a pressure sensor in a dedicated lumen from device to nose, a temperature sensor under the nose, a pressure sensor under the nose, a flow sensor under the patient nose, an optical sensor within the air flow of the nose, an accelerometer on the patient chest, a displacement sensor on the patient, a strain sensor on the patient chest, or other means. In one embodiment, a microphone is placed on the patient neck. In some embodiments, a strain sensor is placed on the skin of the patient's torso. By detecting patient respiratory activity, such as breathing rate, breathing depth, breath pulse shape, the NO generation system can optimize NO delivery. Patient-mounted sensors may be wired to the cannula or directly to the NO generator. In other embodiments, the sensors are wireless and communicate via Wi-Fi, Bluetooth, infrared, RF or some other means to the controller. In some embodiments, pressure is measured within the lumen that delivers NO to the patient. In some embodiments, an algorithm ignores the pressure signal during an NO delivery pulse, then monitors for an inspiratory event as the patient exhales. FIG. 47A and FIG. 47B depict the detection of an inspiratory event as an increase in cannula delta pressure measured within the NO delivery lumen. The increase in pressure occurs as inspiration occurs (FIG. 47A). FIG. 47B shows the cannula delta pressure signal during NO delivery with a large deviation one direction and then the opposite direction. In some embodiments, inspiration detection is turned on again after NO delivery. In some embodiments, inspiration detection is turned on again after NO delivery plus a variable delay to prevent false positives. In some embodiments, the variable delay is a fraction of the respiratory period measured by a series or prior breaths. In some embodiments, the delay duration is 25% of the respiratory period. In some embodiments, inspiration detection does not start again until cannula delta pressure returns to a level that equals that of prior expiratory events for a set period of time, the pressure level being based on that of recent breaths. In some embodiments, an NO generation device operates in continuous delivery mode such that the cannula delta pressure is largely related to patient inspiratory activity. In some embodiments, the NO delivery is continuous so the system does not ignore the artifacts caused by dose delivery. Variance in pressure within that line is indicative of respiration. In one case, pumping within the line can be at a constant rate, however changes in pressure due to respiration could be detected with variable pump rates as well. In some embodiments, pump activity is timed to occur at a different time than inspiration detection to prevent pump activity from interfering with detection. In some embodiments, an accumulator can be used to dampen pressure waves from the pump and improve signal to noise ratio of the NO line pressure measurement.

The breath detection signal can vary with patient anatomy, patient disease state, patient activity (sleep vs. active), or other patient-related factors. Thus, an NO generation system can require tuning of the breath detection algorithm for each individual patient. In some embodiments, a delta-pressure threshold is adjusted for each patient as part of device installation. The delta-pressure threshold can be dynamically adjusted by the device, based on patient activity, time of day (awake vs. sleeping), mounting in the charger (indicating more sedentary activity) or other factors that could affect the inspiratory event.

A patient's respiratory rate may vary with exertion. Faster respiratory rates could lead to excessive NO delivery if the NO generation system delivers the same amount of NO with every breath. It should also be noted that respiratory depth (i.e. tidal volume) can vary as well and is generally independent of respiratory rate. For NO treatment to be effective, the concentration of NO in the patient lungs (bronchioles and/or aveoli and/or other parts of the lung) should be at therapeutic levels periodically, if not continuously, owing to the fact that NO has physiologic effects that persist within the tissue for some time and diminish according to the NO physiologic half-life. In one embodiment, the NO generation system doses a subset of breaths, using a combination of one or more of respiratory rate, tidal volume, physiological NO half-life, inspired $O_2$ concentration, target dose, recent historical dose information, and/or NO oxidation rate to determine which inspirations to dose. In another embodiment, NO is delivered with each breath but pulse parameters are varied based on one or more of respiratory rate, estimated entrainment fraction, physiologic NO half-life, NO oxidation rate, and/or inspired $O_2$ levels to achieve target NO concentration within the lung. In one embodiment, the amount of NO delivered per breath is adjusted based on respiratory rate such that the overall prescribed deliver rate is achieved by delivering discrete parcels in each breach or a subset of breaths without computing or compensating for tidal volume changes. In one embodiment, the NO generation system delivers a consistent pulse each a pulse is delivered and has a maximum number of breaths that it will dose per unit time. In another embodiment involving consistent doses, based on a moving average, if the number of dosed breaths per unit time exceeds a threshold, the device stops NO delivery until the moving average falls below the threshold. In another embodiment, the volume of the pulse is consistent but the concentration of NO is varied to achieve the desired dose. In another embodiment, the pulse duration is consistent but one or more of the pulse flow rate and concentration are varied to achieve the desired dose. In another embodiment, the pulse flow rate is consistent, but one or more of the pulse duration, and concentration are varied to achieve the requested dose. In another embodiment, the target delivery amount per breath is fixed based on assumed breathing parameters, and periodic "make-up" pulses are used whose NO content is varied to compensate for actual measured breathing patterns, Features can also be added to the delivery device to detect respiration. In some embodiments, a wire runs up one tube and down the other tube of a nasal cannula. Between the nostrils, there is a small thermistor. One way of making such a thermistor is to use a piece of Mylar with sputtered aluminum on it. Respirations are detected by looking at the changes in resistance of the thermistor, indicating the warmth of exhalation of cooling of inhalation. Two wires could run in one tube too. In some embodiments, sensing could also be done by stretching the wire to be thinner in the area of temperature sensing. In some embodiments, the barb of the nasal cannula is metallic and conductive so that it is part of the thermistor circuit. This works best when there is wire in two lumens and two barb connections to the controller. In some embodiments, a thermocouple under the nose can be provided. In some embodiments, an NO delivery device can include a cannula NO lumen that bifurcates as it reaches the controller. One lumen connects to the scavenger and the other lumen connects to a blind hole with a pressure sensor for detecting respirations. In some embodiments, an NO delivery device is provided where an NO line pressure is sensed within the controller near the cannula connection point so that patient respirations can be sensed via pressure.

Figure 48:
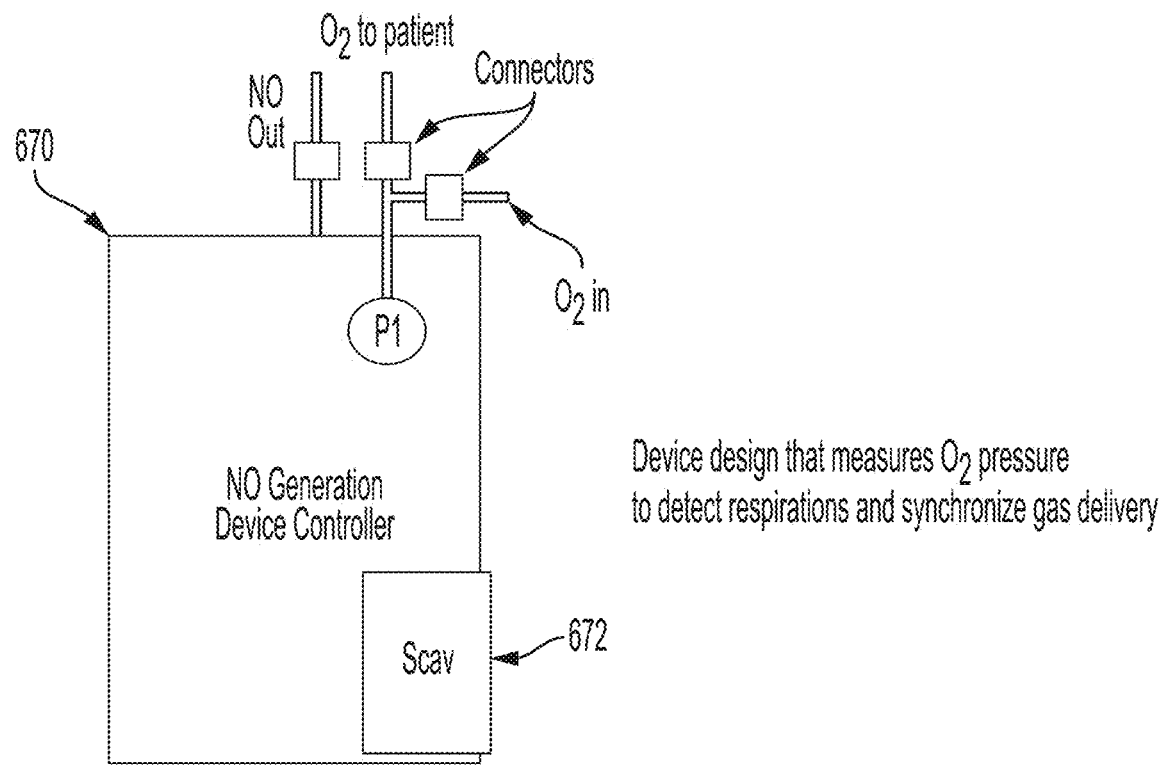
FIG. 48 is an embodiment of an ambulatory NO generation device.

There are various techniques that can be used to detect respiration. In some embodiments, an NO delivery device 670, as shown in FIG. 48, can include a cannula with an NO lumen that bifurcates as it reaches the controller. One lumen connects to the scavenger 672 and the other lumen connects to a blind hole with a pressure sensor for detecting respirations. In some embodiments, an NO delivery device can sense an NO line pressure within the controller near the cannula connection point so that patient respirations can be sensed via pressure. Respiration detection can also be done in conjunction with $O_2$ concentrator use. NO delivery device with T-fitting that receives $O_2$ from an $O_2$ source, sends $O_2$ to patient (via cannula) and has a pressure sensor within the controller at the bottom of a blind hole, as shown in FIG. 48.

Figure 49:
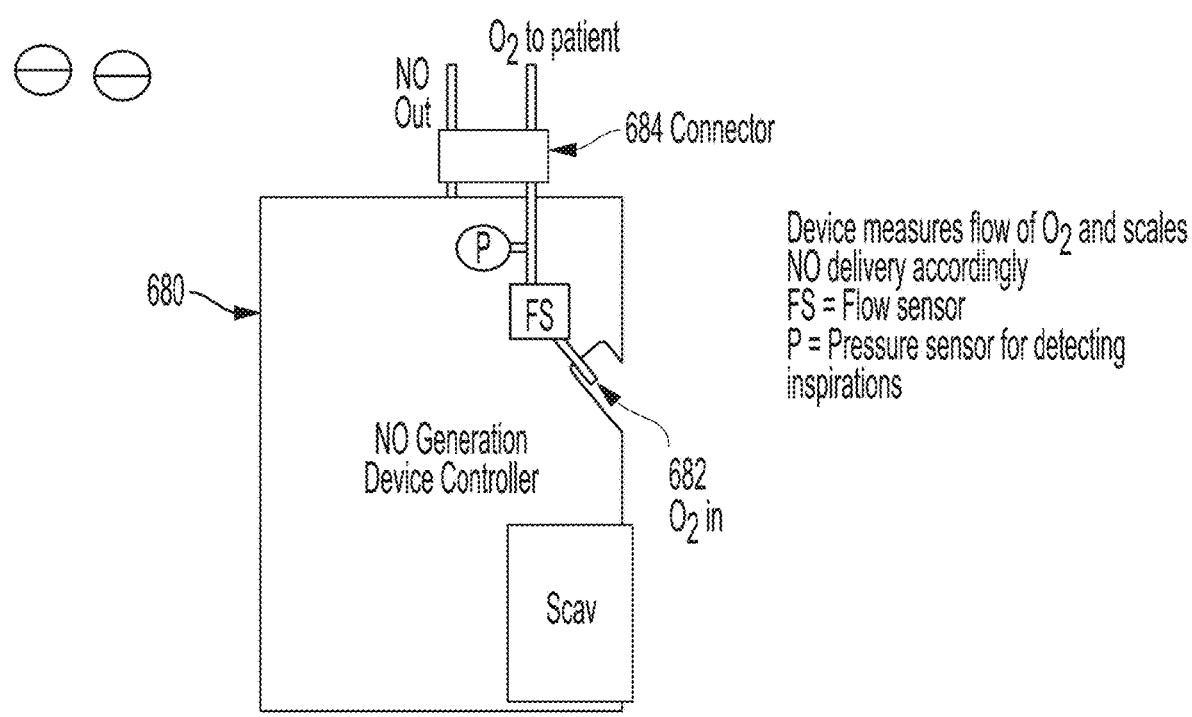
FIG. 49 is an embodiment of an ambulatory NO generation device.
Figure 50:
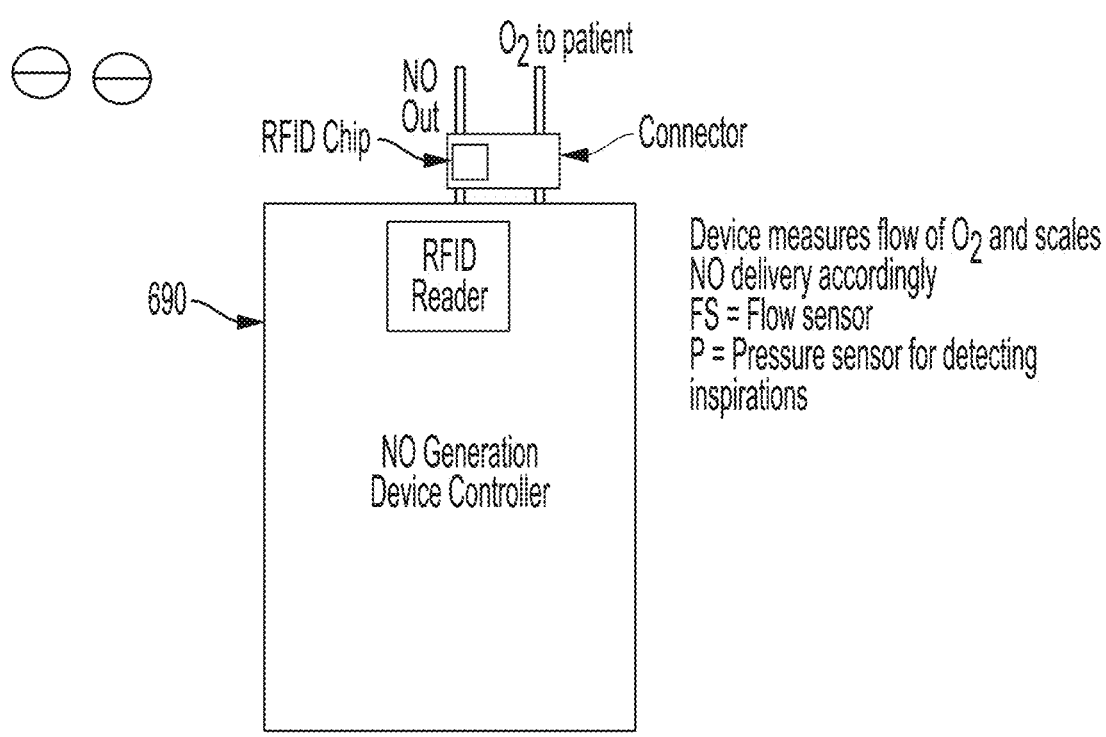
FIG. 50 is an embodiment of an ambulatory NO generation device.

In some embodiments, the NO delivery device 680 can include an $O_2$ input connection 682 and separate $O_2$ output connection 684, as shown in FIG. 49. Between the two connections, the system senses pressure and/or flow to detect oxygen concentrator activity. In this embodiment, NO and $O_2$ have separate output connections. There may be a single exit point with NO and $O_2$ combined. In some embodiments, an NO delivery device 690 is provided that works in conjunction with an $O_2$ concentrator that includes a mechanism, such as an RFID reader, to communicate with the NO delivery device, as shown in FIG. 50.

The level of NO can also be adjusted based on activity of an $O_2$ source. The $O_2$ source can vary, such as a tank-based system or an $O_2$ concentrator. For example, the NO generation device could monitor flow of $O_2$ within an $O_2$ delivery lumen and increase NO levels in linear proportion (or some other algorithm) to $O_2$ flow. In some embodiments, $O_2$ from an $O_2$ concentrator can flow through the disposable component of the NO generation device where it is measured by a flow sensor. In some embodiments, $O_2$ flows through a reusable portion of the NO generator and the $O_2$ flow sensor consists of either a delta-pressure sensor with a flow restriction, a hot wire anemometer, or other sensor with the intended purpose of measuring flow. In an embodiment, the system can have a direct electrical or wireless connection to the $O_2$ generator and receive inputs on $O_2$ generation levels. In some embodiments, the NO generation system can measure the strain in the $O_2$ line of the cannula to understand the level of $O_2$ delivery and the mode (pulsatile vs. constant). In some embodiments, the radial displacement of the $O_2$ line can be sensed with an ultrasonic sensor to detect $O_2$ flow levels and patterns. For example, the oxygen tube of a nasal cannula can be pushed into a slot on the side of the housing. In some embodiments, a line from an $O_2$ concentrator is inserted into the slot on the side of the housing. A pressure, strain, ultrasound, force, displacement, microphone, or optical sensor can be used to detect perturbations in the $O_2$ tube wall. The magnitude of perturbations can be enhanced by placing a small flow restriction (a bump for example) within the oxygen flow path to create some back pressure behind the restriction. The wall strain/displacement/pressure sensor will detect the flow activity of the $O_2$ source and enable the NO generator to synchronize NO delivery with the oxygen supply. One benefit of this approach is the $O_2$ line runs continuously from the $O_2$ source to the either the cannula or nasal prongs without a connector. Another benefit is that the housing of the NO generation device does not require any openings which could permit fluid or other contamination to enter the sealed housing. The slot could be horizontal or vertical and can be the mechanical holder for the oxygen tube. The magnetic driven power connection can also be expanded to make the magnet bigger and more powerful to add to the retention of the base to the generator.

FIG. 51A and FIG. 51B illustrate an embodiment of a controller enclosure 700, shown in cross-sectional view in FIG. 51A. The enclosure 700 can include an $O_2$ delivery tube 702, such as a nasal cannula (represented in a cross-sectional view). The enclosure 700 can also include various sensors 704, including but not limited to a pressure sensor, a sound sensor, a displacement sensor, a strain sensor, an optical sensor, and/or an ultrasound sensor that can detect variance in pressure/flow within the $O_2$ line. In one embodiment, an array of parallel lines, coaxial with the $O_2$ line are spaced around the circumference of the $O_2$ line and an optical sensor senses the distance between the lines to detect $O_2$ pulses. Communication with the $O_2$ source device can be via direct electrical connection, cellular, radio frequency, optical, acoustic, ultrasonic, or some other wireless means.

Figures 52A, 52B, 52C:
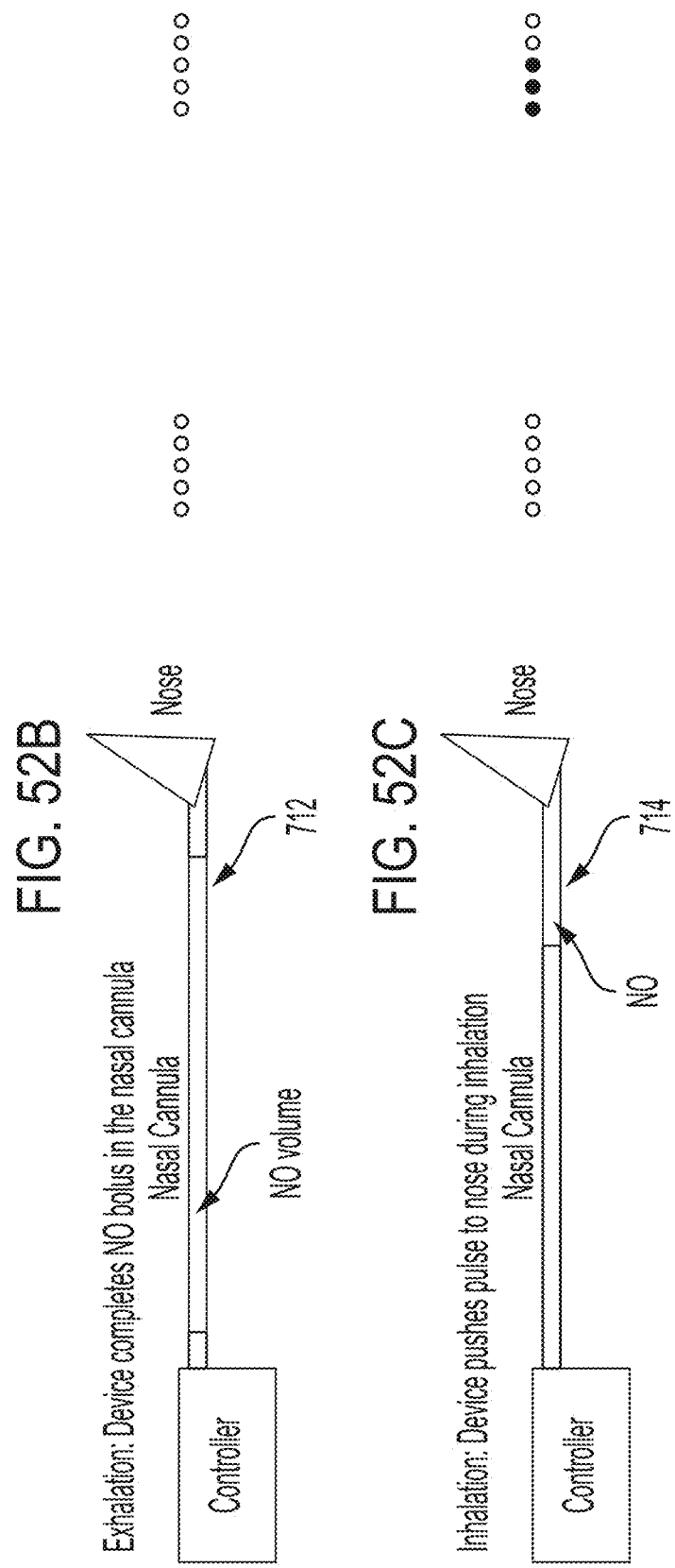
FIG. 52A, FIG. 52B, and FIG. 52C are embodiments of a portable NO generator that stages a volume of NO within a nasal cannula prior to inspiration.

It can be a challenge for an NO generation and delivery system to detect an inspiration, generate NO and delivery NO in real time. This is due to the time it takes for inspiration to be detected, time required to initiate NO flow and transit time from the generator to the patient. FIG. 52A, FIG. 52B, and FIG. 52C depict embodiments of a portable NO generator that stages a volume of NO within a nasal cannula 710 (FIG. 52A) prior to inspiration. In this embodiment, the device prepares NO during patient exhalation 712 (FIG. 52B). When inspiration is detected, the device pushes the pulse to the patient, clearing the nasal cannula 714 (FIG. 52C). Then the device repeats the process by placing another volume of NO within the nasal cannula.

Environmental influences can also affect NO generation. For example, an NO generation device can operate at high altitude or low altitude due to its ability to vary NO generation based on a measurement of ambient pressure and or plasma chamber pressure.

Figure 53B:
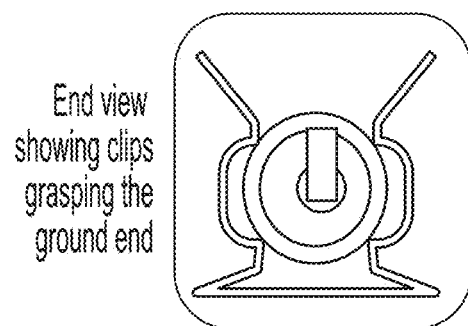
FIG. 53A and FIG. 53B illustrate views of an embodiment of an NO generation system with an embodiment of an electrode assembly.
Figure 53A:
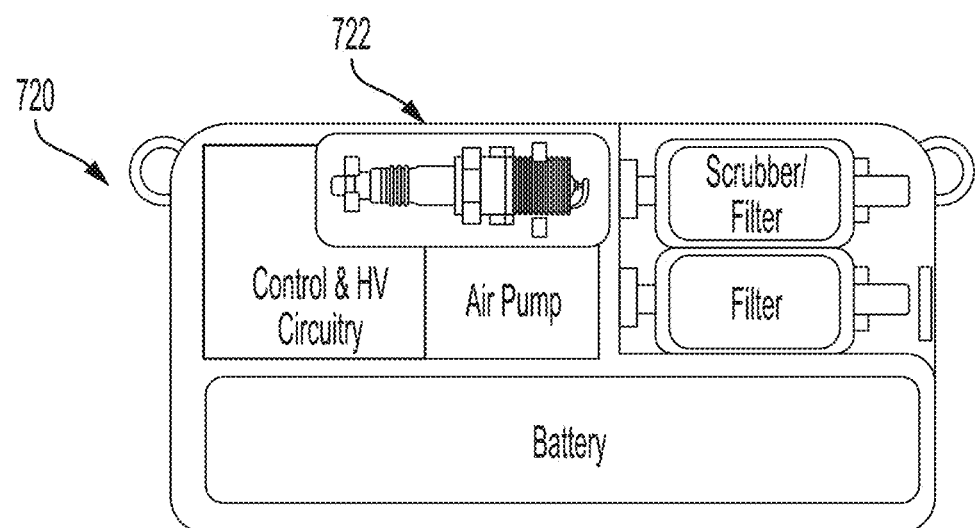

In some embodiments, a NO generation device includes an inlet filter scavenger, an air pump, and an electrode assembly. In some embodiments, an electrode assembly can be sized to last the lifetime of the device, which can vary but in an embodiment can be up to 5 years. This can reduce the complexity of the device and can spare the user from having to replace electrodes. In some embodiments, electrodes can be part of the cartridge or a separate assembly, requiring periodic replacement. In some embodiments, automotive-style electrode assemblies can be used. FIG. 53A and FIG. 53B illustrate an embodiment of a wearable NO generator 720 with automotive-style electrode assembly 722 that can also include an exhaust filter scavenger, pressure sensor, a battery, an enclosure, a docking station, and an oxygen sensor that can be used for measuring $O_2$ levels in the plasma generation air.

It is possible for the device to include features to prevent overheating. As the ambulatory device can be placed in various locations, including on an $O_2$ generator trolley or a battery charger (for example, positioned at a 45 degree angle for stability and ease of reading a display), or be worn by a patient, for example on a belt, in a bag or worn under a coat, it is possible for the device to overheat. In some embodiments, the air that is used to generate NO could be run over heat exchangers to cool the electronics. In one embodiment, the NO generator is located at the air inlet for an $O_2$ concentrator. In some embodiment, the air used to generate NO could be run over heat exchangers to cool the electronics. In some embodiments, the enclosure of the NO generation device is made from a thermally-conductive material, such as aluminum. Heat-generating components can be dispersed throughout the enclosure and mounted to the enclosure such that the heat is conducted to the surface of the enclosure evenly, thereby enabling heat to leave the system without elevating the surface temperature of the controller enclosure beyond safe levels. In some embodiments, the charging current of the device is governed so that the additional heat caused by battery charging does not overheat the device. In some embodiments, the battery charging current is controlled by the internal enclosure temperature so that faster charging currents are used when thermally permissible.

Figure 54:
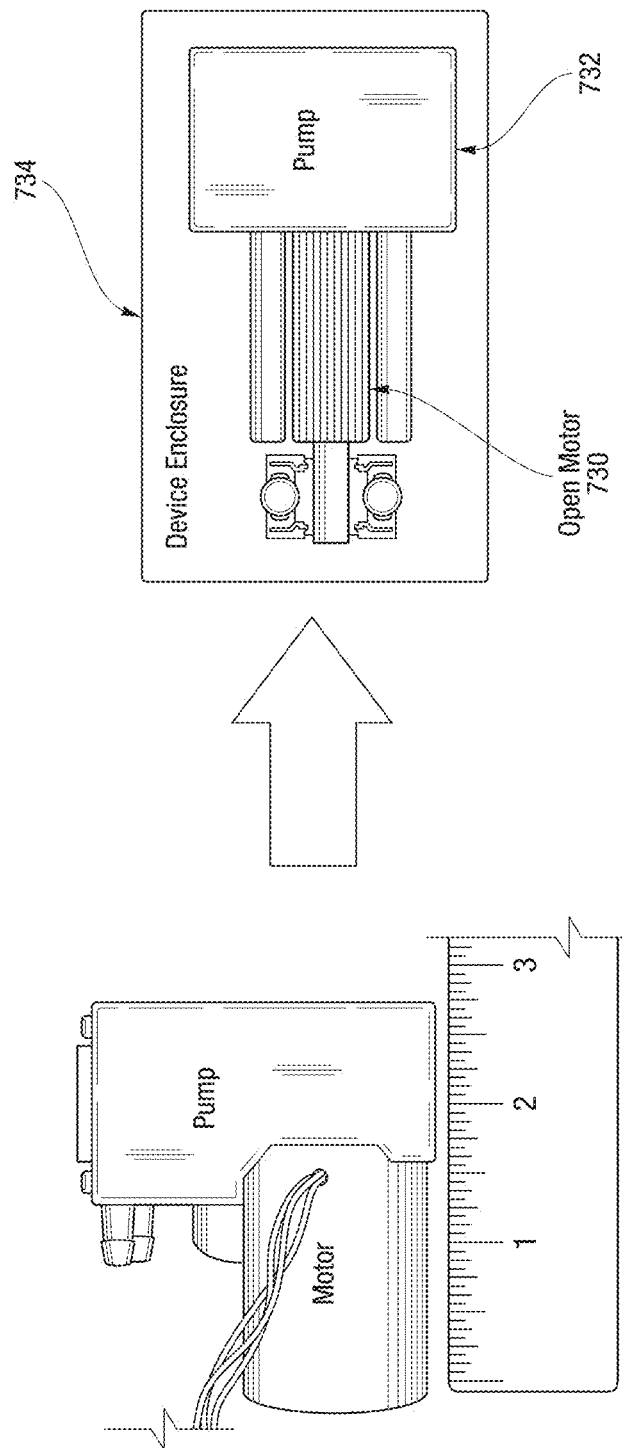
FIG. 54 is an embodiment of an NO generation device enclosure with an open motor mounted directly thereto.

Many internal components of an NO generation device can be integrated into the device enclosure. For example, the manifold that routes reactant gas, product gas, and $O_2$ through the device can be integrated into the enclosure thereby reducing device volume, device mass, and assembly time. In one embodiment, an open motor 730 is mounted directly to the NO generation device enclosure 734 to reduce the mass of having a separate motor enclosure (FIG. 54). In one embodiment, the enclosure 734 of the NO generation and delivery device also serves as the enclosure for the pump component 732, reducing mass and volume further.

Control Circuitry

Figure 55:
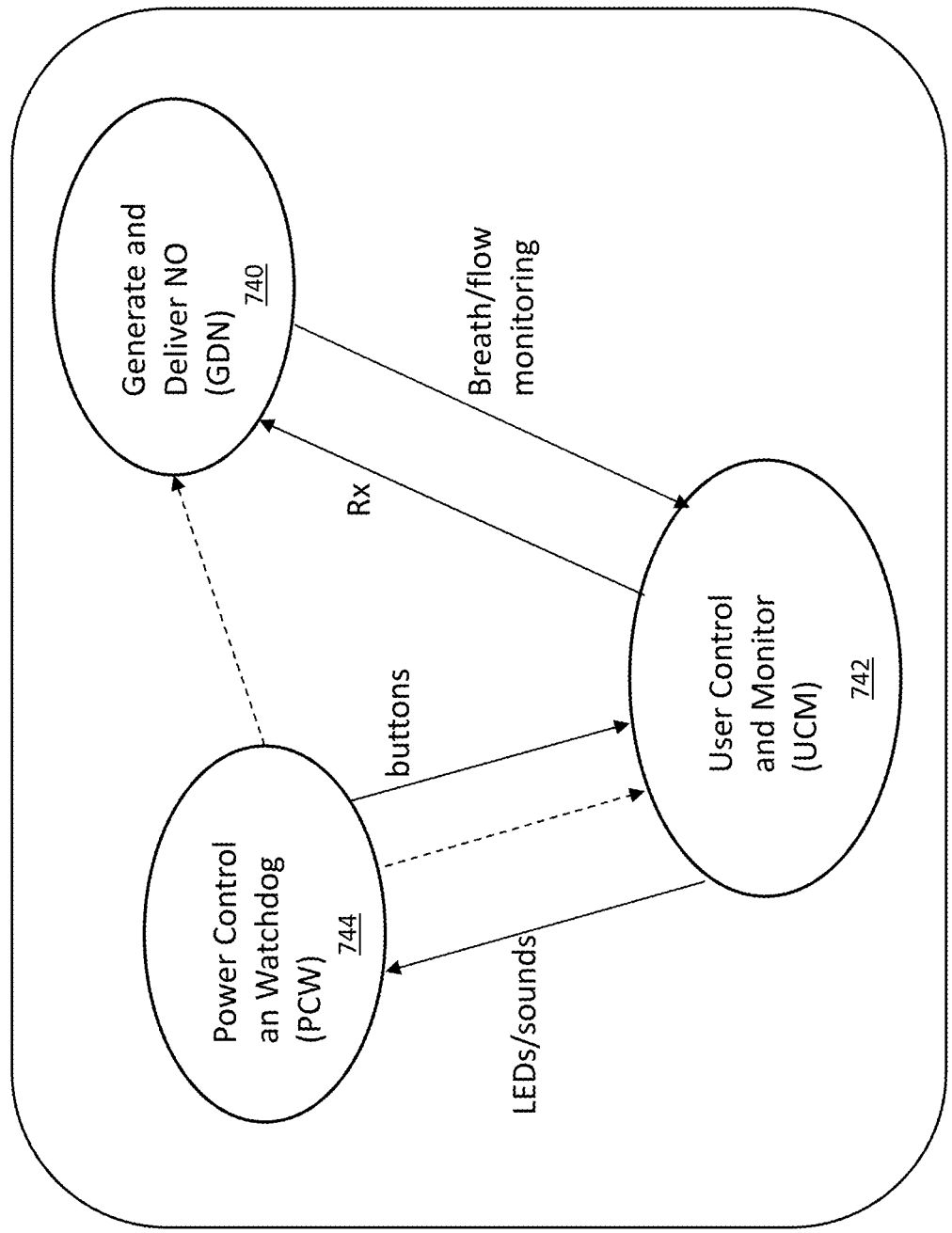
FIG. 55 is an embodiment of electronics of a portable NO generation device.

In some embodiments, the electronics of an NO generation and delivery device have three primary groupings, as shown in FIG. 55: 1) Generate and Delivery NO (GDN) 740, 2) User Control and Monitoring (UCM) 742, and 3) Power Control and Watchdog (PCW) 744. The Generate and Deliver NO circuits receive treatment setting inputs from the UCM and sensor inputs that are pertinent to the treatment ($O_2$ flow rate for example). The GDN circuit controls the volumetric flow rate of reactant gases via pump speed and/or proportional valve and/or binary valve controls. The GDN also controls plasma activity, including one or more of plasma duration, energy, duty cycle, and frequency. For a given prescribed dose, the GDN controls one or more of volumetric flow rate, pulse duration, and NO concentration based on the prescribed dose and patient respiratory parameters (inspiratory timing, inspiration duration, respiration rate, detectability of respiration, etc.).

Figure 56:
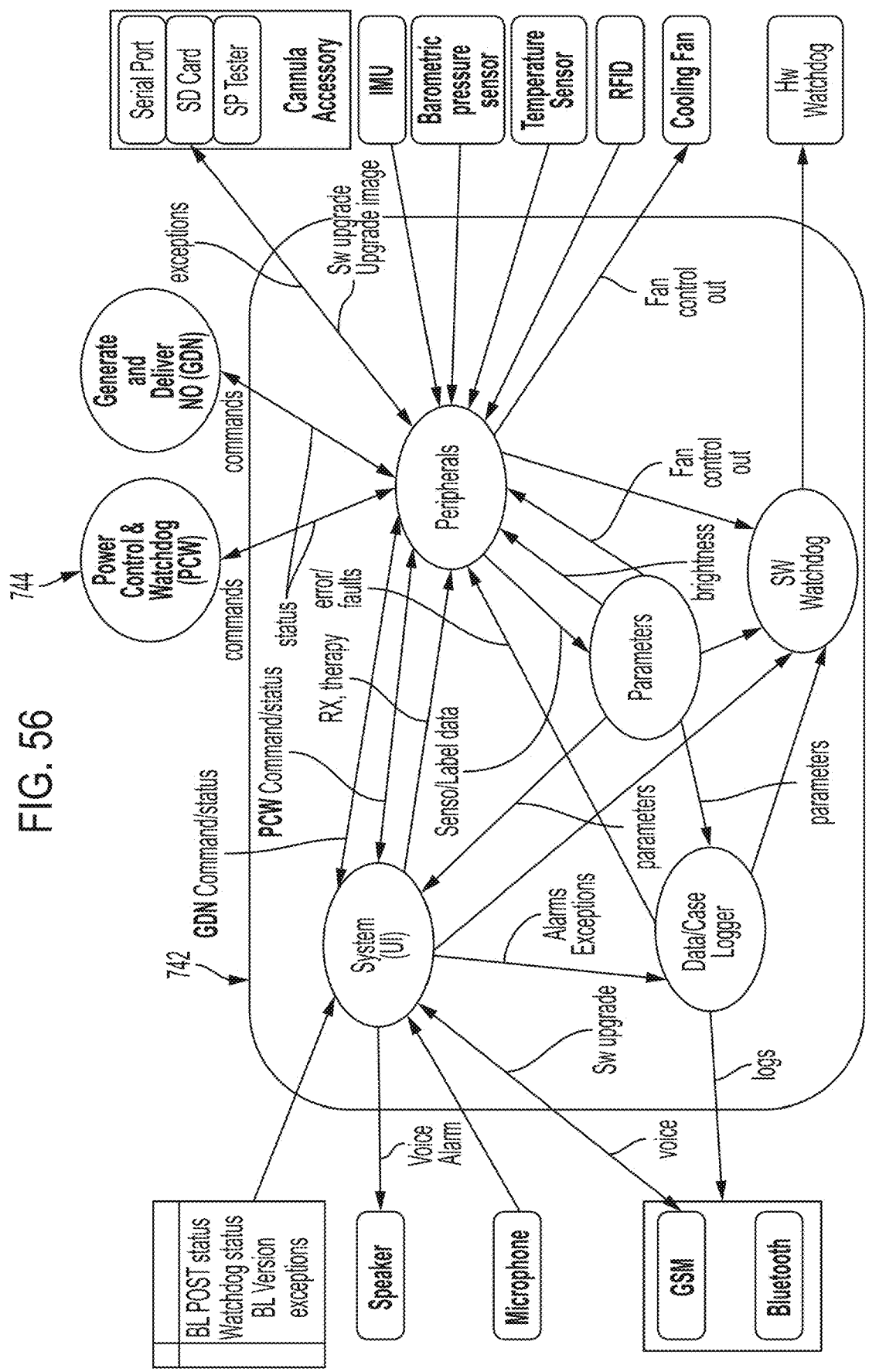
FIG. 56 is an embodiment of the User Control and Monitoring (UCM) circuitry of FIG. 55.

In some embodiments, the User Control and Monitoring (UCM) circuitry 742 as shown in FIG. 55, receives inputs from the user interface and controls the various indicators on the display, as shown in FIG. 56. The UCM 742 also controls the alarm function of the device and can generate alarm conditions and voice prompts as applicable. Interaction with external devices such as adjunct devices, the cloud, GSM network, etc. are managed by the UCM 742. The Power Control and Watchdog (PCW) circuitry 744 controls batter charging and battery drainage to supply a constant voltage to other circuits. The PCW 744 also contains a watchdog circuit that monitors the UCM, PCW and GDN software to ensure proper function and has the ability to initiate a reboot of any subsystem while the system is running. In one embodiment, the PCW includes a large capacitor that can drive a piezo-electric buzzer in the event of total system failure. In one embodiment, the UCM, GDN and PCW circuits are integrated into one printed circuit board, but other groupings can be contemplated based on fitting them around other less-flexible components within the enclosure. Connections to the boards are typically soldered, rather than using connectors, to minimize size and mass.

Figure 57A:
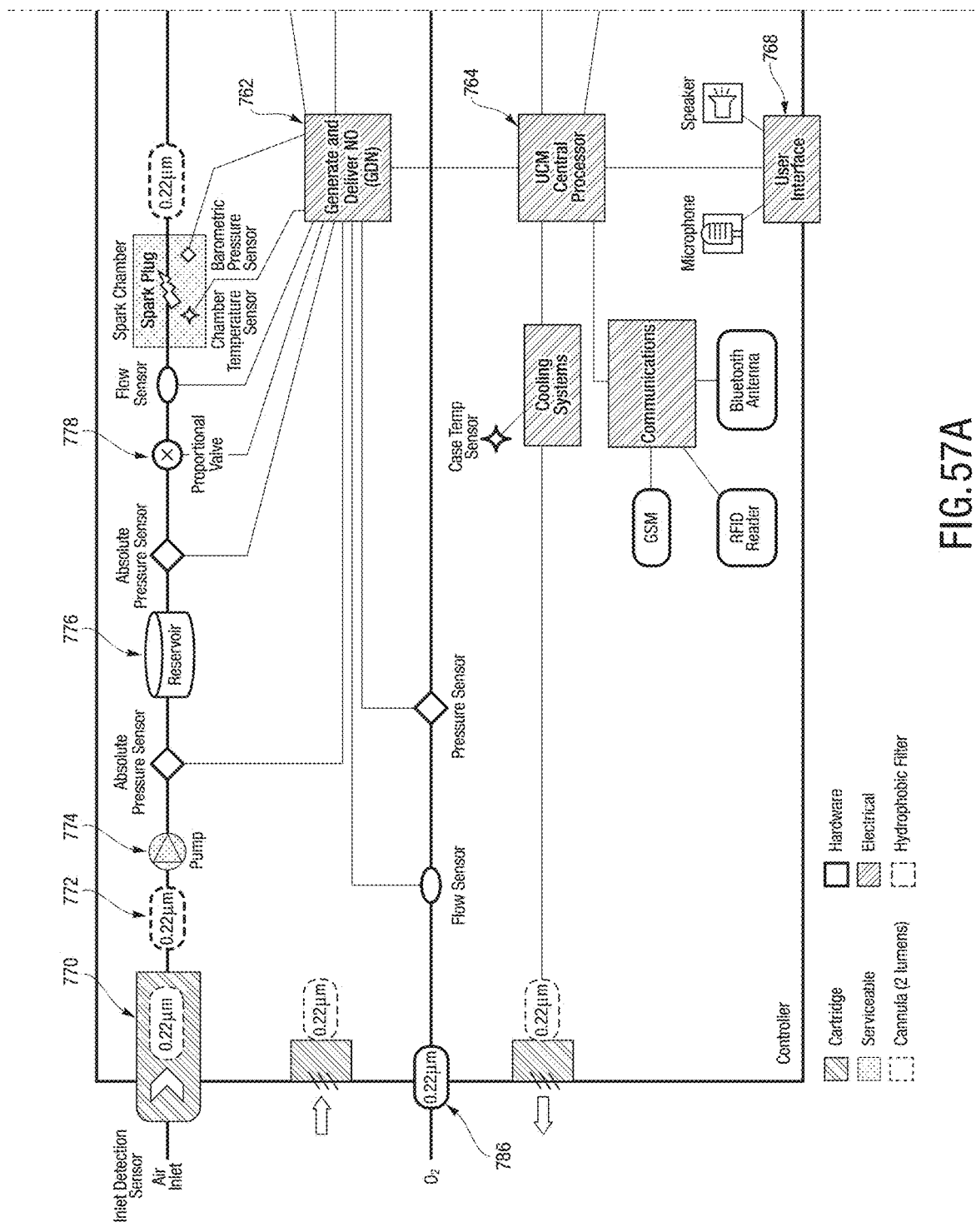
FIG. 57A and FIG. 57B illustrate an electrical and pneumatic schematic of an embodiment of an NO generation and delivery system.
Figure 57B:
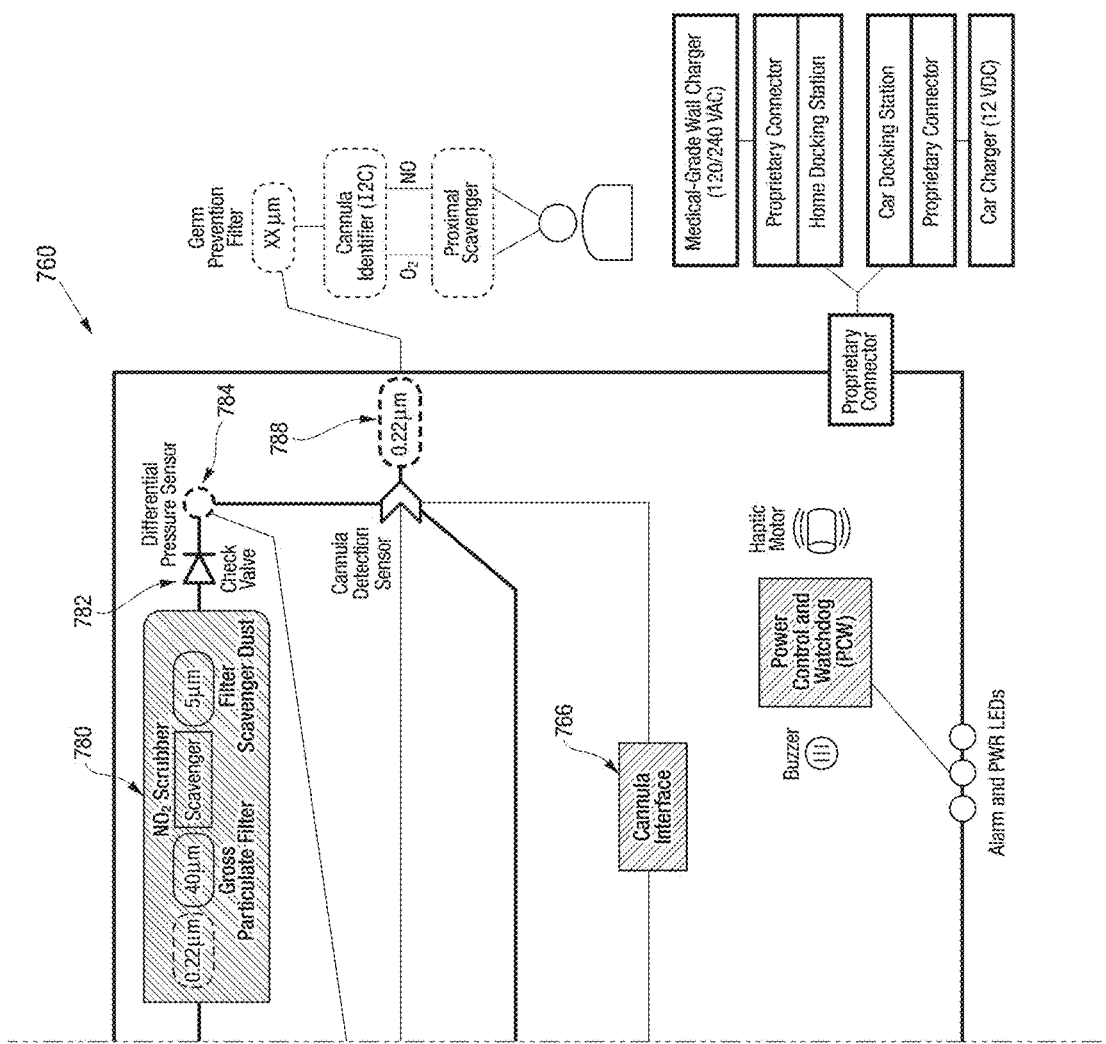

FIG. 57A and FIG. 57B depict the electrical and pneumatic schematic 760 of an NO generation and delivery system. Electrical connections are depicted as dashed lines. Pneumatic connections are depicted as solid lines. Components within a removable filter/scavenger cartridge are located within green rectangles. The plasma chamber is shown as an orange rectangle. A Generate and Deliver NO (GDN) circuit 762 is used to administer the treatment based on one or more sensed parameters including: $O_2$ flow, $O_2$ pressure, ambient absolute pressure, plasma chamber pressure, cannula type, breath detection from a differential pressure sensor (upper right), and/or a reactant gas flow sensor. A User Control and Monitoring (UCM) circuit 764 receives user inputs from the user interface 768, GDN 762, and cannula interface 766. The UCM communicates with a communications module that manages GSM, RFID, Bluetooth, and/or WiFI connections. Incoming air passes through a removable filter 770 prior to passing through a filter 772 and a pump 774. A reservoir 776 pressure is controlled to a target pressure based on a reservoir pressure measurement. Air exits the reservoir through a proportional valve 778. The proportional valve opening level is controlled to a target level based on feedback from a plasma chamber flow rate sensor. Product gases pass through a second filter before travelling through a disposable filter/scavenger/filter 780 and check valve 782. A differential pressure sensor 784 in the pneumatic path is used for detecting patient inspiration. Oxygen flows through a separate pneumatic pathway protected by filters 786, 788 on each end. Within the oxygen pathway, flow and pressure are detected and used as an input into NO pulse timing in some embodiments. $O_2$ and NO exit the system on the right of the diagram and enter a cannula or other type of tube for delivery of gases to a patient.

Figure 58A:
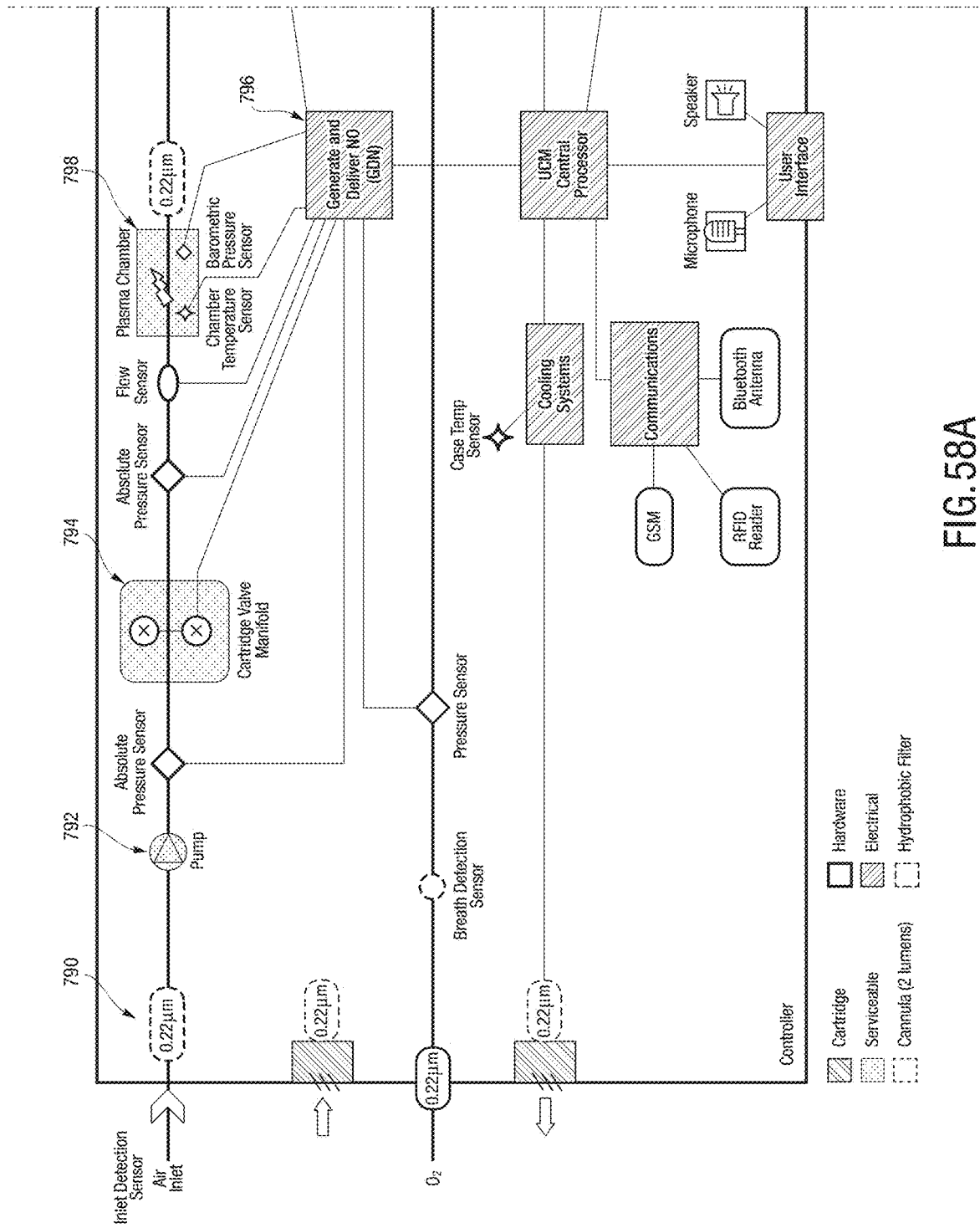
FIG. 58A and FIG. 58B illustrate an embodiment of an NO and delivery device with a cartridge valve manifold.
Figure 58B:
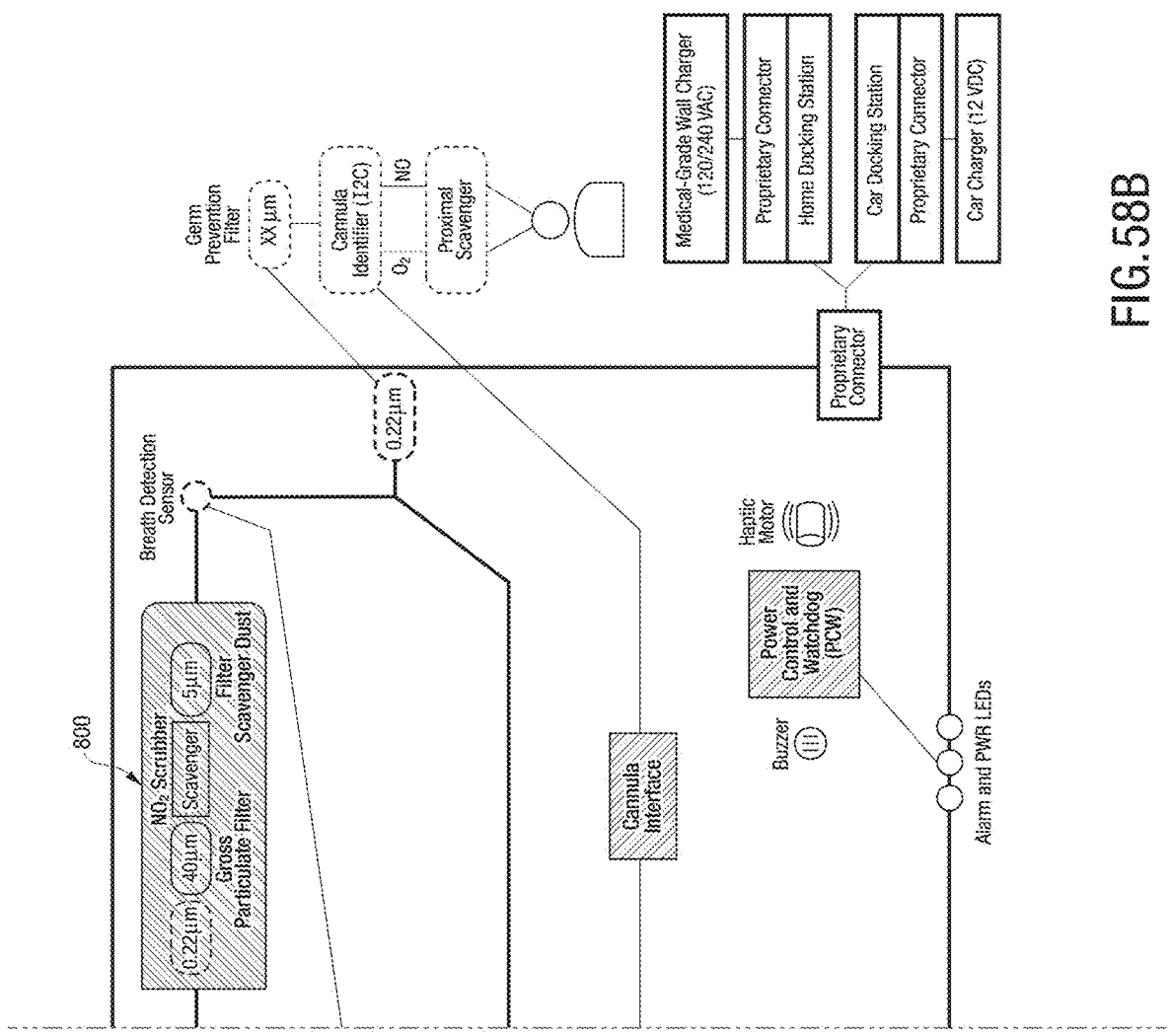

FIG. 58A and FIG. 58B depict an embodiment of an NO and delivery device with a cartridge valve manifold. Ambient air is drawn in through a filter 790 and pump 792 shown in the upper left of the figure. The pump 792 builds pressure within the pneumatic pathway and can be modulated based on a pressure sensor measurement downstream of the pump. An array of one or more binary valves 794 release flow from the pump in varying amounts depending on how many valves are open. Valve position is controlled by the Generate and Delivery NO (GDN) circuit 796 based one or more of a variety of potential treatment algorithms. Beyond the valves, air travels through a plasma chamber 798, filter and filter/scavenger cartridge 800 before exiting the device enclosure through a filter and into a cannula.

It can be possible that a user connects to a stationary $O_2$ concentrator when at home and use a line, such as a 50 foot (15 m) line, to receive $O_2$. The transit time of NO in a 50' line could be long enough that unsafe levels of $NO_2$ form. In some embodiments, a line, such as a 50' line, can be provided with proprietary connectors that have a $NO_2$ scavenger at the patient end to remove $NO_2$ closer to the patient. Proprietary connection could involve custom thread, RFID, bar code, or other features.

Treatment settings, alarm limits, and treatment limits can all be variable and can be set, for example, by a physician. The settings can be made in a variety of ways, including but not limited to through the use of a remote device (for example, cell phone), an imbedded user interface, or by turning a screw/knob or other mechanism connected to a potentiometer.

NO Recirculation

Figure 59B:
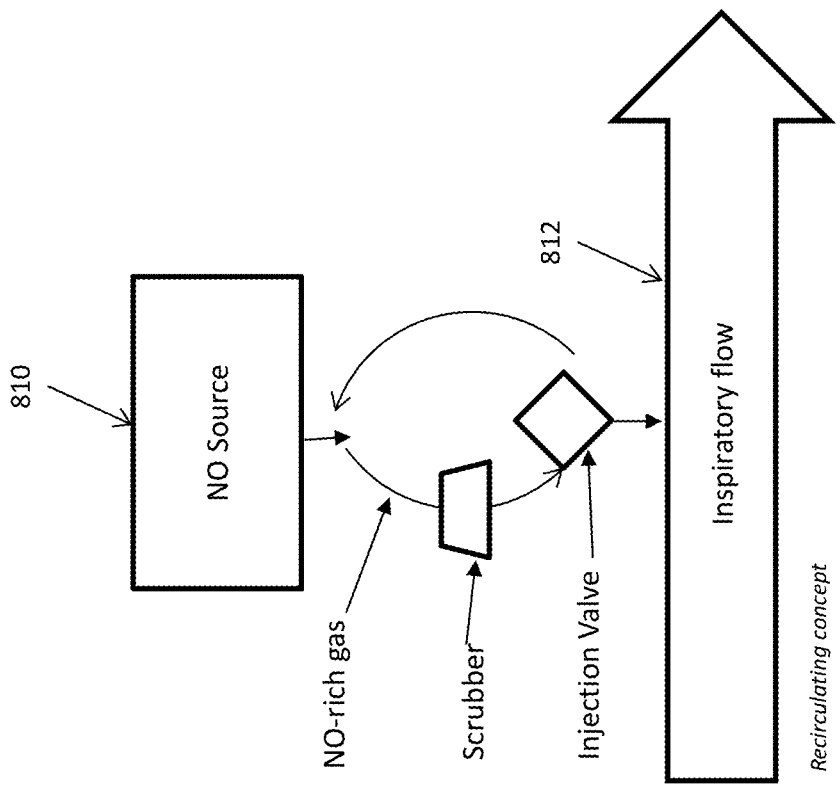
FIG. 59A and FIG. 59B illustrate embodiments of recirculation of NO.
Figure 59A:
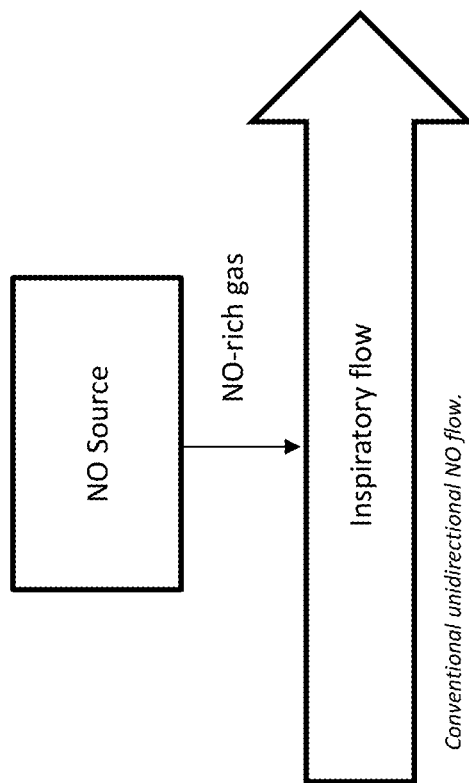

In some embodiments of inhaled nitric oxide therapy systems, the pneumatic pathway conducts gas in a single direction from the NO source (i.e. tank or generation unit) to the point where the NO-rich gas is injected into the flow in the inspiratory circuit (FIG. 59A).

In some embodiments, recirculation of gas between the NO source 810 and the point of injection 812 can be achieved (FIG. 59B). This can be used with all types of NO generation systems described herein, including ambulatory systems and acute applications, for example, with a remote NO-injector.

At standard temperature and pressure, nitric oxide reacts with the oxygen to form nitrogen dioxide ($NO_2$). $NO_2$ is a toxic pollutant to which human exposure should be limited. The rate of oxidation of NO is the rate of formation of $NO_2$. The reaction rate increases when the NO concentration is higher, or the oxygen concentration is higher. The reaction is not very sensitive to temperature near standard temperature and pressure. During inhaled NO treatment, it is necessary to maintain a constant concentration of inhaled NO, while minimally diluting the inspiratory flow. Therefore, the NO source is typically a reasonably high concentration (~500-1000 ppm). If the NO source is a tank of compressed gas, and the balance gas is an inert species such as nitrogen, the only significant $NO_2$ formation occurs in the inspiratory circuit after the NO-rich gas is mixed in the correct proportion with the inspiratory flow to achieve the desired dose concentration.

In some embodiments, an electric arc is used to generate nitric oxide from ambient air. The nitric oxide (NO) is present in concentration on the order of 50-5000 ppm depending on the desired dose and inspiratory flow. However, leftover oxygen and nitrogen remain virtually unchanged from their atmospheric concentrations of approximately 21% and 78% respectively. Therefore, $NO_2$ is forming from the moment NO is generated in the arc. Some of this $NO_2$ can be chemically removed after the electric NO generator before the NO-rich gas is mixed into the inspiratory flow.

Depending on the detailed design of the pneumatic circuit, and the details of the inspiratory flow rate and NO-therapy, the residence time of the NO-rich, $O_2$-rich gas in the volume after chemical $NO_2$ removal but before injection may be excessive. Excessive residence time leads to greater $NO_2$ formation.

In some embodiments, there is a recirculating loop of NO-rich gas. The gas is constantly circulating, and only a portion is diverted to the inspiratory limb. Recirculation limits residence time, so $NO_2$ formation can be limited. Moreover, gas that returns to the NO source can be "re-scrubbed" so to limit $NO_2$ accumulation.

Figure 60:
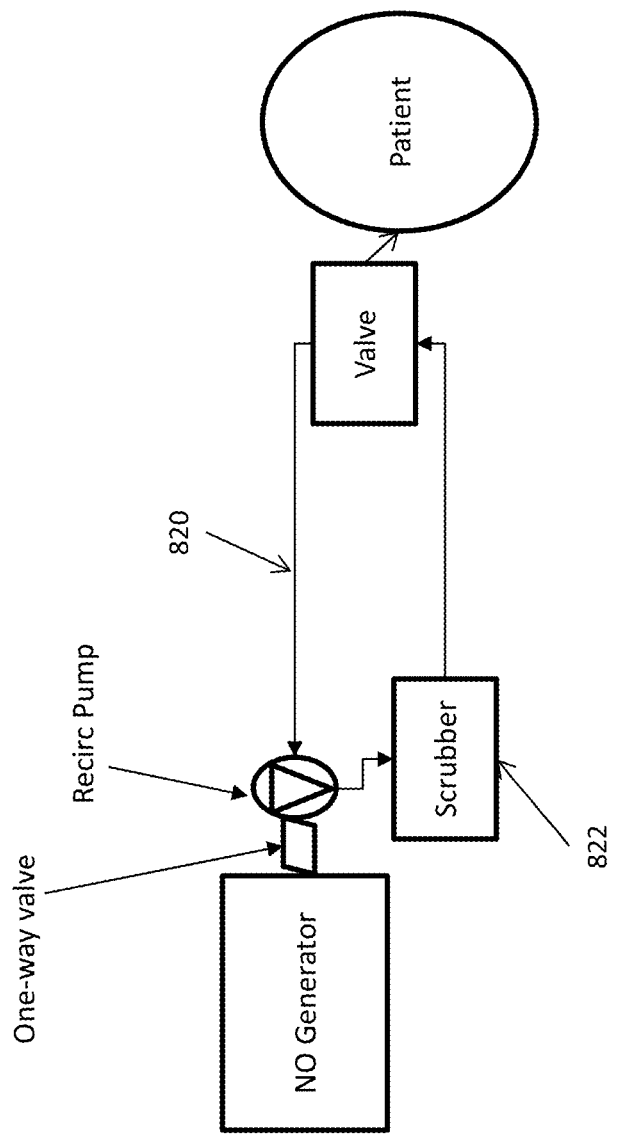
FIG. 60 is an embodiment of a recirculating loop that continuously removes NO$_2$ from stores NO-containing gas.

FIG. 60 illustrates an embodiment of a recirculating loop 820 that continuously removes $NO_2$ using a scrubber 822 from stored NO-containing gas. A valve opens to inject NO containing gases as directed by the NO generator. In some embodiments, the valve opens open patient inspiration.

Figure 61:
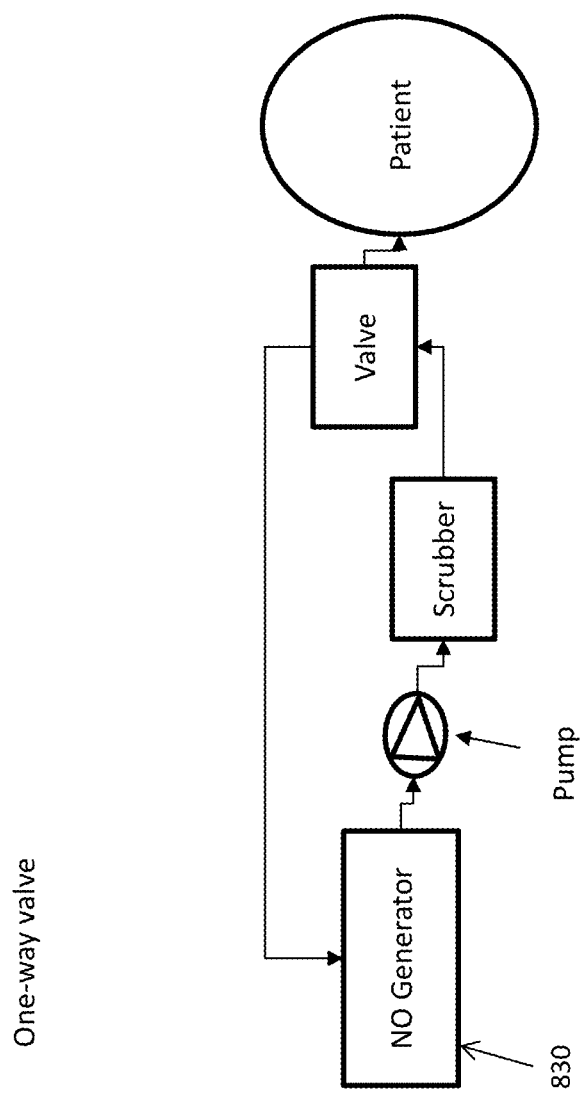
FIG. 61 is an embodiment of a system where recirculated gas flows back through the NO generator.

FIG. 61 illustrates an embodiment of a system where recirculated gas flows back through the NO generator 830. This is acceptable because only a fraction of $N_2$ and $O_2$ is converted to NO in the plasma chamber. Thus, additional NO can be generated from the same air.

The flow of NO-rich gas can be directed to the inspiratory limb by closing the injection valve on the return leg, otherwise NO-rich gas is continuously recirculating in the loop. In some embodiments, a portion of the gases within the recirculation loop flow out of the loop and through gas analysis sensors within the system to monitor one or more of NO, $NO_2$, and $O_2$ levels in the product gas. In some embodiments, sample gases are drawn from the return leg of the recirculation circuit. In some embodiments, product gases are sampled after the scrubber.

Wearability

Figure 63:
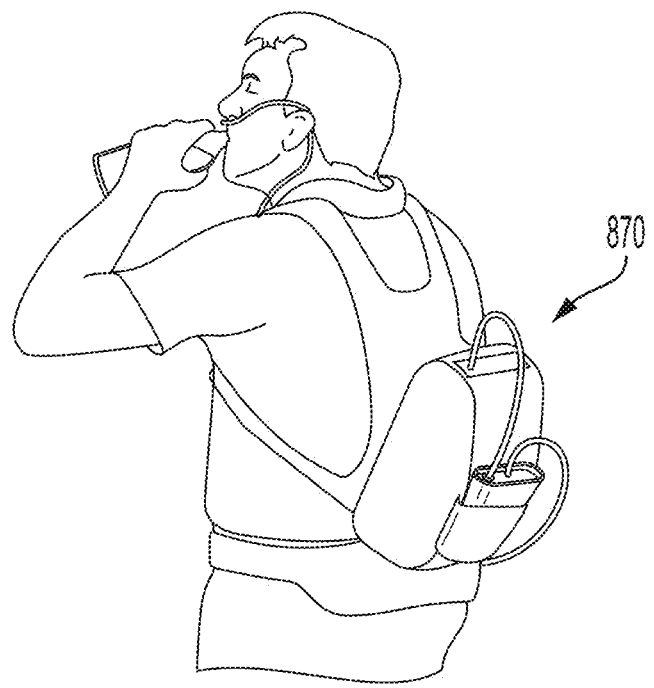
FIG. 63 is an embodiment of a portable NO device that is mounted in a backpack along with an oxygen concentrator.

FIG. 62A, FIG. 62B, FIG. 62C, and FIG. 62D depict various ways the system can be worn. The outer surface can have a variety of shapes. In some embodiments, the outer shape can have a concave curve for comfort when worn on a belt 840 (FIG. 62D) or shoulder strap 850 (FIG. 62C). The enclosure can include mounting points for a shoulder strap to connect. In an embodiment, the device 860 can be mounted to an $O_2$ generator 862 (FIG. 62A) or $O_2$ tanks 864 (FIG. 62B), aided by the concave shape of the device. In some embodiments, the device is mounted in a backpack 870 along with an oxygen concentrator (FIG. 63). Gas from the oxygen concentrator flows to the NO generation device and then on to the patient. In one embodiment, the cannula connection involves a single dual-lumen connector. In another embodiment, the cannula connection involves two separate single lumen connectors.

FIG. 46 also shows a body-worn sensor 661. NO generation systems can include one or more sensors to monitor patient condition and vital signs. Examples of body-worn sensors include sensors that measure motion (e.g. linear or angular displacement, velocity, acceleration, jerk), EKG, body temperature, heart rate, heart sound, respiratory rate, $SpO_2$, blood pressure, $CO_2$, and other physiological parameters. The body-worn sensor communicates with the NO generation device or a remote device through wireless and/or wired means and may serve as an input to the treatment control, alarm system or data logging.

Safety Features

Various safety features can be incorporated in the NO generation device. In an embodiment, safety features can be used when a device sits idle for a while, as NO within the delivery tube can turn to $NO_2$. Prior to resuming use, the tube can be rid of $NO_2$ without pumping the NO to the patient. For example, the NO delivery pump can be run in reverse to pull $NO_2$ away from the patient and into the scavenger. The pump can run for a certain amount of time or for a certain number of pump rotations that can be related to the volume of the NO delivery line. In one embodiment, the duration of pump purge activity is determined by the cannula length which is entered into or read by the controller. After the $NO_2$ has been removed from the tube, the pump can return to forward flow and plasma generation can be initiated. In an embodiment, the system can prevent NO from residing the NO delivery line when treatment is not being administered. The pump can be run for a period of time after plasma generation stops thereby purging the NO delivery line with air and pushing all of the NO out to the patient. In another approach, lines can be blown out, or purged of all gas before beginning treatment.

In one embodiment, product gas is analyzed with one or more gas sensors prior to exiting the NO generation device and entering the cannula. These effluent gases can be analyzed for NO, $NO_2$ and $O_2$ content, for example. In another embodiment, a dedicated lumen in the cannula is used to pull a sample of product gases from the delivery lumen to gas analysis sensors for analysis.

It is important for an NO generation device to know that reactant gas flow is occurring through the plasma reservoir. In one embodiment, an NO generation device uses one or more of the following means to ensure reactant gas flow: sensing pump motor current, an encoder related to pump and/or motor operation, a flow sensor that detects reactant gas flow within the reactant gas flow path, one or more pressure sensors within the plasma chamber or in fluid communication with the reactant gas flow, a thermistor within the reactant gas flow, and/or a hot wire anemometer within the reactant gas flow.

One issue that can occur with cannula-based NO delivery is kinking of the delivery line, potentially slowing or stopping NO delivery to the patient. In some embodiments, the system can use one or more of the following indicators to detect a kinked line: NO line pressure, $O_2$ line pressure, NO pump current, NO line flow, $O_2$ line flow, respiration signal fidelity, and plasma activity (suppressed by high pressure).

Another issue that can occur with an ambulatory NO generation device that delivers through a cannula is mouth breathing. Talking and snoring can also present respiratory conditions similar to mouth breathing. Patients that breath through their mouth do not receive the same dose as when they breathe through their nose when wearing a nasal cannula. In some embodiments, the NO generation and delivery system can detect inadequate nasal respiration and/or mouth breathing and can respond by increasing the NO delivery to accommodate and/or warning the user. If the system is able to deliver NO to the patient (pump current is normal, NO flow is normal) but if the system is not able to detect respirations at the nose, then the patient is probably breathing through their mouth.

Other safety features can also be included with an ambulatory NO generation device. It is possible for users to forget to replace the $NO_2$ scavenger component at appropriate times. In some embodiments, a device can prompt a user to replace a scavenger when they remove the device from the charger in the morning. In some embodiments, an ambulatory device can include a built-in accelerometer to detect patient activity. In some embodiments, an ambulatory device can include features to detect patient exertion and provide a warning. The warning can be based on various measurements and data, including accelerometer data and/or respiratory rate.

In one embodiment, an NO generation and delivery system can provide feedback to the user and/or $O_2$ delivery system regarding the $O_2$ delivery treatment. For example, in one embodiment, the flow rate of $O_2$ through the NO delivery system is measured. In the event that $O_2$ pulses do not coincide with patient respirations or are not happening at all, the NO generation system can generate an alarm for the user. In one embodiment, the NO generation and delivery system provides a breath detection signal for an $O_2$ delivery system.

In one embodiment, the NO generation system can alert the user if there is evidence that the current NO dose level is not correct. For example, low $SpO_2$ levels or high heart rate can indicate that the patient is not receiving sufficient NO. In this case, the device could warn the user. In one embodiment, the NO dose level is changed automatically, within reasonable limits to see if an adjustment in NO dose can improve a physiological parameter.

In some embodiments, an NO generation and delivery device alters the dose level over time based on the patient's physiological response to NO. In some embodiments, a high NO dose is delivered to the patient for an initial period of time to dilate the patient's lung vessels followed by a lower NO dose to sustain the lung vessel dilation.

Figure 64:
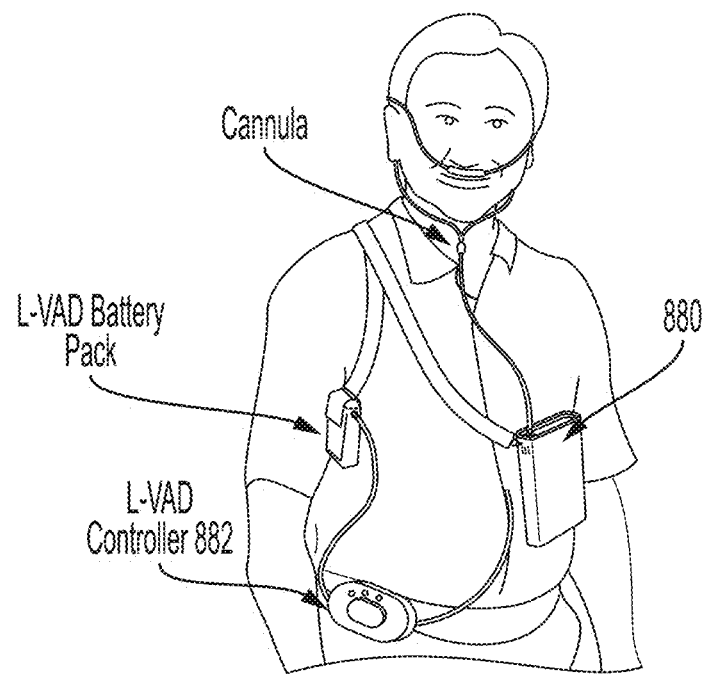
FIG. 64 is an exemplary embodiment of a portable NO generation device in conjunction with an LVAD.

In some embodiments, a portable NO generation device 880 can be controlled such that it can only be used in conjunction with another therapy, including but not limited to a left ventricular assist device 882 (LVAD) as shown in FIG. 64. This feature can be used to ensure proper use from a regulatory standpoint and can also help ensure compliance in a clinical trial to ensure that multiple therapies are used together. The NO generation device can be configured to determine that the compatible therapy is present in a variety of ways. In some embodiments, wireless communication between an NO generation device and the complimentary device can be achieved using Bluetooth, Wi-Fi, infra-red, or other communication techniques. This can also allow for active communication between the devices to share treatment information and ensure that both devices are active. In some embodiments, an NO generation device can include functionality to scan a label on the complimentary device prior to operation. In some embodiments, an RFID chip could be placed on the complimentary device so that the NO generation device can sense the RFID chip. In some embodiments, an RFID chip could be placed in the complimentary device so that the NO generation device can sense the RFID chip.

Figure 65:
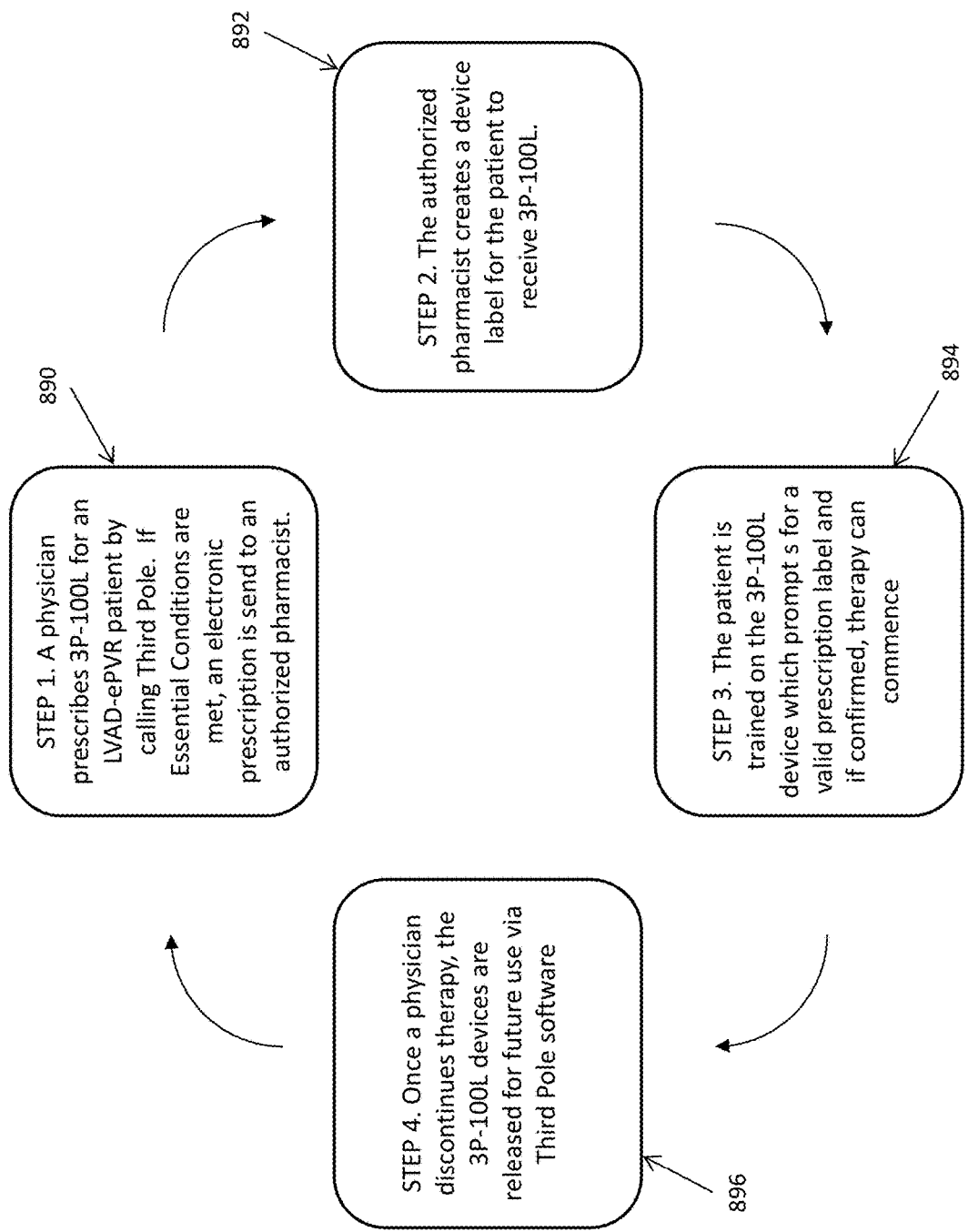
FIG. 65 is an exemplary flowchart of a method of ensuring a portable NO device is used properly in conjunction with another therapy.

FIG. 65 illustrates an exemplary embodiment of a workflow for ensuring a portable NO device is used properly in conjunction with another therapy. In some embodiments, a registry can be maintained that includes information including but not limited to devices, device association data, the number of patients treated, and current status. In use, to ensure proper use of a portable NO generation device that can only be used in conjunction with another therapy, a physician who is primarily responsible for registering a patient for NO therapy can communicate with a central repository of information for order processing to check and/or register the associated devices (Step 890). This can ensure that one or more conditions are met:

the patient is an authorized user of the therapy and a physician wishes to commence NO therapy. For example, in the case of a portable NO device being used with a LVAD, this can be based on hemodynamic data confirming persistent elevation of pulmonary vascular resistance (PVR) despite LVAD placement (LVAD-ePVR).

a plurality (for example, two) portable NO devices (for example, a main and back-up device) with unique device identifiers (UDI) are available in a medical facility.

the UDI of the patient's LVAD is available.

if required, the regulatory limit of patients (for example, 8,000 patients) treated with a portable NO device in a particular year has not been reached.

If all the required conditions are met, the physician can register the portable NO devices and the UDI of the LVAD as well as one or more patient identifiers, with measures to protect confidentiality in accordance with HIPAA. The physician can generate an electronic prescription for the patient that is forwarded to a pharmacy. A prescription label for a portable NO device can be created under certain conditions, including but not limited to a valid prescription being generated by the physician, and the device association data being available (Step 892).

A physician or other medical professional, for example a respiratory therapist, can train a patient on the portable NO device and can activate the device for the first time (Step 894). In some embodiment, the portable NO devices prompt for a valid prescription label and reads the prescription label, seeks a valid expiration date and the clinical indication which must be LVAD associated with elevated PVR. The portable NO device reads device association data (UDIs for the device). If the required information for is validated, the device is enabled and therapy can commence. If any element of the required information is not met, the device alarms and therapy cannot commence. If during therapy, any elements of the required prescription information become invalid (for example, the prescription expiration date has passed), the device will alarm and therapy will terminate. Once therapy is discontinued for any reason, the physician can discontinue therapy and release the portable NO devices for use with a new patient (Step 896).

In use, the initiation of treatment with a stand-alone, ambulatory NO generator can include the steps of ensuring that a controller battery is fully charged, and removing a fresh cartridge from a vacuum-sealed packaging. The cartridge is installed into the controller by orienting it with the nasal cannula connection up and flat side toward a user display. The cartridge is pressed down into the controller until a user senses a tactile and/or audible "click." A nasal cannula is connected to the connector at the top of the cartridge, and the controller is turned on. It will be understood that the cannula and cartridge can also be unitary. The controller can go through a boot process and cartridge check. If the cartridge is used or expired, the controller user display can present an alarm. Upon successful completion of a boot and cartridge check, all indicators on the user interface can be green and the device can automatically begin delivering NO.

In use, the initiation of treatment with an NO generation system and oxygen concentrator can include the steps of ensuring that the controller battery is fully charged, and removing a fresh cartridge from a vacuum-sealed packaging. The cartridge is installed into the controller by orienting it with the nasal cannula connection up and flat side toward the User display. The cartridge is pressed down into the controller until the user senses a tactile and/or audible "click." A method of carrying the NO generation device is selected and installed. For example, the controller can be attached to an oxygen bottle or an oxygen generator, and the NO generation device can be worn on a belt or on a shoulder strap. The oxygen side of the dual-lumen cannula is connected to the oxygen source, and the oxygen tube is pressed into the oxygen tube groove in the NO device enclosure until it is fully seated. The NO side of the dual-lumen cannula is connected to the output of the NO generator. The cannula prongs are placed in the nose of a patient and the left and right tubes are run around the corresponding ear. Any excess cannula tubing is coiled and secured to the NO generator with the attached strap. The $O_2$ concentrator is turned on and its settings are adjusted to the desired outputs. The NO generation device is turned on, and the NO delivery setting are chosen (for example, synchronous, asynchronous, or constant NO delivery). The desired NO output in ppm and flow rate is also chosen.

In some embodiments, a flat prismatic Lithium Ion battery pack is used to enable compact packing of the device.

In some embodiments, the ambulatory NO generation device is designed to automatically increase NO production upon detection of activity within preprogrammed limits. The +/− buttons can be used to adjust the NO dose within preprogrammed limits. A "Boost" button can be used for a brief bolus of NO. Disposable cartridges are identified with a proprietary memory device. In one embodiment, one or more of the following parameters are entered into a disposable component memory device: cannula length, cannula inner diameter, cannula volume, the patient height, ideal body weight, and/or current weight. The system will not function without cartridges from the OEM.

All patents, patent applications, and published references cited herein are hereby incorporated by reference in their entirety. It will be appreciated that several of the above-disclosed and other features and functions, or alternatives thereof, may be desirably combined into many other different systems or application. Various alternatives, modifications, variations, or improvements therein may be subsequently made by those skilled in the art.

The invention claimed is:

1. A system for providing nitric oxide (NO) comprising:
a NO generation system comprising:
a housing configured to be portable;
a reactant gas flow path configured to provide a reactant gas to one or more plasma chambers;
one or more electrodes located in the one or more plasma chambers configured to generate a product gas containing nitric oxide using a flow of the reactant gas through the one or more plasma chambers;
a controller configured to regulate the amount of nitric oxide generated in the reactant gas; and
one or more scrubber paths configured to remove $NO_2$ from the product gas generated by the one or more plasma chambers;
wherein the NO generation system is integrated with a device selected from a group consisting of a ventilator, a defibrillator, a ventricular assist device (VAD), a Continuous Positive Airway Pressure (CPAP) machine, a Bilevel Positive Airway Pressure (BiPAP) machine, a non-invasive positive pressure ventilator (NIPPV), a nasal cannula application, a nebulizer, an extracorporeal membrane oxygenation (ECMO), a bypass system, an automated CPR system, an oxygen delivery system, an oxygen concentrator, an oxygen generation system, and an automated external defibrillator AED such that the NO generation system is electrically connected to the device,
wherein the controller determines a resonant frequency of a high voltage circuit and wherein the resonant frequency is determined throughout a service life of the system.

2. The system of claim 1, wherein the one or more scrubber paths includes one or more inlet filters and/or one or more exhaust filters.

3. The system of claim 1, further comprising one or more filters positioned to receive NO-enriched air from the one or more scrubber paths and configured to filter the NO-enriched air.

4. The system of claim 1, further comprising a connector to deliver the product gas to at least one of a patient delivery device and the device with which the portable NO generation system is integrated.

5. The system of claim 4, wherein the patient delivery device is selected from a group consisting of a nasal cannula, a tube located near an ear, a tube in communication with a trachea, a face mask, and a CPAP mask.

6. The system of claim 1, wherein the system is configured to be used with an oxygen generator or an oxygen concentrator to increase nitric oxide production.

7. The system of claim 1, wherein the resonant frequency of the high voltage circuit is automatically determined at a power-up of the system.

8. The system of claim 1, wherein the resonant frequency of the high voltage circuit is automatically determined at the beginning of each patient treatment.

9. The system of claim 1, wherein the resonant frequency is stored in memory so that a resonance search is not required.

10. The system of claim 1, wherein the controller is configured to regulate the amount of nitric oxide generated in the reactant gas by regulating a flow of the reactant gas in the reactant gas flow path.

11. The system of claim 1, further comprising a user interface configured to allow a user to interact with the system, view information about the system and nitric oxide production, and control parameters related to nitric oxide production.

12. The system of claim 1, further comprising a user interface that includes illuminated indicators for alarm status, battery charge status, external power connection, scrubber and/or filter cartridge remaining life, $O_2$ flow detection, GSM connection, and/or NO generation.

13. The system of claim 1, further comprising one or more antennae for GSM, Bluetooth, WiFi and/or other connectivity.

14. The system of claim 1, further comprising a reactant gas source in the form of a reservoir in fluid communication with the one or more plasma chambers.

15. The system of claim 1, wherein the NO generation system is configured to work with manual CPR such that the NO generation system is configured to detect respiration as a result of chest compression and supplement inhaled air with NO.

16. The system of claim 1, wherein the NO generation system is configured to draw power from a power supply of the device.

17. A system for providing nitric oxide (NO) comprising:
a NO generation system comprising:
a reactant flow path configured to provide a reactant gas to one or more plasma chambers;

one or more electrodes located in the one or more plasma chambers configured to generate a product gas containing nitric oxide using a flow of the reactant gas through the one or more plasma chambers;

a controller configured to regulate the amount of nitric oxide generated in the reactant gas; and one or more scrubber paths configured to remove $NO_2$ from the product gas generated by the one or more plasma chambers;

wherein the NO generation system is integrated into a device selected from a group consisting of a ventilator, a defibrillator, a ventricular assist device (VAD), a Continuous Positive Airway Pressure (CPAP) machine, a Bilevel Positive Airway Pressure (BiPAP) machine, a non-invasive positive pressure ventilator (NIPPV), a nasal cannula application, a nebulizer, an extracorporeal membrane oxygenation (ECMO), a bypass system, an automated CPR system, an oxygen delivery system, an oxygen concentrator, an oxygen generation system, and an automated external defibrillator AED such that the NO generation system is embedded in the device.

18. The system of claim 17, wherein the controller determines a resonant frequency of a high voltage circuit.

19. The system of claim 18, wherein the resonant frequency of the high voltage circuit is stored in a memory.

20. The system of claim 18, wherein the resonant frequency is automatically determined at a power-up of the system.

21. The system of claim 18, wherein the resonant frequency of the high voltage circuit is automatically determined at the beginning of each patient treatment.

22. The system of claim 18, wherein the resonant frequency is stored in memory so that a resonance search is not required.

23. The system of claim 17, further comprising a connector to deliver the product gas to a patient delivery device.

24. The system of claim 17, wherein the NO generation system is configured to share at least one of a battery, user display, alarm system, speaker and microprocessor with the device into which it is integrated.

25. The system of claim 17, wherein the scrubber path is integrated into a scrubber cartridge.

26. A system for providing nitric oxide (NO) comprising:
a NO generation system comprising:
a housing configured to be portable;
a reactant gas flow path configured to provide a reactant gas to one or more plasma chambers;
one or more electrodes located in the one or more plasma chambers configured to generate a product gas containing nitric oxide using a flow of the reactant gas through the one or more plasma chambers;
a controller configured to regulate the amount of nitric oxide generated in the reactant gas; and
one or more scrubber paths configured to remove $NO_2$ from the product gas generated by the one or more plasma chambers;
wherein the NO generation system is integrated with a device selected from a group consisting of a ventilator, a defibrillator, a ventricular assist device (VAD), a Continuous Positive Airway Pressure (CPAP) machine, a Bilevel Positive Airway Pressure (BiPAP) machine, a non-invasive positive pressure ventilator (NIPPV), a nasal cannula application, a nebulizer, an extracorporeal membrane oxygenation (ECMO), a bypass system, an automated CPR system, an oxygen delivery system, an oxygen concentrator, an oxygen generation system, and an automated external defibrillator AED such that the NO generation system is embedded with the device.

27. A system for providing nitric oxide (NO) comprising:
a NO generation system comprising:
a reactant gas flow path configured to provide a reactant gas to one or more plasma chambers;
one or more electrodes located in the one or more plasma chambers configured to generate a product gas containing nitric oxide using a flow of the reactant gas through the one or more plasma chambers;
a controller configured to regulate the amount of nitric oxide generated in the reactant gas; and
one or more scrubber paths configured to remove $NO_2$ from the product gas generated by the one or more plasma chambers;
wherein the NO generation system is integrated with a device selected from a group consisting of a ventilator, a defibrillator, a ventricular assist device (VAD), a Continuous Positive Airway Pressure (CPAP) machine, a Bilevel Positive Airway Pressure (BiPAP) machine, a non-invasive positive pressure ventilator (NIPPV), a nasal cannula application, a nebulizer, an extracorporeal membrane oxygenation (ECMO), a bypass system, an automated CPR system, an oxygen delivery system, an oxygen concentrator, an oxygen generation system, and an automated external defibrillator AED such that the NO generation system is electrically connected to the device,
wherein the controller determines a resonant frequency of a high voltage circuit and wherein the resonant frequency is determined throughout a service life of the system.

28. A system for providing nitric oxide (NO) comprising:
a NO generation system comprising:
a housing configured to be portable;
a reactant gas flow path configured to provide a reactant gas to one or more plasma chambers;
one or more electrodes located in the one or more plasma chambers configured to generate a product gas containing nitric oxide using a flow of the reactant gas through the one or more plasma chambers;
a controller configured to regulate the amount of nitric oxide generated in the reactant gas; and
one or more scrubber paths configured to remove $NO_2$ from the product gas generated by the one or more plasma chambers;
wherein the NO generation system is integrated with a device selected from a group consisting of a ventilator, a defibrillator, a ventricular assist device (VAD), a Continuous Positive Airway Pressure (CPAP) machine, a Bilevel Positive Airway Pressure (BiPAP) machine, a non-invasive positive pressure ventilator (NIPPV), a nasal cannula application, a nebulizer, an extracorporeal membrane oxygenation (ECMO), a bypass system, an automated CPR system, an oxygen delivery system, an oxygen concentrator, an oxygen generation system, and an automated external defibrillator AED such that the NO generation system is electrically connected to the device,
wherein the controller determines a resonant frequency of a high voltage circuit and wherein the resonant frequency is stored in memory so that a resonance search is not required.

* * * * *